(12) United States Patent
Bishai et al.

(10) Patent No.: US 10,988,512 B2
(45) Date of Patent: Apr. 27, 2021

(54) METHODS OF PRODUCING AGGREGATE-FREE MONOMERIC DIPHTHERIA TOXIN FUSION PROTEINS AND THERAPEUTIC USES

(71) Applicants: The Johns Hopkins University, Baltimore, MD (US); Trustees of Boston University, Boston, MA (US)

(72) Inventors: William R. Bishai, Baltimore, MD (US); John R. Murphy, Tilghman, MD (US); Laurene Cheung, Baltimore, MD (US); Shashank Gupta, Baltimore, MD (US); Cynthia K. Bullen, Baltimore, MD (US)

(73) Assignees: The Johns Hopkins University, Baltimore, MD (US); Trustees of Boston University, Boston, MA (US)

( * ) Notice: Subject to any disclaimer, the term of this patent is extended or adjusted under 35 U.S.C. 154(b) by 0 days.

(21) Appl. No.: 16/083,848

(22) PCT Filed: Mar. 10, 2017

(86) PCT No.: PCT/US2017/021715
§ 371 (c)(1),
(2) Date: Sep. 10, 2018

(87) PCT Pub. No.: WO2017/156356
PCT Pub. Date: Sep. 14, 2017

(65) Prior Publication Data
US 2019/0071472 A1    Mar. 7, 2019

Related U.S. Application Data

(60) Provisional application No. 62/306,281, filed on Mar. 10, 2016.

(51) Int. Cl.
| | | |
|---|---|---|
| *A61K 38/00* | (2006.01) | |
| *C07K 14/34* | (2006.01) | |
| *C12N 15/77* | (2006.01) | |
| *C07K 14/55* | (2006.01) | |
| *C12P 21/02* | (2006.01) | |
| *C12N 15/63* | (2006.01) | |
| *A61K 38/16* | (2006.01) | |
| *A61K 38/20* | (2006.01) | |
| *C12N 15/62* | (2006.01) | |

(52) U.S. Cl.
CPC ............. *C07K 14/34* (2013.01); *A61K 38/00* (2013.01); *A61K 38/164* (2013.01); *A61K 38/2013* (2013.01); *C07K 14/55* (2013.01); *C12N 15/63* (2013.01); *C12N 15/77* (2013.01); *C12P 21/02* (2013.01); *C07K 2319/02* (2013.01); *C07K 2319/034* (2013.01); *C07K 2319/21* (2013.01); *C07K 2319/33* (2013.01); *C07K 2319/55* (2013.01); *C12N 15/62* (2013.01)

(58) Field of Classification Search
None
See application file for complete search history.

(56) References Cited

U.S. PATENT DOCUMENTS

| | | |
|---|---|---|
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,614,382 A | 3/1997 | Metcalf |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 5,863,897 A | 1/1999 | Gallo et al. |
| 5,932,471 A | 8/1999 | Williams et al. |
| 5,965,406 A | 10/1999 | Murphy |
| 6,022,950 A | 2/2000 | Murphy |
| 6,613,308 B2 | 9/2003 | Bartus et al. |
| 6,737,514 B1 | 5/2004 | Wang et al. |
| 7,585,942 B2 | 9/2009 | Harrison et al. |
| 8,252,897 B2 | 8/2012 | Davis et al. |

(Continued)

FOREIGN PATENT DOCUMENTS

| | | |
|---|---|---|
| EP | 2 716 661 A1 | 9/2014 |
| JP | S 60-227681 | 11/1982 |

(Continued)

OTHER PUBLICATIONS

Matthey, B., et al., "A new series of pET-derived vectors for high efficiency expression of Pseudomonas exotoxin-based fusion proteins" Gene 229 (1999) 145-153.
Ton-That et al., Assembly of pili on the surface of Corynebacterium diphtheriae. Mol Microbiol. Nov. 2003;50(4):1429-38.
Shafer et al., (1994) Small mobilizable multi-purpose cloning vectors 5 derived from the *Escherichia coli* plasmids pK18 and pK19: selection of defined deletions in the chromosome of Corynebacterium glutumicum. Gene 145:69-73.
Allen et al., HtaA is an iron-regulated hemin binding protein involved in the utilization of heme iron in Corynebacterium diphtheriae. J Bacteriol. Apr. 2009;191(8):2638-48.

(Continued)

*Primary Examiner* — Jennifer E Graser
(74) *Attorney, Agent, or Firm* — DLA Piper LLP (US)

(57) ABSTRACT

The present invention is a DNA expression vector comprising: a toxP; a mutant toxO that blocks Fe-mediated regulation of gene expression; and a DNA sequence encoding a protein, wherein the toxP and the mutant toxO regulate expression of the DNA segment encoding the protein. It is preferred that DNA expression vectors of the present invention include DNA sequences encoding a signal peptide so that a protein expressed is attached to the signal peptide prior to processing. Novel proteins are produced off of the DNA expression vector of the present invention.

7 Claims, 16 Drawing Sheets
Specification includes a Sequence Listing.

(56) References Cited

U.S. PATENT DOCUMENTS

| | | | |
|---|---|---|---|
| 8,865,866 B2 | 10/2014 | Harrison et al. | |
| 8,906,681 B2* | 12/2014 | Kelly | C07K 1/1077 435/326 |
| 2006/0159708 A1 | 7/2006 | Harrison et al. | |
| 2006/0167238 A1 | 7/2006 | Murphy et al. | |
| 2013/0034547 A1* | 2/2013 | Kelly | C07K 1/1077 424/133.1 |

FOREIGN PATENT DOCUMENTS

| | | |
|---|---|---|
| JP | H03-504248 A | 11/1989 |
| WO | 2012039954 A2 * | 3/2012 |

OTHER PUBLICATIONS

Tao et al., Determination of the minimal essential nucleotide sequence for diphtheria tox repressor binding by in vitro affinity selection., Proc Natl Acad Sci U S A. Sep. 27, 1994;91(20):9646-50.

Takenaga et al., 1998 Microparticle resins as a potential nasal drug delivery system for insulin., J Control Release 52:81-7.

Mathiowitz et al., 1997 Biologically erodable microspheres as potential oral drug delivery systems., Nature 386(6623):410-4.

Baldo, B., "Chimeric Fusion Proteins Used for Therapy: Indications, Mechanisms, and Safety", Drug Saf (2015)38:455-479.

Kohanski, M., et al., "How antibiotics kill bacteria: from targets to networks", Nat Rev Microbiol. Jun. 2010 ; 8(6):423-435.

Divanovic, S., et al., "Therapeutic Enhancement of Protective Immunity during Experimental Leishmaniasis" PLoS Negl Trop Dis (2011) vol. 5, No. 9, e1316.

Saltini, C., "Chemotherapy and diagnosis of tuberculosis", Respiratory Medicine (2006) 100, 2085-2097.

Dang, N., et al., "Phase II trial of denileukin diftitox for relapsed/refractory T-cell non-Hodgkin lymphoma" British Journal of Haematology, (2006) vol. 136, pp. 439-447.

Bachran, C., et al., "Recombinant Expression and Purification of a Tumor-Targeted Toxin in Bacillus anthracis" Biochem Biophys Res Commun. Jan. 4, 2013; 430(1): 150-155.

Tauch, A., et al., "Efficient Electrotransformation of Corynebacterium diphtheriae with a Mini-Replicon Derived from the Corynebacterium glutamicum Plasmid pGA1" Current Microbiology vol. 45 (2002), pp. 362-367.

Williams, D., et al., "Diphtheria toxin receptor binding domain substitution with interleukin-2: genetic construction and properties of a diphtheria toxin-related interleukin-2 fusion protein" Protein Engineering (1987) vol. 1, No. 6, pp. 493-498.

Bishai, W. et al., "High-level expression of proteolytically sensitive diphtheria toxin fragment in *Escherichia coli*" Journal of Bacteriology (1987) vol. 169, No. 11, pp. 5140-5151.

Lee, J., et al., "Characterization of Specific Nucleotide Substitutions in DtxRSpecific Operators of Corynebacterium diphtheriae That Dramatically Affect DtxR Binding, Operator Function, and Promoter Strength" Journal of Bacteriology, (2000) vol. 182, No. 2, pp. 432-438.

Japanese Office Action dated Dec. 14, 2020, regarding JP 2018-547409.

Tao and Murphy: "Determination of the minimal essential nucleotide sequence for diphtheria tox repressor binding by in vitro affinity selection";Proc. Natl. Acad. Sci., Sep. 1994, vol. 91, pp. 9646-9650.

Vanderspeck et al.: "Fusion Protein" [synthetic construct]; Jul. 23, 1993, Retrieved from GenBank [online] Accession No. AAA72359.1 [retrieved on Nov. 24, 2020] URL: [http://wvwv.ncbi.nlm.nih.gov/protein/AAA72359.1].

* cited by examiner

FIG. 1 toxO sequence and mutations a) Mutant toxO in *this invention report*:
TTAGGATAGCT*A*AGT*CC*AT    (altered bases shown in *red*)

b) Wild type toxO
TTAGGATAGCTTTACCTAA    19 bp imperfect palindrome around the large C FIG. 2 Addition of the *tox* promoter, mutant *tox* operator, and signal sequence in pKN2.6Z-LC127 a) Classic denileukin diftitox (c-denileukin diftitox) expression vector

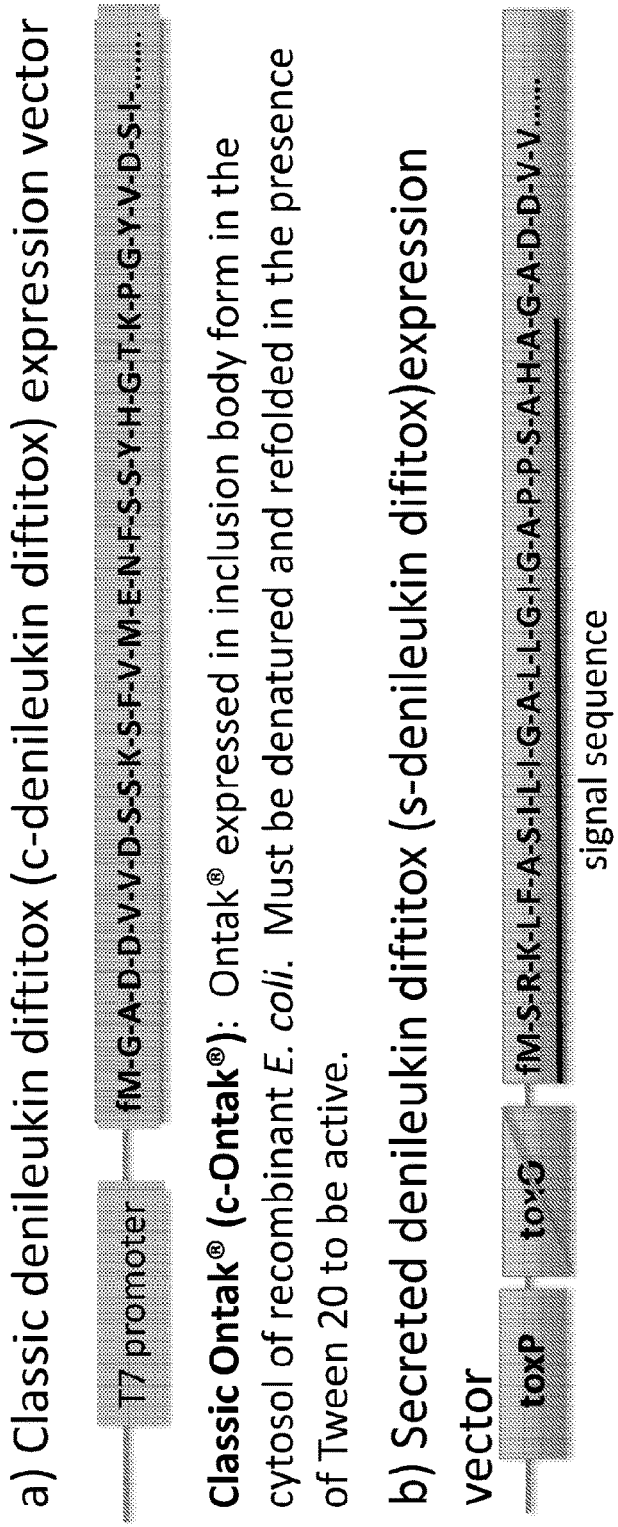

Classic Ontak® (c-Ontak®): Ontak® expressed in inclusion body form in the cytosol of recombinant *E. coli*. Must be denatured and refolded in the presence of Tween 20 to be active.

b) Secreted denileukin diftitox (s-denileukin difitox)expression vector

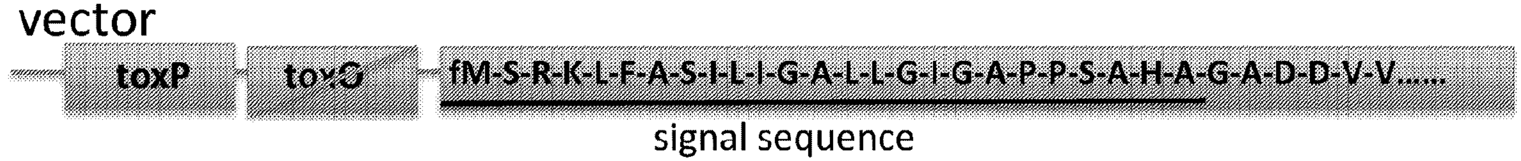

Secreted Ontak® (s-Ontak®): expressed as a secreted protein (i) into the periplasm of recombinant *E. coli*, or (ii) into the spent culture medium of recombinant *C. diphtheriae*, C7s(-)tox-, as a fully folded biologically active protein. The red slash indicates that the *toxO* operator sequence has been mutated to prevent DtxR repressor binding. The mutant *toxO* enables constitutive, iron-independent expression of the downstream gene.

FIG. 3 c-denileukin diftitox-VLM shows similar activity to c-denileukin diftitox c-denileukin diftitox-VLM has a potency equivalent to c-denileukin diftitox for killing IL-2R bearing cells Cell Toxicity Assay $IC_{50}s$ are within experimental error % control [$^{14}C$]-leucine incorporation Fusion Protein Toxin Concentration (M)

c-denileukin diftitox — c-denileukin
C-diftitox ▪ diftitox

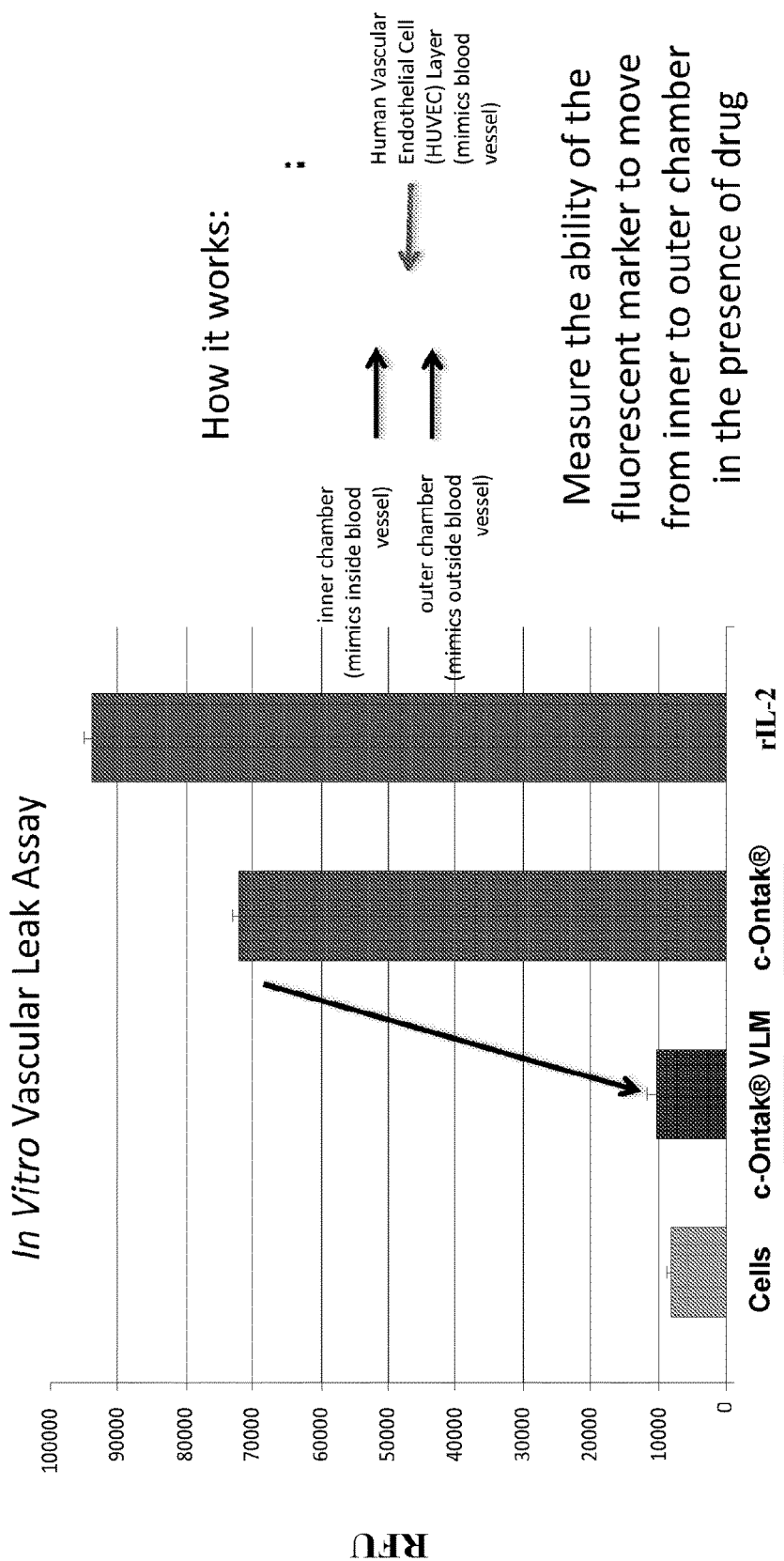
FIG. 4 c-denileukin diftitox-VLM : decreased vascular leak

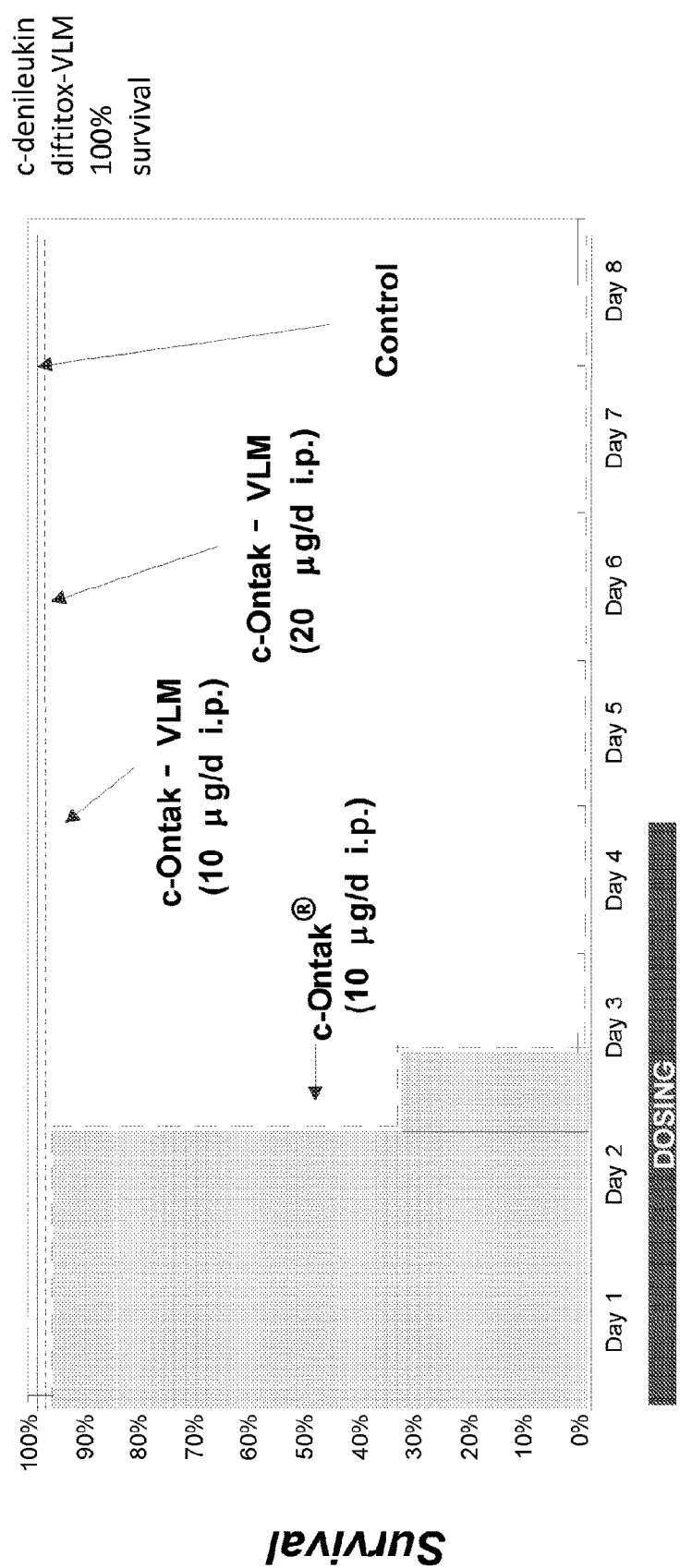

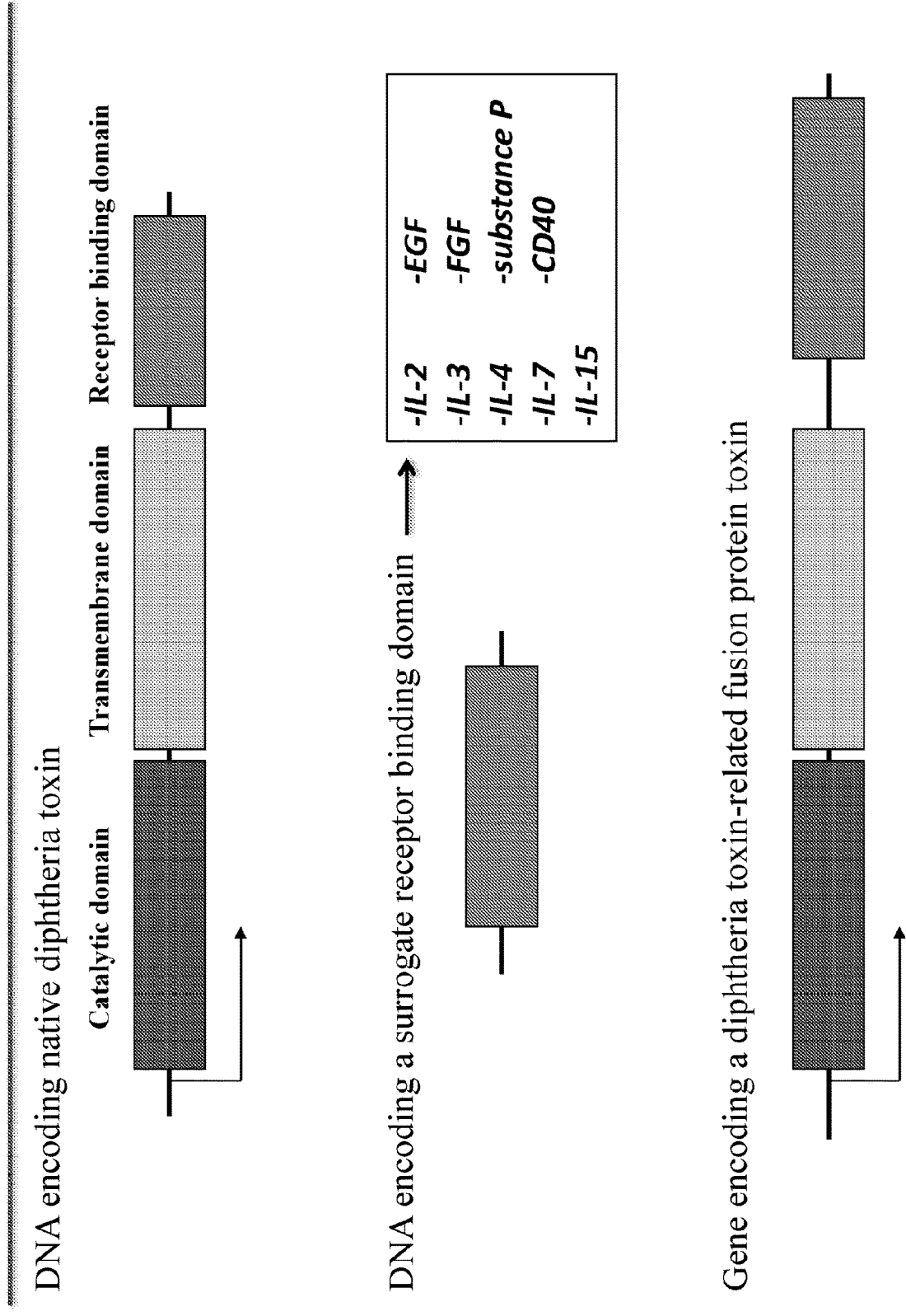

FIG. 7 Construct to express s-denileukin diftitox from *Corynebacterium diphtheriae* as a secreted protein into the culture medium in an iron-independent manner

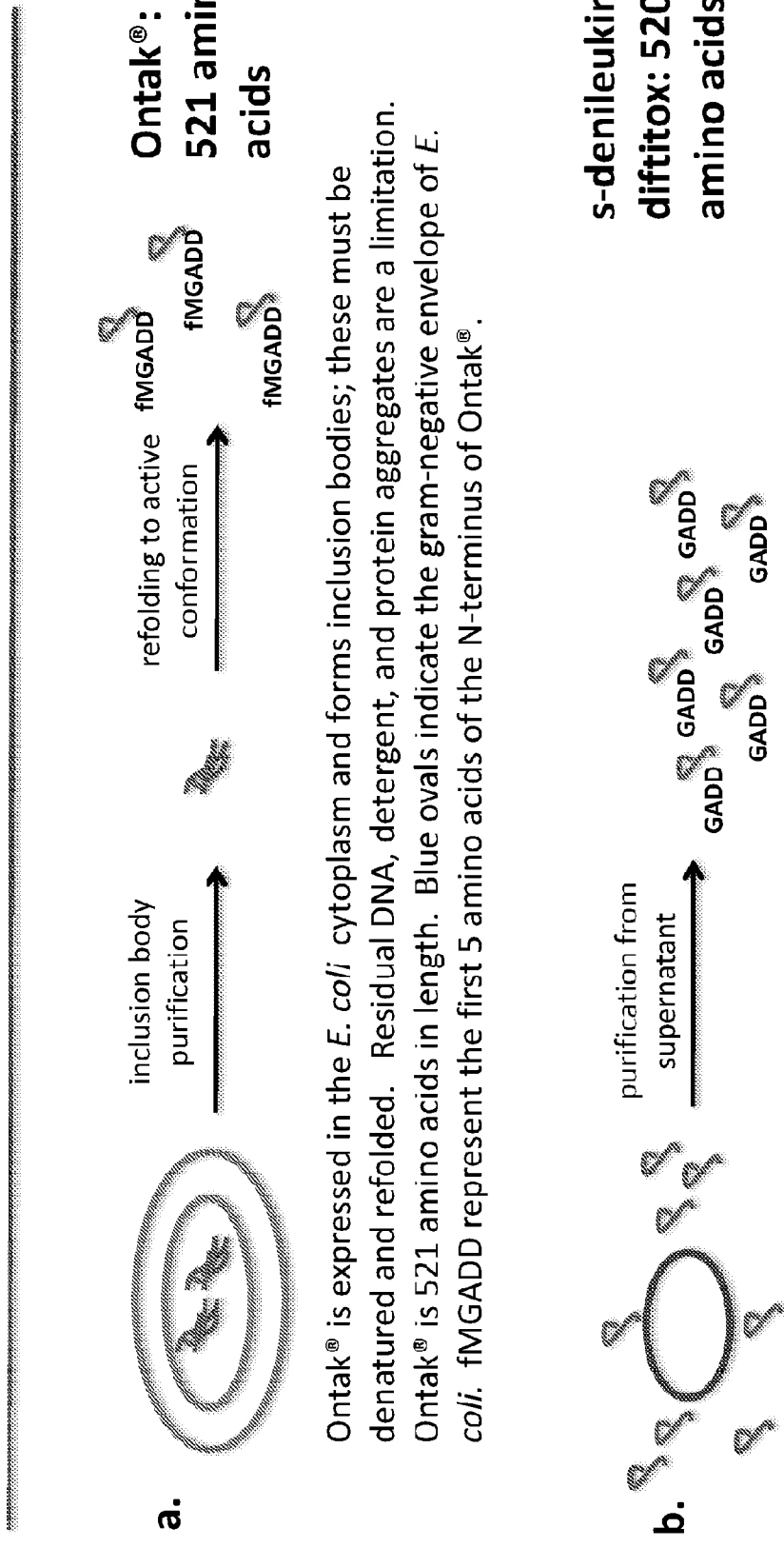

FIG. 8: Addressing the problems of inclusion body formation, denaturation, and refolding required for c-denileukin diftitox production a.

Ontak® is expressed in the *E. coli* cytoplasm and forms inclusion bodies; these must be denatured and refolded. Residual DNA, detergent, and protein aggregates are a limitation. Ontak® is 521 amino acids in length. Blue ovals indicate the gram-negative envelope of *E. coli.* fMGADD represent the first 5 amino acids of the N-terminus of Ontak®.

b.

s-denileukin diftitox is expressed by *C. diphtheriae* as a secreted protein into the cell free culture supernatant fluid in biologically active form. Mature s-denileukin diftitox is 520 amino acids in length. Red oval indicates the gram-positive envelop of *C. diphtheriae.* GADD represent the first 4 amino acids of the N-terminus of s-denileukin diftitox of the present invention.

FIG. 9 s-denilekin diftitox: expressed as a secreted protein into the culture medium of *Corynebacterium diphtheriae* strain C7(-) *tox*-

1: Protein size ladder
2: Coomassie blue stain
3: anti-IL-2 Western blot

Molecular Weight (kD): 250, 130, 100, 70, 55, 35, 25, 15 supernatant was concentrated 10x and 23 microliters of concentrate was loaded onto the gel

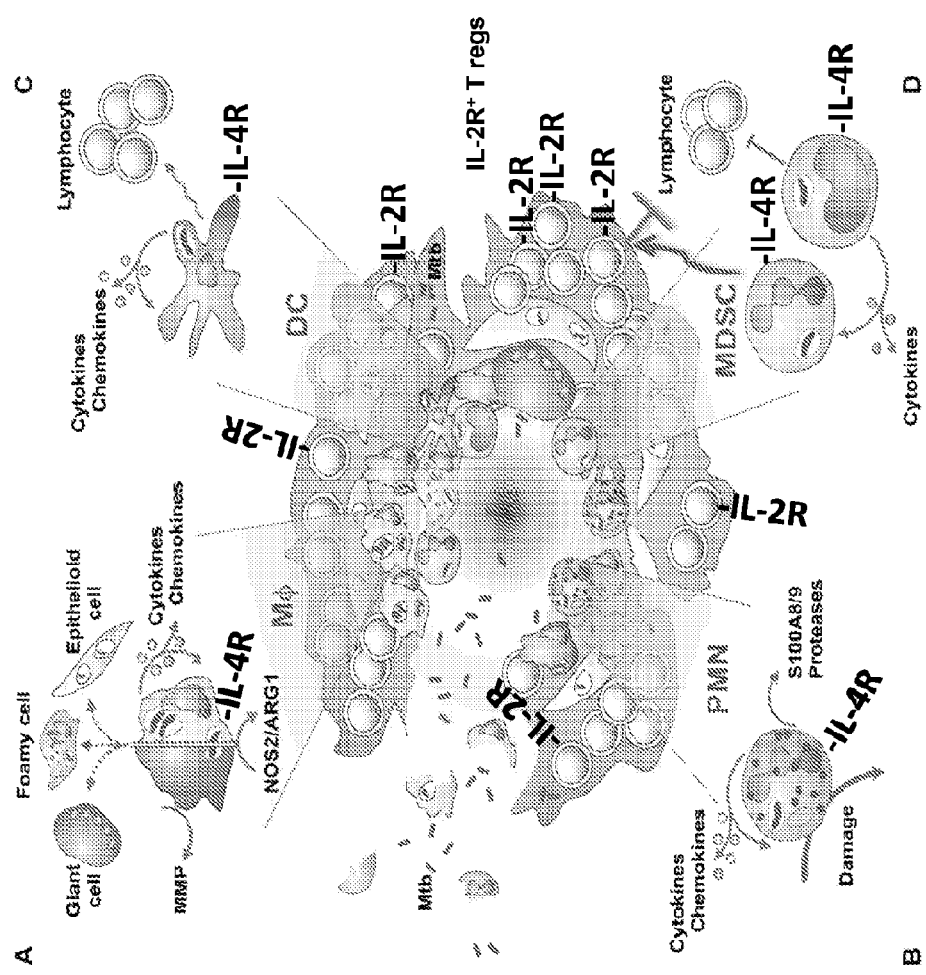
FIG. 10 Ontak® ($DAB_{389}IL-2$) is expected to deplete IL-2R-bearing (CD25+) T cells ($T_{regs}$) within the tuberculous granuloma. $T_{regs}$ are immunosuppressive by their inhibition of $T_{eff}$ cells

FIG 11. ONTAK for TB. Mouse TB Model. Experimental Scheme

| Treatment | Week 0 No of mice sacrificed for CFU counts | Week 2 No of mice sacrificed for CFU counts | Week 5 No of mice sacrificed for CFU counts |
|---|---|---|---|
| Grp 1. No treatment | 5 | 5 | 5 |
| Grp 2. Ont-2x IP | 5 | 5 | 5 |
| Grp 3. Ont-2x IV | | 5 | 5 |
| Grp 4. Ont-1x IP | | 5 | 5 |
| Grp 5. RHZ | | | 5 |
| Grp 6. RHZ + Ont-1x IP | | | 5 |

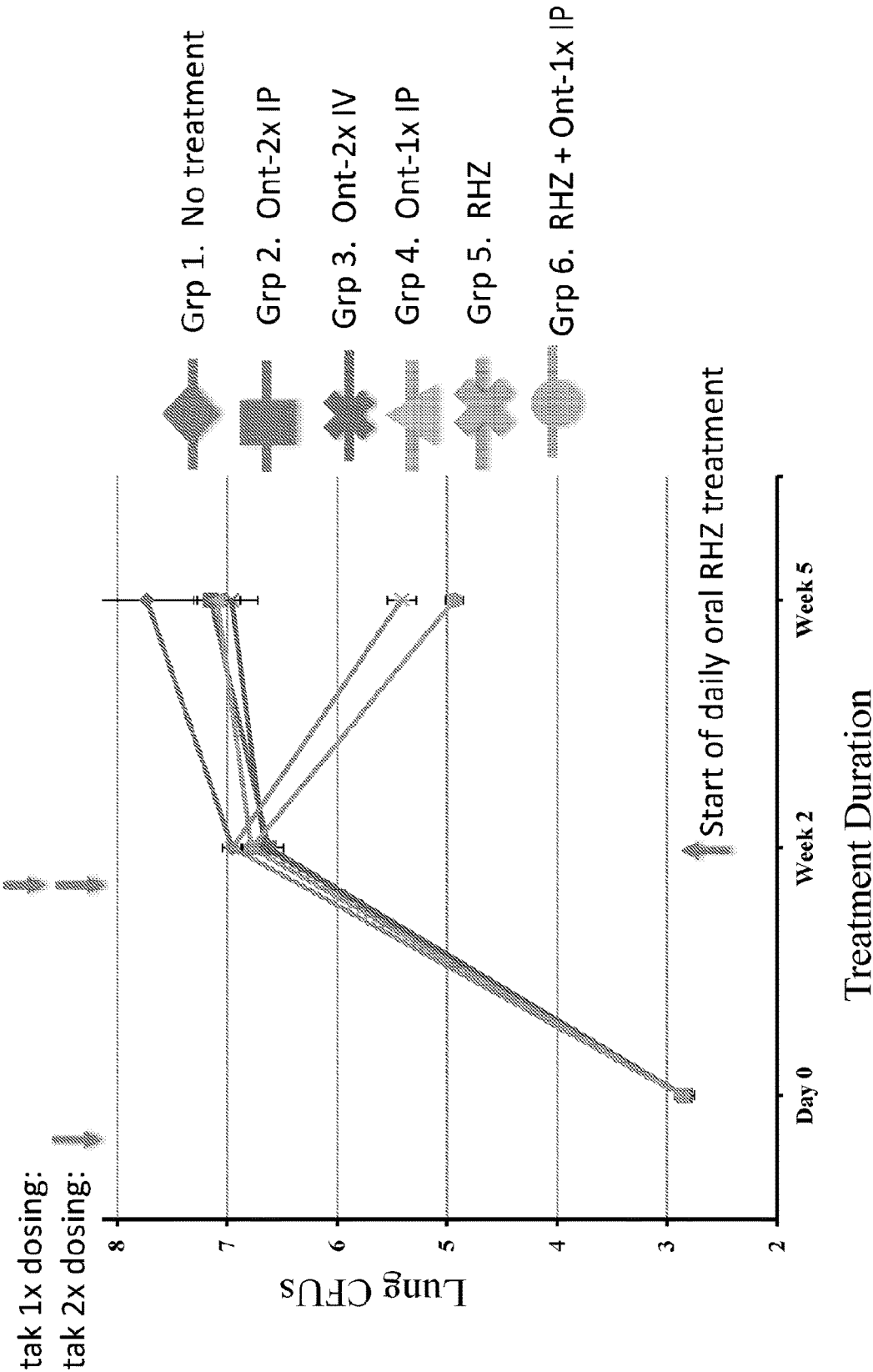

FIG 13. Ontak to treat TB. Mouse TB Model
Lung CFUs during treatment with different c-denileukin diftitox regimens Data from Figure 12 with just Group 1 (no treatment) and Group 4 (c-denileukin diftitox 1x or one treatment cycle as monotherapy IP at week 2 post-infection)

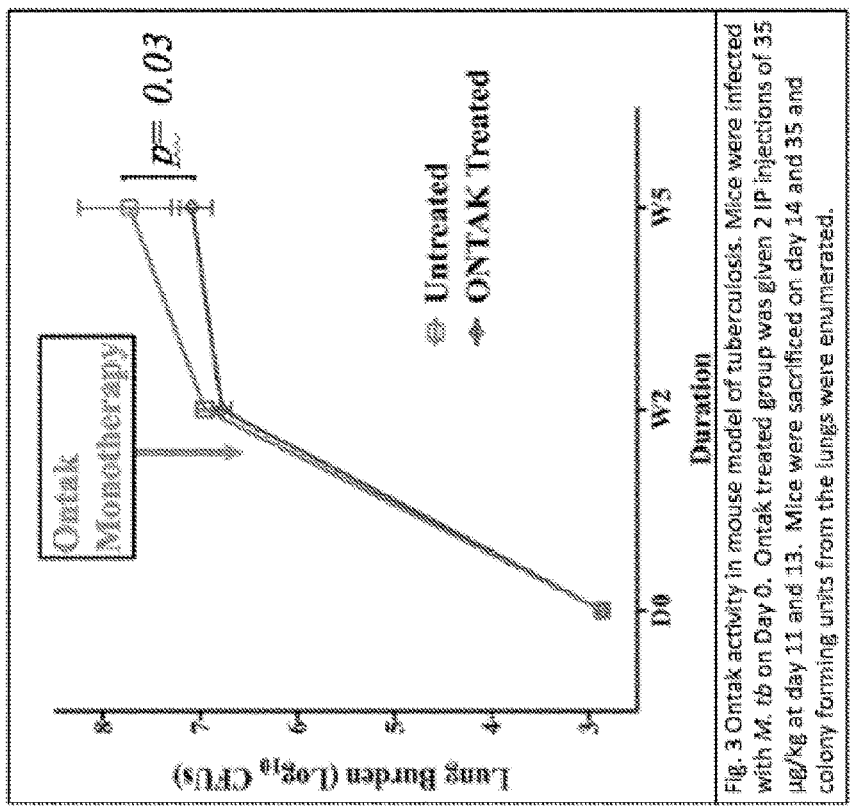

Fig. 3 Ontak activity in mouse model of tuberculosis. Mice were infected with M. tb on Day 0. Ontak treated group was given 2 IP injections of 35 µg/kg at day 11 and 13. Mice were sacrificed on day 14 and 35 and colony forming units from the lungs were enumerated.

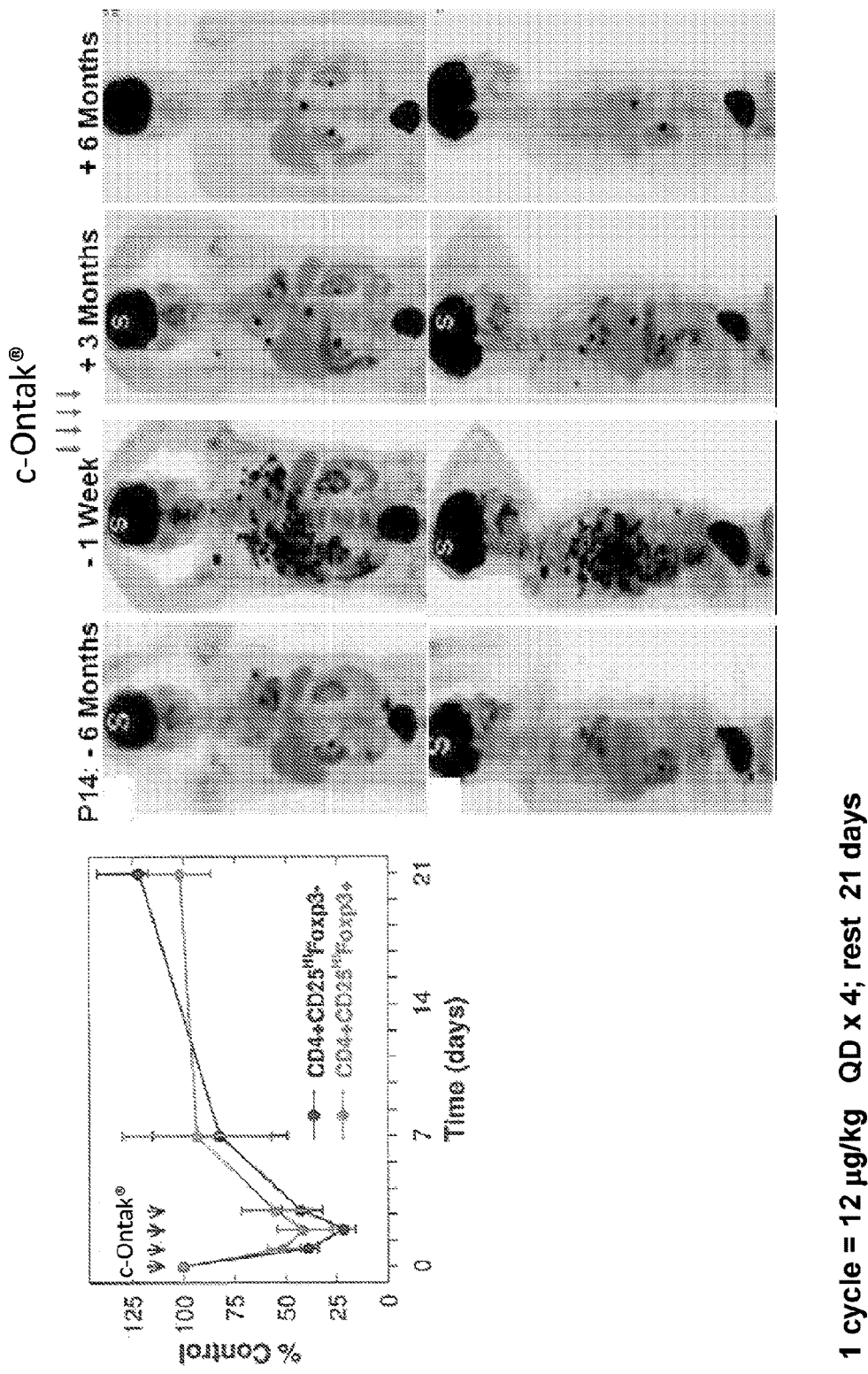
FIG. 14 c-denileukin diftitox as an immunotherapeutic agent: Malignant Melanoma
1 cycle = 12 µg/kg QD x 4; rest 21 days

FIG. 15 Ontak production: His tag
N-terminal: His$_6$-TEV-VLM s-Ontak
C-terminal: His$_6$-VLM s-Ontak
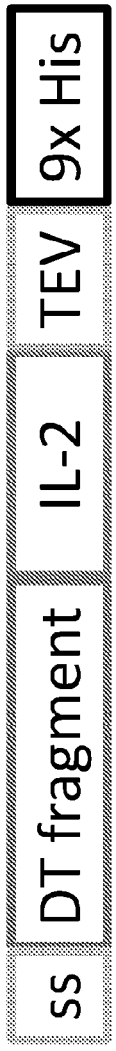
C terminus TEV-His$_9$-VLM s-Ontak

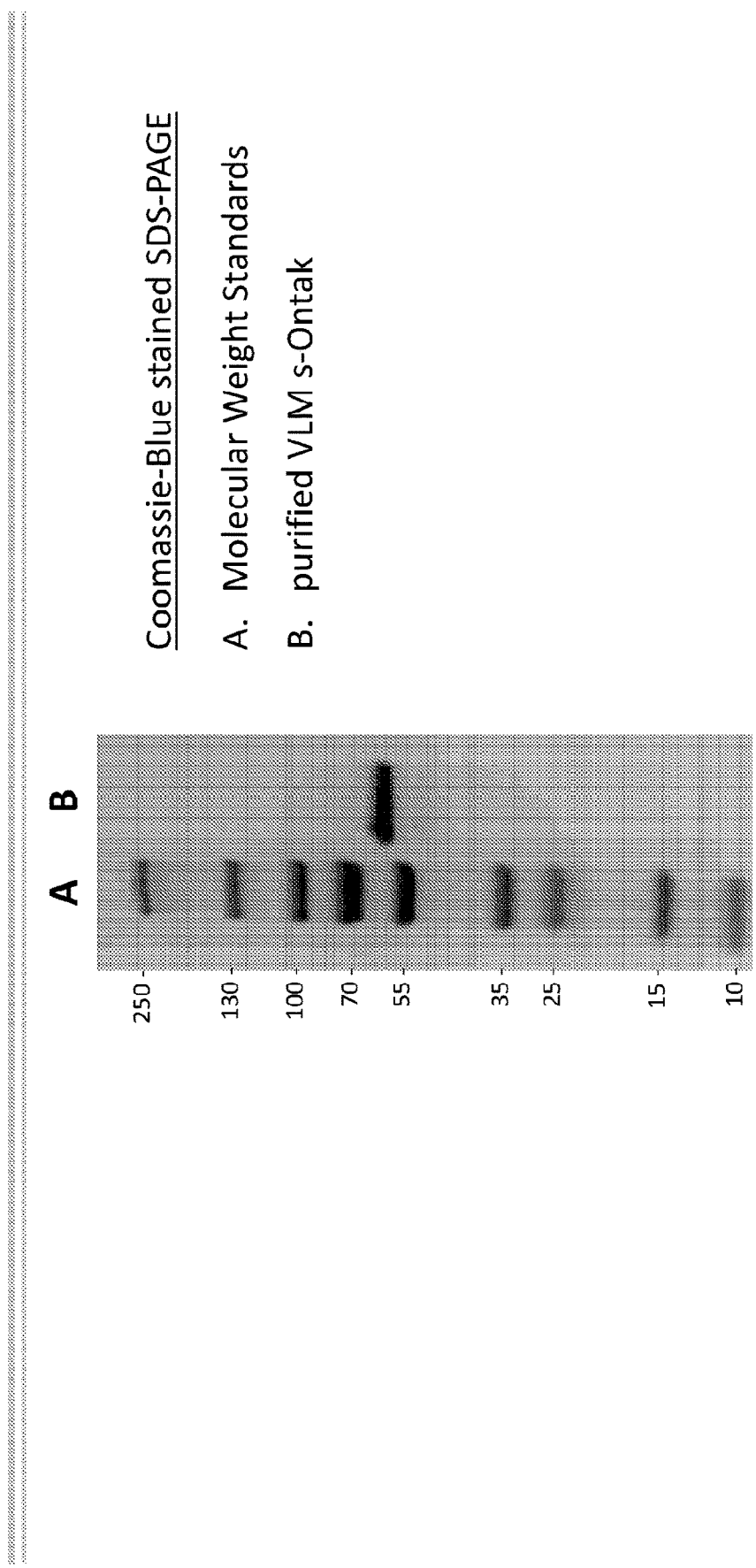
FIG 16. VLM s-Ontak:
*Purification to > 97% with C-terminal His6-tagged VLM s-Ontak*

SEQUENCE LISTING

```
<160> NUMBER OF SEQ ID NOS: 48

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttaggatagc taagtccat                                                    19

<210> SEQ ID NO 2
<211> LENGTH: 42
<212> TYPE: DNA
<213> ORGANISM: Artificial Sequence
```

<220> FEATURE:
<223> OTHER INFORMATION: Description of Artificial Sequence: Synthetic oligonucleotide

<400> SEQUENCE: 2
ttgatttcag agcacccttaa taattaggat agctaagtcc at        42

<210> SEQ ID NO 3
<211> LENGTH: 1711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| | |
|---|---|
| ttgatttcag agcacccttaa taattaggat agctaagtcc attattttat gagtcctggt | 60 |
| aagggggatac gttgtgagca gaaaactgtt tgcgtcaatc ttaataggggg cgctactggg | 120 |
| gataggggcc ccaccttcag cccatgcagg cgctgatgat gttgttgatt cttctaaatc | 180 |
| ttttgtgatg gaaaactttt cttcgtacca cgggactaaa cctggttatg tagattccat | 240 |
| tcaaaaaggt atacaaaagc caaaatctgg tacacaagga aattatgacg atgattggaa | 300 |
| agggttttat agtaccgaca ataaatacga cgctgcggga tactctgtag ataatgaaaa | 360 |
| cccgctctct ggaaaagctg gaggcgtggt caaagtgacg tatccaggac tgacgaaggt | 420 |
| tctcgcacta aaagtggata tgccgaaac tattaagaaa gagttaggtt taagtctcac | 480 |
| tgaaccgttg atggagcaag tcggaacgga agagtttatc aaaaggttcg gtgatggtgc | 540 |
| ttcgcgtgta gtgctcagcc ttcccttcgc tgaggggagt tctagcgttg aatatattaa | 600 |
| taactgggaa caggcgaaag cgttaagcgt agaacttgag attaattttg aaacccgtgg | 660 |
| aaaacgtggc caagatgcga tgtatgagta tatggctcaa gcctgtgcag gaaatcgtgt | 720 |
| caggcgatca gtaggtagct cattgtcatg catcaacctg gattgggatg ttatccgtga | 780 |
| taaaactaaa actaagatcg aatctctgaa agaacacggt ccgatcaaaa acaaaatgag | 840 |
| cgaaagcccg aacaaaactg tatctgaaga aaaagctaaa cagtacctgg aagaattcca | 900 |
| ccagactgca ctggaacacc cggaactgtc tgaacttaag accgttactg gtaccaaccc | 960 |
| ggtattcgct ggtgctaact acgctgcttg ggcagtaaac gttgctcagg ttatcgatag | 1020 |
| cgaaactgct gataacctgg aaaaaactac cgcggctctg tctatcctgc cgggtatcgg | 1080 |
| tagcgtaatg ggcatcgcag acggcgccgt tcaccacaac actgaagaaa tcgttgcaca | 1140 |
| gtctatcgct ctgagctctc tgatggttgc tcaggccatc ccgctggtag gtgaactggt | 1200 |
| tgatatcggt ttcgctgcat acaacttcgt tgaaagcatc atcaacctgt tccaggttgt | 1260 |
| tcacaactct tacaaccgcc cggcttactc tccgggtcac aagacgcatg cacctacttc | 1320 |
| tagctctacc aagaaaaccc agctgcagct cgagcacctg ctgctggatt tgcagatgat | 1380 |
| cctgaacggt atcaacaatt acaagaaccc gaaactgacg cgtatgctga ccttcaagtt | 1440 |
| ctacatgccg aagaaggcca ccgaactgaa acacctgcag tgtctagaag aagaactgaa | 1500 |
| accgctggag gaagttctga acctggctca gtctaaaaac ttccacctgc ggccgcgtga | 1560 |
| cctgatctct aacatcaacg taatcgttct ggaactgaag ggctctgaaa ccaccttcat | 1620 |
| gtgtgaatac gctgatgaga ccgcaaccat cgtagaattc ctgaaccgtt ggatcacctt | 1680 |
| ctgtcagtct atcatctcta ccctgacctg a | 1711 |

<210> SEQ ID NO 4

```
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtgagcagaa aactgtttgc gtcaatctta atagggggcgc tactggggat aggggcccca    60
ccttcagccc atgca                                                      75

<210> SEQ ID NO 5
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Ser Arg Lys Leu Phe Ala Ser Ile Leu Ile Gly Ala Leu Leu Gly
1               5                   10                  15

Ile Gly Ala Pro Pro Ser Ala His Ala
            20                  25

<210> SEQ ID NO 6
<211> LENGTH: 1566
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgggcgctg atgatgttgt tgattcttct aaatcttttg tgatggaaaa cttttcttcg    60
taccacggga ctaaacctgg ttatgtagat tccattcaaa aaggtataca aaagccaaaa   120
tctggtacac aaggaaatta tgacgatgat tggaaagggt tttatagtac cgacaataaa   180
tacgacgctg cgggatactc tgtagataat gaaaacccgc tctctggaaa agctggaggc   240
gtggtcaaag tgacgtatcc aggactgacg aaggttctcg cactaaaagt ggataatgcc   300
gaaactatta gaaagagtt aggtttaagt ctcactgaac cgttgatgga gcaagtcgga   360
acggaagagt ttatcaaaag gttcggtgat ggtgcttcgc gtgtagtgct cagccttccc   420
ttcgctgagg ggagttctag cgttgaatat attaataact gggaacaggc gaaagcgtta   480
agcgtagaac ttgagattaa ttttgaaacc cgtggaaaac gtggccaaga tgcgatgtat   540
gagtatatgg ctcaagcctg tgcaggaaat cgtgtcaggc gatcagtagg tagctcattg   600
tcatgcatca acctggattg ggatgttatc cgtgataaaa ctaaaactaa gatcgaatct   660
ctgaaagaac acggtccgat caaaaacaaa atgagcgaaa gcccgaacaa aactgtatct   720
gaagaaaaag ctaaacagta cctggaagaa ttccaccaga ctgcactgga cacccggaa    780 ctgtctgaac ttaagaccgt tactggtacc aacccggtat cgctggtgc taactacgct    840 gcttgggcag taacgttgc tcaggttatc gatagcgaaa ctgctgataa cctggaaaaa   900
actaccgcgg ctcgtctat cctgccgggt atcggtagcg taatgggcat cgcagacggc   960
gccgttcacc acaacactga agaaatcgtt gcacagtcta tcgctctgag ctctctgatg  1020
gttgctcagg ccatcccgct ggtaggtgaa ctggttgata tcggtttcgc tgcatacaac  1080
ttcgttgaaa gcatcatcaa cctgttccag gttgttcaca actcttacaa ccgcccggct  1140
```

| | |
|---|---:|
| tactctccgg gtcacaagac gcatgcacct acttctagct ctaccaagaa aacccagctg | 1200 |
| cagctcgagc acctgctgct ggatttgcag atgatcctga acggtatcaa caattacaag | 1260 |
| aacccgaaac tgacgcgtat gctgaccttc aagttctaca tgccgaagaa ggccaccgaa | 1320 |
| ctgaaacacc tgcagtgtct agaagaagaa ctgaaaccgc tggaggaagt tctgaacctg | 1380 |
| gctcagtcta aaaacttcca cctgcggccg cgtgacctga tctctaacat caacgtaatc | 1440 |
| gttctggaac tgaagggctc tgaaaccacc ttcatgtgtg aatacgctga tgagaccgca | 1500 |
| accatcgtag aattcctgaa ccgttggatc accttctgtc agtctatcat ctctaccctg | 1560 |
| acctga | 1566 |

<210> SEQ ID NO 7
<211> LENGTH: 1566
<212> TYPE: DNA
<213> ORGANISM: Artificial Sequence
<220> FEATURE:
<223> OTHER INFORMATION: Description of Artificial Sequence: Synthetic polynucleotide
<400> SEQUENCE: 7

| | |
|---|---:|
| atgggcgctg atgatgttgc tgattcttct aaatcttttg tgatggaaaa cttttcttcg | 60 |
| taccacggga ctaaacctgg ttatgtagat tccattcaaa aaggtataca aaagccaaaa | 120 |
| tctggtacac aaggaaatta tgacgatgat tggaaagggt tttatagtac cgacaataaa | 180 |
| tacgacgctg cgggatactc tgtagataat gaaaaccccgc tctctggaaa agctggaggc | 240 |
| gtggtcaaag tgacgtatcc aggactgacg aaggttctcg cactaaaagt ggataatgcc | 300 |
| gaaactatta gaaagagtt aggtttaagt ctcactgaac cgttgatgga gcaagtcgga | 360 |
| acggaagagt ttatcaaaag gttcggtgat ggtgcttcgc gtgtagtgct cagccttccc | 420 |
| ttcgctgagg ggagttctag cgttgaatat attaataact gggaacaggc gaaagcgtta | 480 |
| agcgtagaac ttgagattaa ttttgaaacc cgtggaaaac gtggccaaga tgcgatgtat | 540 |
| gagtatatgg ctcaagcctg tgcaggaaat cgtgtcaggc gatcagtagg tagctcattg | 600 |
| tcatgcatca acctggattg ggatgttatc cgtgataaaa ctaaaactaa gatcgaatct | 660 |
| ctgaaagaac acggtccgat caaaaacaaa atgagcgaaa gcccgaacaa aactgtatct | 720 |
| gaagaaaaag ctaaacagta cctggaagaa ttccaccaga ctgcactgga cacccggaa | 780 |
| ctgtctgaac ttaagaccgt tactggtacc aacccggtat cgctggtgc taactacgct | 840 |
| gcttgggcag taaacgttgc tcaggttatc gatagcgaaa ctgctgataa cctggaaaaa | 900 |
| actaccgcgc tctgtctat cctgccgggt atcggtagcg taatgggcat cgcagacggc | 960 |
| gccgttcacc acaacactga agaaatcgtt gcacagtcta tcgctctgag ctctctgatg | 1020 |
| gttgctcagg ccatcccgct ggtaggtgaa ctggttgata tcggtttcgc tgcatacaac | 1080 |
| ttcgttgaaa gcatcatcaa cctgttccag gttgttcaca actcttacaa ccgcccggct | 1140 |
| tactctccgg gtcacaagac gcatgcacct acttctagct ctaccaagaa aacccagctg | 1200 |
| cagctcgagc acctgctgct ggatttgcag atgatcctga acggtatcaa caattacaag | 1260 |
| aacccgaaac tgacgcgtat gctgaccttc aagttctaca tgccgaagaa ggccaccgaa | 1320 |
| ctgaaacacc tgctgcagtg tctagaagaa gaactgaaac cgctggagga agttctgaac | 1380 |
| ctggctcagt ctaaaaactt ccacctgcgg ccgcgtgacc tgatctctaa catcaacgta | 1440 |
| atcgttctgg aactgaaggg ctctgaaacc accttcatgt gtgaatacgc tgatgagacc | 1500 |
| gcaaccatcg tagaattcct gaaccgttgg atcaccttct gtcagtctat catctctacc | 1560 |

-continued ctgacc 1566

<210> SEQ ID NO 8
<211> LENGTH: 1638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | | | | | |
|---|---|---|---|---|---|
| gtgagcagaa | aactgtttgc | gtcaatctta | ataggggcgc | tactggggat | aggggcccca | 60 |
| ccttcagccc | atgcaggcgc | tgatgatgtt | gctgattctt | ctaaatcttt | tgtgatggaa | 120 |
| aacttttctt | cgtaccacgg | gactaaacct | ggttatgtag | attccattca | aaaaggtata | 180 |
| caaaagccaa | aatctggtac | acaaggaaat | tatgacgatg | attggaaagg | gttttatagt | 240 |
| accgacaata | aatacgacgc | tgcgggatac | tctgtagata | tgaaaaccc | gctctctgga | 300 |
| aaagctggag | gcgtggtcaa | agtgacgtat | ccaggactga | cgaaggttct | cgcactaaaa | 360 |
| gtggataatg | ccgaaactat | taagaaagag | ttaggtttaa | gtctcactga | accgttgatg | 420 |
| gagcaagtcg | gaacggaaga | gtttatcaaa | aggttcggtg | atggtgcttc | gcgtgtagtg | 480 |
| ctcagccttc | ccttcgctga | ggggagttct | agcgttgaat | atattaataa | ctgggaacag | 540 |
| gcgaaagcgt | taagcgtaga | acttgagatt | aattttgaaa | cccgtggaaa | acgtggccaa | 600 |
| gatgcgatgt | atgagtatat | ggctcaagcc | tgtgcaggaa | atcgtgtcag | gcgatcagta | 660 |
| ggtagctcat | tgtcatgcat | caacctggat | tgggatgtta | tccgtgataa | aactaaaact | 720 |
| aagatcgaat | ctctgaaaga | acacggtccg | atcaaaaaca | aaatgagcga | aagcccgaac | 780 |
| aaaactgtat | ctgaagaaaa | agctaaacag | tacctggaag | aattccacca | gactgcactg | 840 |
| gaacacccgg | aactgtctga | acttaagacc | gttactggta | ccaacccggt | attcgctggt | 900 |
| gctaactacg | ctgcttgggc | agtaaacgtt | gctcaggtta | tcgatagcga | aactgctgat | 960 |
| aacctggaaa | aaactaccgc | ggctctgtct | atcctgccgg | gtatcggtag | cgtaatgggc | 1020 |
| atcgcagacg | gcgccgttca | ccacaacact | gaagaaatcg | ttgcacagtc | tatcgctctg | 1080 |
| agctctctga | tggttgctca | ggccatcccg | ctggtaggtg | aactggttga | tatcggtttc | 1140 |
| gctgcataca | acttcgttga | aagcatcatc | aacctgttcc | aggttgttca | caactcttac | 1200 |
| aaccgcccgg | cttactctcc | gggtcacaag | acgcatgcac | ctacttctag | ctctaccaag | 1260 |
| aaaacccagc | tgcagctcga | gcacctgctg | ctggatttgc | agatgatcct | gaacggtatc | 1320 |
| aacaattaca | agaacccgaa | actgacgcgt | atgctgacct | tcaagttcta | catgccgaag | 1380 |
| aaggccaccg | aactgaaaca | cctgcagtgt | ctagaagaag | aactgaaacc | gctggaggaa | 1440 |
| gttctgaacc | tggctcagtc | taaaaacttc | cacctgcggc | cgcgtgacct | gatctctaac | 1500 |
| atcaacgtaa | tcgttctgga | actgaagggc | tctgaaacca | ccttcatgtg | tgaatacgct | 1560 |
| gatgagaccg | caaccatcgt | agaattcctg | aaccgttgga | tcaccttctg | tcagtctatc | 1620 |
| atctctaccc | tgacctga | | | | | 1638 |

<210> SEQ ID NO 9
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gcacctactt ctagctctac caagaaaacc cagctgcagc tcgagcacct gctgctggat      60
ttgcagatga tcctgaacgg tatcaacaat tacaagaacc cgaaactgac gcgtatgctg     120
accttcaagt tctacatgcc gaagaaggcc accgaactga acacctgcag tgtctagaa      180 gaagaactga aaccgctgga ggaagttctg aacctggctc agtctaaaaa cttccacctg     240
cggccgcgtg acctgatctc taacatcaac gtaatcgttc tggaactgaa gggctctgaa     300
accaccttca tgtgtgaata cgctgatgag accgcaacca tcgtagaatt cctgaaccgt     360
tggatcacct tctgtcagtc tatcatctct accctgacct ga                        402
```

<210> SEQ ID NO 10
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

Val Ile Asp Ser Glu Thr Ala Asp Asn Leu Glu Lys Thr Thr Ala Ala
        290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr His Ala Pro Thr Ser Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
            420                 425                 430

Tyr Met Pro Lys Lys Ala Thr Glu Leu Lys His Leu Gln Cys Leu Glu
        435                 440                 445

Glu Glu Leu Lys Pro Leu Glu Glu Val Leu Asn Leu Ala Gln Ser Lys
450                 455                 460

Asn Phe His Leu Arg Pro Arg Asp Leu Ile Ser Asn Ile Asn Val Ile
465                 470                 475                 480

Val Leu Glu Leu Lys Gly Ser Glu Thr Thr Phe Met Cys Glu Tyr Ala
                485                 490                 495

Asp Glu Thr Ala Thr Ile Val Glu Phe Leu Asn Arg Trp Ile Thr Phe
            500                 505                 510

Cys Gln Ser Ile Ile Ser Thr Leu Thr
        515                 520

<210> SEQ ID NO 11
<211> LENGTH: 560
<212> TYPE: PRT
<213> ORGANISM: Corynebacterium diphtheriae

<400> SEQUENCE: 11

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile G

```
                130             135             140
Thr Glu Glu Phe Ile Lys Arg Phe Gly Asp Gly Ala Ser Arg Val Val
145                 150             155             160

Leu Ser Leu Pro Phe Ala Glu Gly Ser Ser Val Glu Tyr Ile Asn
            165             170             175

Asn Trp Glu Gln Ala Lys Ala Leu Ser Val Glu Leu Glu Ile Asn Phe
                180             185             190

Glu Thr Arg Gly Lys Arg Gly Gln Asp Ala Met Tyr Glu Tyr Met Ala
            195             200             205

Gln Ala Cys Ala Gly Asn Arg Val Arg Arg Ser Val Gly Ser Ser Leu
            210             215             220

Ser Cys Ile Asn Leu Asp Trp Asp Val Ile Arg Asp Lys Thr Lys Thr
225             230             235             240

Lys Ile Glu Ser Leu Lys Glu His Gly Pro Ile Lys Asn Lys Met Ser
            245             250             255

Glu Ser Pro Asn Lys Thr Val Ser Glu Glu Lys Ala Lys Gln Tyr Leu
            260             265             270

Glu Glu Phe His Gln Thr Ala Leu Glu His Pro Glu Leu Ser Glu Leu
            275             280             285

Lys Thr Val Thr Gly Thr Asn Pro Val Phe Ala Gly Ala Asn Tyr Ala
290             295             300

Ala Trp Ala Val Asn Val Ala Gln Val Ile Asp Ser Glu Thr Ala Asp
305             310             315             320

Asn Leu Glu Lys Thr Thr Ala Ala Leu Ser Ile Leu Pro Gly Ile Gly
            325             330             335

Ser Val Met Gly Ile Ala Asp Gly Ala Val His His Asn Thr Glu Glu
            340             345             350

Ile Val Ala Gln Ser Ile Ala Leu Ser Ser Leu Met Val Ala Gln Ala
            355             360             365

Ile Pro Leu Val Gly Glu Leu Val Asp Ile Gly Phe Ala Ala Tyr Asn
            370             375             380

Phe Val Glu Ser Ile Ile Asn Leu Phe Gln Val Val His Asn Ser Tyr
385             390             395             400

Asn Arg Pro Ala Tyr Ser Pro Gly His Lys Thr Gln Pro Phe Leu His
            405             410             415

Asp Gly Tyr Ala Val Ser Trp Asn Thr Val Glu Asp Ser Ile Ile Arg
            420             425             430

Thr Gly Phe Gln Gly Glu Ser Gly His Asp Ile Lys Ile Thr Ala Glu
            435             440             445

Asn Thr Pro Leu Pro Ile Ala Gly Val Leu Leu Pro Thr Ile Pro Gly
            450             455             460

Lys Leu Asp Val Asn Lys Ser Lys Thr His Ile Ser Val Asn Gly Arg
465             470             475             480

Lys Ile Arg Met Arg Cys Arg Ala Ile Asp Gly Asp Val Thr Phe Cys
            485             490             495

Arg Pro Lys Ser Pro Val Tyr Val Gly Asn Gly Val His Ala Asn Leu
            500             505             510

His Val Ala Phe His Arg Ser Ser Glu Lys Ile His Ser Asn Glu
            515             520             525

Ile Ser Ser Asp Ser Ile Gly Val Leu Gly Tyr Gln Lys Thr Val Asp
            530             535             540

His Thr Lys Val Asn Ser Lys Leu Ser Leu Phe Phe Glu Ile Lys Ser
545             550             555             560
```

<210> SEQ ID NO 12
<211> LENGTH: 545
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
```

```
              355                 360                 365
Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415

Ser Ser Thr Lys Lys Thr Gln Leu Gln Leu Glu His Leu Leu Leu Asp
            420                 425                 430

Leu Gln Met Ile Leu Asn Gly Ile Asn Asn Tyr Lys Asn Pro Lys Leu
        435                 440                 445

Thr Arg Met Leu Thr Phe Lys Phe Tyr Met Pro Lys Lys Ala Thr Glu
    450                 455                 460

Leu Lys His Leu Gln Cys Leu Glu Glu Glu Leu Lys Pro Leu Glu Glu
465                 470                 475                 480

Val Leu Asn Leu Ala Gln Ser Lys Asn Phe His Leu Arg Pro Arg Asp
                485                 490                 495

Leu Ile Ser Asn Ile Asn Val Ile Val Leu Glu Leu Lys Gly Ser Glu
            500                 505                 510

Thr Thr Phe Met Cys Glu Tyr Ala Asp Glu Thr Ala Thr Ile Val Glu
        515                 520                 525

Phe Leu Asn Arg Trp Ile Thr Phe Cys Gln Ser Ile Ile Ser Thr Leu
    530                 535                 540

Thr
545

<210> SEQ ID NO 13
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
            85                  90                  95

Asp Asn Ala Glu Thr Ile Lys Lys Glu Leu Gly Leu Ser Leu Thr Glu
        100                 105                 110

Pro Leu Met Glu Gln Val Gly Thr Glu Glu Phe Ile Lys Arg Phe Gly
    115                 120                 125

Asp Gly Ala Ser Arg Val Val Leu Ser Leu Pro Phe Ala Glu Gly Ser
130                 135                 140

Ser Ser Val Glu Tyr Ile Asn Asn Trp Glu Gln Ala Lys Ala Leu Ser
145                 150                 155                 160
```

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr
        515                 520

<210> SEQ ID NO 14
<211> LENGTH: 545
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

-continued

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415
```

```
Ser Ser Thr Lys Lys Thr Gln Leu Gln Leu Glu His Leu Leu Asp
            420                 425                 430

Leu Gln Met Ile Leu Asn Gly Ile Asn Asn Tyr Lys Asn Pro Lys Leu
        435                 440                 445

Thr Arg Met Leu Thr Phe Lys Phe Tyr Met Pro Lys Lys Ala Thr Glu
        450                 455                 460

Leu Lys His Leu Gln Cys Leu Glu Glu Glu Leu Lys Pro Leu Glu Glu
465                 470                 475                 480

Val Leu Asn Leu Ala Gln Ser Lys Asn Phe His Leu Arg Pro Arg Asp
                485                 490                 495

Leu Ile Ser Asn Ile Asn Val Ile Val Leu Glu Leu Lys Gly Ser Glu
                500                 505                 510

Thr Thr Phe Met Cys Glu Tyr Ala Asp Glu Thr Ala Thr Ile Val Glu
        515                 520                 525

Phe Leu Asn Arg Trp Ile Thr Phe Cys Gln Ser Ile Ile Ser Thr Leu
        530                 535                 540

Thr
545

<210> SEQ ID NO 15
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220
```

```
Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
    275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
            325                 330                 335

Ser Leu Met Val Ala Gln Ala Ile Pro Leu Val Gly Glu Leu Val Asp
        340                 345                 350

Ile Gly Phe Ala Ala Tyr Asn Phe Val Glu Ser Ile Ile Asn Leu Phe
    355                 360                 365

Gln Val Val His Asn Ser Tyr Asn Arg Pro Ala Tyr Ser Pro Gly His
370                 375                 380

Lys Thr His Ala Pro Thr Ser Ser Thr Lys Lys Thr Gln Leu Gln
385                 390                 395                 400

Leu Glu His Leu Leu Leu Asp Leu Gln Met Ile Leu Asn Gly Ile Asn
            405                 410                 415

Asn Tyr Lys Asn Pro Lys Leu Thr Arg Met Leu Thr Phe Lys Phe Tyr
        420                 425                 430

Met Pro Lys Lys Ala Thr Glu Leu Lys His Leu Gln Cys Leu Glu Glu
    435                 440                 445

Glu Leu Lys Pro Leu Glu Glu Val Leu Asn Leu Ala Gln Ser Lys Asn
450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
            485                 490                 495

Glu Thr Ala Thr Ile Val Glu Phe Leu Asn Arg Trp Ile Thr Phe Cys
        500                 505                 510

Gln Ser Ile Ile Ser Thr Leu Thr
            515                 520

<210> SEQ ID NO 16
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Ala Asp Asp Val Ala Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
```

```
                50                  55                  60
Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
                115                 120                 125

Gly Asp Gly Ala Ser Arg Val Val Leu Ser Leu Pro Phe Ala Glu Gly
                130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
                195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
                370                 375                 380

His Lys Thr His Ala Pro Thr Ser Ser Thr Lys Lys Thr Gln Leu
385                 390                 395                 400

Gln Leu Glu His Leu Leu Leu Asp Leu Gln Met Ile Leu Asn Gly Ile
                405                 410                 415

Asn Asn Tyr Lys Asn Pro Lys Leu Thr Arg Met Leu Thr Phe Lys Phe
                420                 425                 430

Tyr Met Pro Lys Lys Ala Thr Glu Leu Lys His Leu Leu Gln Cys Leu
                435                 440                 445

Glu Glu Glu Leu Lys Pro Leu Glu Glu Val Leu Asn Leu Ala Gln Ser
                450                 455                 460

Lys Asn Phe His Leu Arg Pro Arg Asp Leu Ile Ser Asn Ile Asn Val
465                 470                 475                 480
```

```
Ile Val Leu Glu Leu Lys Gly Ser Glu Thr Thr Phe Met Cys Glu Tyr
                485                 490                 495

Ala Asp Glu Thr Ala Thr Ile Val Glu Phe Leu Asn Arg Trp Ile Thr
            500                 505                 510

Phe Cys Gln Ser Ile Ile Ser Thr Leu Thr
            515                 520

<210> SEQ ID NO 17
<211> LENGTH: 535
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
```

```
            305                 310                 315                 320
Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
                355                 360                 365

Gln Val Val His Asn Ser Tyr Asn Arg Pro Ala Tyr Ser Pro Gly His
                370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
                420                 425                 430

Leu Leu Pro Thr Ile Pro Gly Lys Leu Asp Val Asn Lys Ser Lys Thr
                435                 440                 445

His Ile Ser Val Asn Gly Arg Lys Ile Arg Met Arg Cys Arg Ala Ile
                450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
                500                 505                 510

Gly Tyr Gln Lys Thr Val Asp His Thr Lys Val Asn Ser Lys Leu Ser
                515                 520                 525

Leu Phe Phe Glu Ile Lys Ser
                530                 535

<210> SEQ ID NO 18
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
                20                  25                  30

Ser Ser Lys Ser Phe Val Met Glu Asn Phe Ser Ser Tyr His Gly Thr
                35                  40                  45

Lys Pro Gly Tyr Val Asp Ser Ile Gln Lys Gly Ile Gln Lys Pro Lys
                50                  55                  60

Ser Gly Thr Gln Gly Asn Tyr Asp Asp Asp Trp Lys Glu Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
                100                 105                 110

Leu Thr Lys Val Leu Ala Leu Lys Val Asp Asn Ala Glu Thr Ile Lys
                115                 120                 125
```

```
Lys Glu Leu Gly Leu Ser Leu Thr Glu Pro Leu Met Glu Gln Val Gly
            130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
                195                 200                 205

Gln Ala Cys Ala Gly Asn Arg Val Arg Arg Ser Val Gly Ser Ser Leu
210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
                275                 280                 285

Lys Thr Val Thr Gly Thr Asn Pro Val Phe Ala Gly Ala Asn Tyr Ala
290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
                340                 345                 350

Ile Val Ala Gln Ser Ile Ala Leu Ser Ser Leu Met Val Ala Gln Ala
                355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
                420                 425                 430

Thr Gly Phe Gln Gly Glu Ser Gly His Asp Ile Lys Ile Thr Ala Glu
                435                 440                 445

Asn Thr Pro Leu Pro Ile Ala Gly Val Leu Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
                500                 505                 510

His Val Ala Phe His Arg Ser Ser Glu Lys Ile His Ser Asn Glu
                515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
```

<210> SEQ ID NO 19
<211> LENGTH: 535
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Gly Ala Asp Asp Val Asp Ser Ser Lys Ser Phe Val Met Glu Asn
1               5                   10                  15

Phe Ser Ser Tyr His Gly Thr Lys Pro Gly Tyr Val Asp Ser Ile Gln
                20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350
```

```
Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
    370                 375                 380

Lys Thr Gln Pro Phe Phe His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
            450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Phe Lys Leu Ser
            515                 520                 525

Leu Phe Phe Glu Ile Lys Ser
            530                 535

<210> SEQ ID NO 20
<211> LENGTH: 560
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
            115                 120                 125

Lys Glu Leu Gly Leu Ser Leu Thr Glu Pro Leu Met Glu Gln Val Gly
        130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175
```

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
            245                 250                 255

Glu Ser Pro Asn Lys Thr Val Ser Glu Glu Lys Ala Lys Gln Tyr Leu
        260                 265                 270

Glu Glu Phe His Gln Thr Ala Leu Glu His Pro Glu Leu Ser Glu Leu
    275                 280                 285

Lys Thr Val Thr Gly Thr Asn Pro Val Phe Ala Gly Ala Asn Tyr Ala
            290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
            325                 330                 335

Ser Val Met Gly Ile Ala Asp Gly Ala Val His His Asn Thr Glu Glu
        340                 345                 350

Ile Val Ala Gln Ser Ile Ala Leu Ser Ser Leu Met Val Ala Gln Ala
    355                 360                 365

Ile Pro Leu Val Gly Glu Leu Val Asp Ile Gly Phe Ala Ala Tyr Asn
            370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Phe His
            405                 410                 415

Asp Gly Tyr Ala Val Ser Trp Asn Thr Val Glu Asp Ser Ile Ile Arg
        420                 425                 430

Thr Gly Phe Gln Gly Glu Ser Gly His Asp Ile Lys Ile Thr Ala Glu
    435                 440                 445

Asn Thr Pro Leu Pro Ile Ala Gly Val Leu Leu Pro Thr Ile Pro Gly
            450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
            485                 490                 495

Arg Pro Lys Ser Pro Val Tyr Val Gly Asn Gly Val His Ala Asn Leu
        500                 505                 510

His Val Ala Phe His Arg Ser Ser Glu Lys Ile His Ser Asn Glu
    515                 520                 525

Ile Ser Ser Asp Ser Ile Gly Val Leu Gly Tyr Gln Lys Thr Val Asp
            530                 535                 540

His Thr Lys Val Asn Phe Lys Leu Ser Leu Phe Phe Glu Ile Lys Ser
545                 550                 555                 560

<210> SEQ ID NO 21
<211> LENGTH: 6402
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 21

```
ggcgagtgct ttgaatgctt gggcttcttc acggcgggtc ttgaccgcgt tgataagttc      60
gcggccagag ctgaattgct ggcgtggggt ggggttgaac tggtcgtgtc ctgccatatc     120
ccttacctgc tttatcaagt ctccaaggcg catcacccgg ttgtgctgcc tataccaacg     180
ataagcggta ggggctttgc ctgtgtagaa cgggttgcgg ctaaagcggt gggaaaagtg     240
cgggtcatgg tctaaaagct cacccagcac acgcgtggtt gctgcaagaa gcttcatctg     300
cgcagattta ccgttacggt cagcgtagac agggtcaata agccatatga actgggcttt     360
gccgttagtt gggttaatac ccacccaggc tggcccgacg ctatgagtaa tcagtgagcg     420
caccacgtcg cggacgtacg ggtttaagtc tgcggggtca ccgcctgcgg tacctacttg     480
gtcaacgtct acgaccagga cggcggcgta ctgcttggtg gtgagcatgg cgtactcgca     540
ccgtcctaaa gcatcagtct cgaagcgata catacgcggc gagttcgtgc cgtcagcgtt     600
gcgtcgatag gccttttttaa agtctcgtgt gactgaaccg tggagtacat cgcggcctag     660
atgatcgcgt aaaaggtcgc ggtcactggc agatgctggg gtgttgtcca gtccaccacg     720
gtcgcgctcg acgcgggtag gtgttttagt gtgcgcattc tgcgcatgag tctgtaaact     780
catgaccgtg ctttctccca ggtgtgtgct gggtgataag cgaaagtcat cgggttgccg     840
cccggtggct ttcttcgttt ttcattgtct ttccctgact ctaaatgaca ccggtgttat     900
ttactagcca tgacacgcga aaaatatgcc ttttacctgc ggttacgtat ggctagacat     960
atggcaagct atacgtaacc gcgtttcagc tgcacagggc tgtctgcgca gatttaccat    1020
cacgggactt ttcccagttc aggctgcgca tatttacgca tacaacgaaa gcggttgcgc    1080
agatttacca cacactctgc gctgatttac cgatacgcag aaaaagcgtg cgcagattta    1140
cccatacggt ggcgaattat ccagagcaat aggtatacag caatacagta atacaggtgc    1200
cataaacctg tattactgta ttgctgtatg cctgtaaacc tttatttatt gttgtggacg    1260
tattcttcga ggtaggtgct aacaatctcg cggatggtca cgccttttg ggcggcgatg    1320
actttaagtt ctgcgtgaag gtcgcggtcg atttcaatcg tcatcttctt gacgtagtcg    1380
cggcctgtgg gttggtggaa tgcgcttcgc actgttttct tctcggctgc tggagttagc    1440
ttcgtggctt ttttcattga ggttcgcggg ccttgctgcg ccctggcgcg ttctttactg    1500
gtgctcattt catcatctcc atgagttcgt cggcgacgtg gtcgtagccg tgcatgtcgg    1560
ggcctgggca gtatccaaac gctaggtgca tatcttcgcg tagcgggatt tcggttttaa    1620
agtgcggcat gtgttccgcg tcgagcgctt ctcgtgccgc gtcaagggcg ctggtgcctt    1680
tcctggcgaa cgtcagtaag actgcatgag gtgttccgtt gactgcgtcg cgcagctccc    1740
atactcggga gaggtcggca gcagcagaac gggtcggaag aatgatgaag tcgctgactg    1800
cgattgctgc ttcgatagcg ttctcgtctc ctggcggcac atcgataccg actgggcgat    1860
ggcccactac gtgaaccatc accctaatca agttttttgg ggtcgaggtg ccgtaaagca    1920
ctaaatcgga accctaaagg gagcccccga tttagagctt gacggggaaa gccggcgaac    1980
gtggcgagaa aggaagggaa gaaagcgaaa ggagcgggcg ctagggcgct ggcaagtgta    2040
gcggtcacgc tgcgcgtaac caccacaccc gccgcgctta atgcgccgct acagggcgct    2100
cccattcgcc attcaggctg cgcaactgtt gggaagggcg atcggtgcgg gcctcttcgc    2160
tattacgcca gctggcgaaa gggggatgtg ctgcaaggcg attaagttgg gtaacgccag    2220
```

```
ggttttccca gtcacgacgt tgtaaaacga cggccagtga attgtaatac gactcactat    2280
agggcgaatt ggagctccac cgcggtggcg gccgctctag aactagtgga tccagggcat    2340
tgatttcaga gcacccttat aattaggata gctaagtcca ttattttatg agtcctggta    2400
aggggatacg ttgtgagcag aaaactgttt gcgtcaatct taatagggcc gctactgggg    2460
atagggcccc accttcagc ccatgcaggc gctgatgatg ttgttgattc ttctaaatct    2520
tttgtgatgg aaaacttttc ttcgtaccac gggactaaac ctggttatgt agattccatt    2580
caaaaaggta tacaaaagcc aaaatctggt acacaaggaa attatgacga tgattggaaa    2640
gggttttata gtaccgacaa taaatacgac gctgcgggat actctgtaga taatgaaaac    2700
ccgctctctg gaaaagctgg aggcgtggtc aaagtgacgt atccaggact gacgaaggtt    2760
ctcgcactaa aagtggataa tgccgaaact attaagaaag agttaggttt aagtctcact    2820
gaaccgttga tggagcaagt cggaacggaa gagtttatca aaaggttcgg tgatggtgct    2880
tcgcgtgtag tgctcagcct tcccttcgct gagggagtt ctagcgttga atatattaat    2940
aactgggaac aggcgaaagc gttaagcgta gaacttgaga ttaattttga acccgtgga    3000 aaacgtggcc aagatgcgat gtatgagtat atggctcaag cctgtgcagg aaatcgtgtc    3060
aggcgatcag taggtagctc attgtcatgc atcaacctgg attgggatgt tatccgtgat    3120
aaaactaaaa ctaagatcga atctctgaaa gaacacggtc cgatcaaaaa caaaatgagc    3180
gaaagcccga caaaactgt atctgaagaa aagctaaac agtacctgga gaattccac    3240 cagactgcac tggaacaccc ggaactgtct gaacttaaga ccgttactgg taccaacccg    3300
gtattcgctg gtgctaacta cgctgcttgg gcagtaaacg ttgctcaggt tatcgatagc    3360
gaaactgctg ataacctgga aaaaactacc gcggctctgt ctatcctgcc gggtatcggt    3420
agcgtaatgg gcatcgcaga cggcgccgtt caccacaaca ctgaagaaat cgttgcacag    3480
tctatcgctc tgagctctct gatggttgct caggccatcc cgctggtagg tgaactggtt    3540
gatatcggtt tcgctgcata caacttcgtt gaaagcatca tcaacctgtt ccaggttgtt    3600
cacaactctt acaaccgccc ggcttactct ccgggtcaca agacgcatgc acctacttct    3660
agctctacca agaaaaccca gctgcagctc gagcacctgc tgctggattt gcagatgatc    3720
ctgaacggta tcaacaatta caagaacccg aaactgacgc gtatgctgac cttcaagttc    3780
tacatgccga agaaggccac cgaactgaaa cacctgcagt gtctagaaga agaactgaaa    3840
ccgctggagg aagttctgaa cctggctcag tctaaaaact tccacctgcg gccgcgtgac    3900
ctgatctcta acatcaacgt aatcgttctg gaactgaagg gctctgaaac caccttcatg    3960
tgtgaatacg ctgatgagac cgcaaccatc gtagaattcc tgaaccgttg gatcaccttc    4020
tgtcagtcta tcatctctac cctgacctga ggatccccccg ggctgcagga attcgatatc    4080
aagcttatcg ataccgtcga cctcgagggg gggcccggta ccagcttttg ttcccttag    4140 tgagggttaa tttcgagctt ggcgtaatca tggtcatagc tgtttcctgt gtgaaattgt    4200
tatccgctca caattccaca acatacga gccggaagca taaagtgtaa agcctggggt    4260
gcctaatgag tgagtccccg atccgtcgag ctcgacctgc aggggggggg gggcgctgag    4320
gtctgcctcg tgaagaaggt gttgctgact cataccaggc ctgaatcgcc ccatcatcca    4380
gccagaaagt gagggagcca cggttgatga gagctttgtt gtaggtggac cagttggtga    4440
ttttgaactt tgctttgcc acggaacggt ctgcgttgtc gggaagatgc gtgatctgat    4500
ccttcaactc agcaaaagtt cgatttattc aacaaagccg ccgtcccgtc aagtcagcgt    4560
aatgctctgc cagtgttaca accaattaac caattctgat tagaaaaact catcgagcat    4620
```

```
caaatgaaac tgcaatttat tcatatcagg attatcaata ccatattttt gaaaaagccg    4680
tttctgtaat gaaggagaaa actcaccgag gcagttccat aggatggcaa gatcctggta    4740
tcggtctgcg attccgactc gtccaacatc aatacaacct attaatttcc cctcgtcaaa    4800
aataaggtta tcaagtgaga atcaccatg agtgacgact gaatccggtg agaatggcaa    4860
aagcttatgc atttctttcc agacttgttc aacaggccag ccattacgct cgtcatcaaa    4920
atcactcgca tcaaccaaac cgttattcat tcgtgattgc gcctgagcga gacgaaatac    4980
gcgatcgctg ttaaaaggac aattacaaac aggaatcgaa tgcaaccggc gcaggaacac    5040
tgccagcgca tcaacaatat tttcacctga atcaggatat tcttctaata cctggaatgc    5100
tgttttcccg gggatcgcag tggtgagtaa ccatgcatca tcaggagtac ggataaaatg    5160
cttgatggtc ggaagaggca taaattccgt cagccagttt agtctgacca tctcatctgt    5220
aacatcattg gcaacgctac ctttgccatg tttcagaaac aactctggcg catcgggctt    5280
cccatacaat cgatagattg tcgcacctga ttgcccgaca ttatcgcgag cccatttata    5340
cccatataaa tcagcatcca tgttggaatt taatcgcggc ctcgagcaag acgtttcccg    5400
ttgaatatgg ctcataacac cccttgtatt actgtttatg taagcagaca gttttattgt    5460
tcatgatgat atatttttat cttgtgcaat gtaacatcag agattttgag acacaacgtg    5520
gctttccccc cccccctgc aggtcgagct cgacggatcg ggctgcagga attcggtgag    5580
gttatggcgg agggttgcga ggtctaggag aacagaggaa gtcatgcttt gaagcatata    5640
agctgccctg cccctcaagg ttttcttcaa gtgaggtttt atctaactgc ctaacggcag    5700
gggaaccgta tattgcttac ggtatgagac cccttaaacg tccggatagt caccgctctt    5760
ctttagctcc gcgacatgcc tagcaaccgt ggcgcgagag actcctacct ctgcccctat    5820
ttcagcccac gtgggaactg tccctgtctg gaaatactga tcgttcacca tttggctaat    5880
acgggacttc gtagatcgtc cttgagcctt tttcttacgg tgcgtctttt caagcttcga    5940
cctttgtgct tgcgcatatt tgccctcggg gtctgttttc cagcgttgtg cggctttttg    6000
tccgcctctg cgtcccatcg tggccaaggc tttccgctcg ctgctggtgg ctttacctgg    6060
tgcgttagag ccgctgtagg tctcgctctt ggattgggcg acatacccgc gcacgcgcct    6120
tgccatggtt tggcggtcgc gcatgggtgg catctcgttg tcgcggcctg caccgccgtg    6180
ggtgtgtgcg acgttgtagg cgtgctcata ggcgtcgatg attgctgcgt ctgtcaggcg    6240
ttggccttgc tggcgcaagc ggtggccagt cttaagcgca tgtctaaagg ctgtttcgtc    6300
gcgtgctgcg gttccttgga caatccagag cacacgcaca ccgtcgataa gttccgggtc    6360
atactggtcg agaccaccgg cgatttccgc gtctacgtcc tg                       6402
```

<210> SEQ ID NO 22
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Ser Arg Lys Leu Phe Ala Ser Ile Leu Ile Gly Ala Leu Leu Gly
1               5                   10                  15

Ile Gly Ala Pro Pro Ser Ala His Ala
            20                  25

```
<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Tyr Lys Asp Asp Asp Asp Lys
1               5

<210> SEQ ID NO 25
<211> LENGTH: 19
<212> TYPE: DNA
<213> ORGANISM: Unknown
<220> FEATURE:
<223> OTHER INFORMATION: Description of Unknown:
      wild-type toxO sequence

<400> SEQUENCE: 25
ttaggatagc tttacctaa                                                  19

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val
            20                  25                  30

<210> SEQ ID NO 28
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 28

Met Gly Ala Asp Asp
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Asp Asp
1

<210> SEQ ID NO 30
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240
```

Glu Lys Ala Lys Gln Tyr Leu Glu Glu Phe His Gln Thr Ala Leu Glu
            245                 250                 255

His Pro Glu Leu Ser Glu Leu Lys Thr Val Thr Gly Thr Asn Pro Val
        260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
        500                 505                 510

Gln Ser Ile Ile Ser Thr Leu Thr Glu Asn Leu Tyr Phe Gln
    515                 520                 525

<210> SEQ ID NO 31
<211> LENGTH: 1686
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gtgagcagaa aactgtttgc gtcaatctta atagggcgc tactggggat aggggcccca      60
ccttcagccc atgcaggcgc tgatgatgtt gctgattctt ctaaatcttt tgtgatggaa     120 aactttttctt cgtaccacgg gactaaacct ggttatgtag attccattca aaaaggtata    180
caaaagccaa atctggtac acaaggaaat tatgacgatg attggaagg gttttatagt      240 accgacaata aatacgacgc tgcgggatac tctgtagata tgaaaacccc gctctctgga   300
aaagctggag gcgtggtcaa agtgacgtat ccaggactga cgaaggttct cgcactaaaa    360
gtggataatg ccgaaactat taagaaagag ttaggtttaa gtctcactga accgttgatg    420

-continued

```
gagcaagtcg gaacggaaga gtttatcaaa aggttcggtg atggtgcttc gcgtgtagtg    480
ctcagccttc ccttcgctga ggggagttct agcgttgaat atattaataa ctgggaacag    540
gcgaaagcgt taagcgtaga acttgagatt aattttgaaa cccgtggaaa acgtggccaa    600
gatgcgatgt atgagtatat ggctcaagcc tgtgcaggaa atcgtgtcag gcgatcagta    660
ggtagctcat tgtcatgcat caacctggat tgggatgtta tccgtgataa aactaaaact    720
aagatcgaat ctctgaaaga acacggtccg atcaaaaaca aaatgagcga aagcccgaac    780
aaaactgtat ctgaagaaaa agctaaacag tacctggaag aattccacca gactgcactg    840
gaacacccgg aactgtctga acttaagacc gttactggta ccaacccggt attcgctggt    900
gctaactacg ctgcttgggc agtaaacgtt gctcaggtta tcgatagcga aactgctgat    960
aacctggaaa aaactaccgc ggctctgtct atcctgccgg gtatcggtag cgtaatgggc   1020
atcgcagacg gcgccgttca ccacaacact gaagaaatcg ttgcacagtc tatcgctctg   1080
agctctctga tggttgctca ggccatcccg ctggtaggtg aactggttga tatcggtttc   1140
gctgcataca acttcgttga aagcatcatc aacctgttcc aggttgttca caactcttac   1200
aaccgcccgg cttactctcc gggtcacaag acgcatgcac ctacttctag ctctaccaag   1260
aaaacccagc tgcagctcga gcacctgctg ctggatttgc agatgatcct gaacggtatc   1320
aacaattaca agaacccgaa actgacgcgt atgctgacct tcaagttcta catgccgaag   1380
aaggccaccg aactgaaaca cctgcagtgt ctagaagaag aactgaaacc gctggaggaa   1440
gttctgaacc tggctcagtc taaaaacttc cacctgcggc cgcgtgacct gatctctaac   1500
atcaacgtaa tcgttctgga actgaagggc tctgaaacca ccttcatgtg tgaatacgct   1560
gatgagaccg caaccatcgt agaattcctg aaccgttgga tcaccttctg tcagtctatc   1620
atctctaccc tgaccgagaa cctgtacttc cagggccatc accaccacca ccaccatcat   1680
cactag                                                              1686
```

<210> SEQ ID NO 32
<211> LENGTH: 250
<212> TYPE: PRT
<213> ORGANISM: Corynebacterium diphtheriae

<400> SEQUENCE: 32

```
Met Arg Lys Ile Val Thr Leu Ala Ala Ala Ser Leu Leu Gly Ile Ala
1               5                   10                  15

Gly Thr Ser Gly Val Leu Gly Ala Ala Thr Ala Thr Ala Leu Thr Asn
            20                  25                  30

Gly Thr Pro Val Ser Pro Glu Asp Asp Thr Ala Ala Glu Gly Val Val
        35                  40                  45

Gln Val Ala Ser Cys Thr Gly Thr Val Val Ala Ser Gln Trp Val Leu
    50                  55                  60

Thr Ala Gln His Cys Val Glu Val Pro Asn Leu Gln Arg Pro Val Tyr
65                  70                  75                  80

Val Gly Thr Thr Arg Glu Gln Gln Gln Arg Glu Glu Asn Thr Phe Thr
                85                  90                  95

Ser Asp Tyr Ala Val Trp Ala Pro His Gly Asp Val Ala Leu Val His
            100                 105                 110

Val Thr Asp Ala Leu Pro Gln Arg Leu Val Arg Ala Val Arg Arg Ala
        115                 120                 125

Pro Val Ser Phe Gly Glu Gln Gly Arg Val Tyr Gly Trp Gly Ala Gly
    130                 135                 140
```

```
Thr Gly Glu Thr Leu Gln Tyr Ala Arg Ala Ala Val Gly Lys Thr Ser
145                 150                 155                 160

Ser Gly Val Arg Pro Gln Gly Asn Gln His Gly Ala Phe Ile Val Gln
                165                 170                 175

Tyr Leu Asp Glu Ala Lys Ala Gly Arg Gly Asp Ser Gly Gly Pro Leu
            180                 185                 190

Phe Val Asn Gly Glu Val Ala Gly Val Thr Ser Phe Lys Ala Pro Gln
        195                 200                 205

Gly Gly Gly Arg Phe Ser Leu Phe Ala Ser Leu His Gly Leu Gly Asp
    210                 215                 220

Trp Ile Ala Gln Thr Thr Ala Ala Lys Pro Glu Asn Pro Asn Ser Lys
225                 230                 235                 240

Asn Gln Gln Ser Gln Gln Pro Arg Arg Pro
                245                 250

<210> SEQ ID NO 33
<211> LENGTH: 753
<212> TYPE: DNA
<213> ORGANISM: Corynebacterium diphtheriae

<400> SEQUENCE: 33
atgcggaaaa ttgttactct tgctgcagca agcttgctgg gtattgcggg taccagcggt      60
gttcttggtg cggcaacagc caccgcactg acaaatggca cgcccgtctc ccctgaggac     120
gataccgctg ccgaaggcgt ggttcaagtg gctagttgta ctggcaccgt ggttgcttct     180
cagtgggtgc tgaccgccca gcattgcgtc gaggtgccca atttgcagcg gccggtctat     240
gttggcacca cccgcgagca gcaacaacgg gaagaaaata cgttcacctc ggattacgca     300
gtgtgggcac cgcacggcga tgtggcgttg gtgcatgtca ccgatgcgct gccgcagcgt     360
ctggtccgcg cggttcgccg cgcaccggtg agctttggtg agcagggacg cgtgtacggc     420
tggggtgctg gcaccggcga gacgctgcag tatgcccgcg ctgcggttgg taaaacttct     480
tccggagttc ggccgcaggg caaccagcat ggtgcattca tcgtgcagta tttggacgag     540
gctaaagccg ggcgtggcga ttccggcggg ccgctttttg tcaacggtga ggttgctggg     600
gtgacctcgt ttaaggctcc tcaaggtggt gggcgtttct cgctgtttgc ttcgctgcat     660
gggctaggcg attggattgc gcagaccacc gccgccaagc ccgagaaccc gaattccaag     720
aatcaacagt cccagcaacc acgtagaccg tag                                  753

<210> SEQ ID NO 34
<211> LENGTH: 1012
<212> TYPE: DNA
<213> ORGANISM: Corynebacterium diphtheriae

<400> SEQUENCE: 34
ggatccgcaa ttgcgggaat cgtcgtgctt tttagccgaa attttcttgc agccagcgct      60
atgcttatcg cctcagggtt agccgctgac atttaccgct tgaggaataa tatgagtgga     120
aatcaacggt aatttcagaa gacttgccta cacctttagc tagcgaccac cattggtggt     180
cgctagcttt ttgatggctt aagggacatt tgggcatccg tgtatcgcac attagtcata     240
caggaaatcc tccaagattt cgtccgcatg cccgaccaga cactacagca cccacatagc     300
ttctcgattg tcttgcggag cgggagtagg tagctcacgt gctaccgcac ggggaaccgt     360
atattgctta tggtgtgccc attacccacc gttggtgcta tgatccgaac ggaaaaagtc     420
agtcgtatta gtgaatcacc gttccgccgc gcgagaacgc agggctccaa caagcgtgtg     480
```

```
gttccacaag attgcaagga tgtgtacggt gctggtggcg gtggctccag cctgggtctg    540
tcgtcttctt agcaagtctg cattcacggt tccctaggca atctttgagc aaatccctgt    600
ttaacgcccc tgtacgttcg gcgccgcaga acctgccgg atcgtgatgt taatcctgcc     660
ttgttccagc ccgcagccgt cgggaagcgt ggcatcattc acgcgcacca ccccgtgata    720
agcaaaacgc ttcggcccac cgaaaaccac caagtcgccg gagcacagag tcacatcgtc    780
ccagggttgg gtgcgtgatt cggtgtgtcc catccgaaac agtgcttcgt cgccaatcga    840
tactgaaatg accggcgccc gcgattcctc aaattcatcg acgtgcatgc ccatcccgga    900
acccggcgga tagtagttga ccagcaccat ctctgtcacg aaggcctcta cccacggggc    960
tagttcttcg gcaacctccg ctgctgcgcg caacgctgcc ggcgccggat cc           1012
```

<210> SEQ ID NO 35
<211> LENGTH: 242
<212> TYPE: PRT
<213> ORGANISM: Corynebacterium diphtheriae

<400> SEQUENCE: 35

```
Met Lys Lys Leu Arg Thr Leu Ala Val Thr Leu Thr Ala Ile Ala Ala
1               5                   10                  15

Ser Thr Met Ala Thr Met Pro Ala Gln Ala Val Ile Ser Pro Thr Pro
                20                  25                  30

Ser His Gln Val Ser Leu Ala Tyr Val Ser Phe Asp Asn Met Gln Cys
            35                  40                  45

Thr Gly Thr Leu Val Ser Pro Thr Ala Val Leu Thr Ala Arg His Cys
        50                  55                  60

Leu Asn Gly Gly Leu Gly His Val Arg Leu Gly Ala Asp His Phe Thr
65                  70                  75                  80

Ala Val Arg Ala Val Ala His Pro Gln Ala Asp Leu Ala Val Leu His
                85                  90                  95

Leu Asp Arg Pro Ala Pro Ile Ala Pro Ser Ala Ile Ser Gly Arg His
            100                 105                 110

Thr Gln Pro Gly Asn Arg Phe Gly Val Ala Gly Tyr Gly Ser Thr Phe
        115                 120                 125

Thr Gly Ile Pro Met Ala Ala Ala Thr Met Gln Arg Arg Val Thr
    130                 135                 140

Asp Val Pro Ser Pro Asp Arg Gln Ala Val Met Ile Glu Asn His Ile
145                 150                 155                 160

Ser Gln Gly Val Leu Arg Pro Gly Asp Ser Gly Gly Pro Leu Leu Glu
                165                 170                 175

Gly Asn His Val Ile Gly Val Leu Ser Met Ser Ser Ala Ser Gly Arg
            180                 185                 190

Val Gly Trp Tyr Ile Pro Thr Ala Glu His Ala Asp Trp Ile Ala Ala
        195                 200                 205

Ala Ala Gly Ile Pro Ala Pro Gly Ser Val Asp Lys Pro Ala Pro Leu
    210                 215                 220

Val Asp Ala Thr Ala Phe Pro Thr Gln Glu Pro Ser Leu Ala Ser Leu
225                 230                 235                 240

Ser Ser
```

<210> SEQ ID NO 36
<211> LENGTH: 729
<212> TYPE: DNA
<213> ORGANISM: Corynebacterium diphtheriae

<400> SEQUENCE: 36
atgaagaaac ttcgtaccct agccgtaacc ctgaccgcaa tcgcagcatc aaccatggcg 60
accatgccag cacaagcagt gattagtccg acaccgtcac atcaagtttc gctagcgtac 120
gtcagttttg acaacatgca gtgcaccggc acactcgtca gccccaccgc cgtgctcaca 180
gcacgacact gcctcaacgg cggcctcggc cacgtccgac tcggcgccga tcacttcacc 240
gccgtacgtg ccgtggcaca cccccaagca gaccttgccg tcctccacct cgatcgccca 300
gcgccaatag cgccatccgc aatctctgga cgtcacaccc aaccaggtaa ccgcttcgga 360
gttgccggct acggaagcac cttcaccggc atccccatgg cagcagctgc aaccatgcaa 420
cgccgcgtca ccgacgtccc cagccccgac cgccaagcag tcatgatcga aaaccacatc 480
agccaaggtg tactacgccc aggcgactct ggcggccccc tcctagaggg caatcacgtc 540
ataggagtac tcagcatgag cagtgcatcc ggccgcgtcg gctggtacat ccccaccgca 600
gaacacgccg actggatcgc ggcggcagcc ggaatccccg caccgggaag cgtcgacaag 660
cccgctccgc tcgtcgacgc cacagccttc ccgacgcaag agccaagcct cgctagccta 720
tcctcctag 729

<210> SEQ ID NO 37
<211> LENGTH: 1012
<212> TYPE: DNA
<213> ORGANISM: Corynebacterium diphtheriae

<400> SEQUENCE: 37
ggatccgggc ttatcaccgc agaagacgcc gaaaaagcca tcgatgccac cctcctagcc 60
gtcgacggca tcacacgcca taacgacgac cccatggcat ggctcgccgc tatgggatac 120
ccactaacat gggcaaaaaa catcacgctt aaggaggccg aatgattacc gtctatcaca 180
acccccgctg ctccacctcg cgcaaagcct tggagtacat agaacaacac agcgacgacg 240
aggtgaccat catccgctac ctcgacgccc ctcctagtga acaagagctg cgcactttgc 300
ttgccgacgc ccacctcagc ccgcacgacg caatccgcac caaagaagcc gaatacaaag 360
aactcggact cagctccacc acccccgaat cagagctaat caaggccatg gtcacccacc 420
cacgcctcat tcagcgccca attgtggcaa catgcaaggg aacgcggatc gcccgaccaa 480
ccgaaattct gaaagaaatt ctctagccga atcgccagcg atctcggaag ccaaggaatc 540
cttcggcatg ttaaaaaatg taaaagttta atgcgggcac aaacgcgttg aaagagcaac 600
acaccaccat cgttgaacat acttgattat ttcccacttt ccagaatttt aatgagcatg 660
cccagctcga catcaagaac gcagggaaga tctcactagc aatcgacgat aggcccttct 720
tcgacaaccc ggaacatctt gccacgtacg acggaactac actggcagga tcgtcaatat 780
gtggtgaatt ccctgttaaa gtaggaagaa cagagggtgt cagtccgttt gtgtacgggg 840
actgacaccc tctgttcaaa tgattcatcg aagacggttt cacttttcta gcaaaacagc 900
aagacccgca agatttcata tattggtcaa gcgcagccac aaactatcac tcatagctat 960
gtagccccct attaattcat atctcaaaga gtatccaagc actttgggat cc 1012

<210> SEQ ID NO 38
<211> LENGTH: 558
<212> TYPE: PRT
<213> ORGANISM: Artificial Sequence
<220> FEATURE:
<223> OTHER INFORMATION: Description of Artificial Sequence: Synthetic
polypeptide

```
-continued

<400> SEQUENCE: 38

Met Ser Arg Lys Leu Phe Ala Ser Ile Leu Ile Gly Ala Leu Leu Gly
1               5                   10                  15

Ile Gly Ala Pro Pro Ser Ala His Ala Met His His His His His His
            20                  25                  30

Glu Asn Leu Tyr Phe Gln Gly Ala Asp Asp Val Ala Asp Ser Ser Lys
        35                  40                  45

Ser Phe Val Met Glu Asn Phe Ser Ser Tyr His Gly Thr Lys Pro Gly
    50                  55                  60

Tyr Val Asp Ser Ile Gln Lys Gly Ile Gln Lys Pro Lys Ser Gly Thr
65                  70                  75                  80

Gln Gly Asn Tyr Asp Asp Asp Trp Lys Gly Phe Tyr Ser Thr Asp Asn
                85                  90                  95

Lys Tyr Asp Ala Ala Gly Tyr Ser Val Asp Asn Glu Asn Pro Leu Ser
            100                 105                 110

Gly Lys Ala Gly Gly Val Val Lys Val Thr Tyr Pro Gly Leu Thr Lys
        115                 120                 125

Val Leu Ala Leu Lys Val Asp Asn Ala Glu Thr Ile Lys Lys Glu Leu
    130                 135                 140

Gly Leu Ser Leu Thr Glu Pro Leu Met Glu Gln Val Gly Thr Glu Glu
145                 150                 155                 160

Phe Ile Lys Arg Phe Gly Asp Gly Ala Ser Arg Val Val Leu Ser Leu
                165                 170                 175

Pro Phe Ala Glu Gly Ser Ser Val Glu Tyr Ile Asn Asn Trp Glu
            180                 185                 190

Gln Ala Lys Ala Leu Ser Val Glu Leu Glu Ile Asn Phe Glu Thr Arg
    195                 200                 205

Gly Lys Arg Gly Gln Asp Ala Met Tyr Glu Tyr Met Ala Gln Ala Cys
210                 215                 220

Ala Gly Asn Arg Val Arg Arg Ser Val Gly Ser Ser Leu Ser Cys Ile
225                 230                 235                 240

Asn Leu Asp Trp Asp Val Ile Arg Asp Lys Thr Lys Thr Lys Ile Glu
                245                 250                 255

Ser Leu Lys Glu His Gly Pro Ile Lys Asn Lys Met Ser Glu Ser Pro
            260                 265                 270

Asn Lys Thr Val Ser Glu Glu Lys Ala Lys Gln Tyr Leu Glu Glu Phe
        275                 280                 285

His Gln Thr Ala Leu Glu His Pro Glu Leu Ser Glu Leu Lys Thr Val
    290                 295                 300

Thr Gly Thr Asn Pro Val Phe Ala Gly Ala Asn Tyr Ala Ala Trp Ala
305                 310                 315                 320

Val Asn Val Ala Gln Val Ile Asp Ser Glu Thr Ala Asp Asn Leu Glu
                325                 330                 335

Lys Thr Thr Ala Ala Leu Ser Ile Leu Pro Gly Ile Gly Ser Val Met
            340                 345                 350

Gly Ile Ala Asp Gly Ala Val His His Asn Thr Glu Glu Ile Val Ala
        355                 360                 365

Gln Ser Ile Ala Leu Ser Ser Leu Met Val Ala Gln Ala Ile Pro Leu
    370                 375                 380

Val Gly Glu Leu Val Asp Ile Gly Phe Ala Ala Tyr Asn Phe Val Glu
385                 390                 395                 400

Ser Ile Ile Asn Leu Phe Gln Val Val His Asn Ser Tyr Asn Arg Pro
                405                 410                 415
```

Ala Tyr Ser Pro Gly His Lys Thr His Ala Pro Thr Ser Ser Ser Thr
            420                 425                 430

Lys Lys Thr Gln Leu Gln Leu Glu His Leu Leu Leu Asp Leu Gln Met
            435                 440                 445

Ile Leu Asn Gly Ile Asn Asn Tyr Lys Asn Pro Lys Leu Thr Arg Met
450                 455                 460

Leu Thr Phe Lys Phe Tyr Met Pro Lys Lys Ala Thr Glu Leu Lys His
465                 470                 475                 480

Leu Gln Cys Leu Glu Glu Glu Leu Lys Pro Leu Glu Glu Val Leu Asn
            485                 490                 495

Leu Ala Gln Ser Lys Asn Phe His Leu Arg Pro Arg Asp Leu Ile Ser
            500                 505                 510

Asn Ile Asn Val Ile Val Leu Glu Leu Lys Gly Ser Glu Thr Thr Phe
            515                 520                 525

Met Cys Glu Tyr Ala Asp Glu Thr Ala Thr Ile Val Glu Phe Leu Asn
            530                 535                 540

Arg Trp Ile Thr Phe Cys Gln Ser Ile Ile Ser Thr Leu Thr
545                 550                 555

<210> SEQ ID NO 39
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met His His His His His Glu Asn Leu Tyr Phe Gln Gly Ala Asp
1               5                   10                  15

Asp Val Ala Asp Ser Ser Lys Ser Phe Val Met Glu Asn Phe Ser Ser
            20                  25                  30

Tyr His Gly Thr Lys Pro Gly Tyr Val Asp Ser Ile Gln Lys Gly Ile
            35                  40                  45

Gln Lys Pro Lys Ser Gly Thr Gln Gly Asn Tyr Asp Asp Asp Trp Lys
        50                  55                  60

Gly Phe Tyr Ser Thr Asp Asn Lys Tyr Asp Ala Ala Gly Tyr Ser Val
65                  70                  75                  80

Asp Asn Glu Asn Pro Leu Ser Gly Lys Ala Gly Gly Val Val Lys Val
                85                  90                  95

Thr Tyr Pro Gly Leu Thr Lys Val Leu Ala Leu Lys Val Asp Asn Ala
            100                 105                 110

Glu Thr Ile Lys Lys Glu Leu Gly Leu Ser Leu Thr Glu Pro Leu Met
            115                 120                 125

Glu Gln Val Gly Thr Glu Glu Phe Ile Lys Arg Phe Gly Asp Gly Ala
        130                 135                 140

Ser Arg Val Val Leu Ser Leu Pro Phe Ala Glu Gly Ser Ser Ser Val
145                 150                 155                 160

Glu Tyr Ile Asn Asn Trp Glu Gln Ala Lys Ala Leu Ser Val Glu Leu
                165                 170                 175

Glu Ile Asn Phe Glu Thr Arg Gly Lys Arg Gly Gln Asp Ala Met Tyr
            180                 185                 190

Glu Tyr Met Ala Gln Ala Cys Ala Gly Asn Arg Val Arg Arg Ser Val
            195                 200                 205

Gly Ser Ser Leu Ser Cys Ile Asn Leu Asp Trp Asp Val Ile Arg Asp

```
                210                 215                 220
Lys Thr Lys Thr Lys Ile Glu Ser Leu Lys Glu His Gly Pro Ile Lys
225                 230                 235                 240

Asn Lys Met Ser Glu Ser Pro Asn Lys Thr Val Ser Glu Glu Lys Ala
                245                 250                 255

Lys Gln Tyr Leu Glu Glu Phe His Gln Thr Ala Leu Glu His Pro Glu
            260                 265                 270

Leu Ser Glu Leu Lys Thr Val Thr Gly Thr Asn Pro Val Phe Ala Gly
            275                 280                 285

Ala Asn Tyr Ala Ala Trp Ala Val Asn Val Ala Gln Val Ile Asp Ser
290                 295                 300

Glu Thr Ala Asp Asn Leu Glu Lys Thr Thr Ala Ala Leu Ser Ile Leu
305                 310                 315                 320

Pro Gly Ile Gly Ser Val Met Gly Ile Ala Asp Gly Ala Val His His
                325                 330                 335

Asn Thr Glu Glu Ile Val Ala Gln Ser Ile Ala Leu Ser Ser Leu Met
            340                 345                 350

Val Ala Gln Ala Ile Pro Leu Val Gly Glu Leu Val Asp Ile Gly Phe
            355                 360                 365

Ala Ala Tyr Asn Phe Val Glu Ser Ile Ile Asn Leu Phe Gln Val Val
370                 375                 380

His Asn Ser Tyr Asn Arg Pro Ala Tyr Ser Pro Gly His Lys Thr His
385                 390                 395                 400

Ala Pro Thr Ser Ser Thr Lys Lys Thr Gln Leu Gln Leu Glu His
                405                 410                 415

Leu Leu Leu Asp Leu Gln Met Ile Leu Asn Gly Ile Asn Asn Tyr Lys
            420                 425                 430

Asn Pro Lys Leu Thr Arg Met Leu Thr Phe Lys Phe Tyr Met Pro Lys
            435                 440                 445

Lys Ala Thr Glu Leu Lys His Leu Gln Cys Leu Glu Glu Glu Leu Lys
            450                 455                 460

Pro Leu Glu Glu Val Leu Asn Leu Ala Gln Ser Lys Asn Phe His Leu
465                 470                 475                 480

Arg Pro Arg Asp Leu Ile Ser Asn Ile Asn Val Ile Val Leu Glu Leu
                485                 490                 495

Lys Gly Ser Glu Thr Thr Phe Met Cys Glu Tyr Ala Asp Glu Thr Ala
            500                 505                 510

Thr Ile Val Glu Phe Leu Asn Arg Trp Ile Thr Phe Cys Gln Ser Ile
            515                 520                 525

Ile Ser Thr Leu Thr
            530

<210> SEQ ID NO 40
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30
```

-continued

Lys Gly Ile Gln Lys Pro Lys Ser Gly Thr Gln Gly Asn Tyr Asp Asp
                35                  40                  45

Asp Trp Lys Gly Phe Tyr Ser Thr Asp Asn Lys Tyr Asp Ala Ala Gly
 50                  55                  60

Tyr Ser Val Asp Asn Glu Asn Pro Leu Ser Gly Lys Ala Gly Gly Val
 65                  70                  75                  80

Val Lys Val Thr Tyr Pro Gly Leu Thr Lys Val Leu Ala Leu Lys Val
                 85                  90                  95

Asp Asn Ala Glu Thr Ile Lys Lys Glu Leu Gly Leu Ser Leu Thr Glu
                100                 105                 110

Pro Leu Met Glu Gln Val Gly Thr Glu Glu Phe Ile Lys Arg Phe Gly
                115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
                180                 185                 190

Arg Ser Val Gly Ser Ser Leu Ser Cys Ile Asn Leu Asp Trp Asp Val
    195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
                260                 265                 270

Phe Ala Gly Ala Asn Tyr Ala Ala Trp Ala Val Asn Val Ala Gln Val
            275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
                340                 345                 350

Ile Gly Phe Ala Ala Tyr Asn Phe Val Glu Ser Ile Ile Asn Leu Phe
            355                 360                 365

Gln Val Val His Asn Ser Tyr Asn Arg Pro Ala Tyr Ser Pro Gly His
    370                 375                 380

Lys Thr His Ala Pro Thr Ser Ser Thr Lys Lys Thr Gln Leu Gln Leu
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
                420                 425                 430

Met Pro Lys Lys Ala Thr Glu Leu Lys His Leu Gln Cys Leu Glu Glu
                435                 440                 445

Glu Leu Lys Pro Leu Glu Glu Val Leu Asn Leu Ala Gln Ser Lys Asn

```
                450             455             460
Phe His Leu Arg Pro Arg Asp Leu Ile Ser Asn Ile Asn Val Ile Val
465                 470             475                 480

Leu Glu Leu Lys Gly Ser Glu Thr Thr Phe Met Cys Glu Tyr Ala Asp
            485             490                 495

Glu Thr Ala Thr Ile Val Glu Phe Leu Asn Arg Trp Ile Thr Phe Cys
        500             505             510

Gln Ser Ile Ile Ser Thr Leu Thr
        515             520

<210> SEQ ID NO 41
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gtgagcagaa aactgtttgc gtcaatctta ataggggcgc tactggggat aggggcccca      60
ccttcagccc atgcaatgca tcaccaccac caccacgaga acctgtactt ccagggcgct     120
gatgatgttg ctgattcttc taaatctttt gtgatggaaa acttttcttc gtaccacggg     180
actaaacctg gttatgtaga ttccattcaa aaaggtatac aaaagccaaa atctggtaca     240
caaggaaatt atgacgatga ttggaaaggg ttttatagta ccgacaataa atacgacgct     300
gcgggatact ctgtagataa tgaaaacccg ctctctggaa aagctggagg cgtggtcaaa     360
gtgacgtatc caggactgac gaaggttctc gcactaaaag tggataatgc cgaaactatt     420
aagaaagagt taggtttaag tctcactgaa ccgttgatgg agcaagtcgg aacggaagag     480
tttatcaaaa ggttcggtga tggtgcttcg cgtgtagtgc tcagccttcc cttcgctgag     540
gggagttcta gcgttgaata tattaataac tgggaacagg cgaaagcgtt aagcgtagaa     600
cttgagatta attttgaaac ccgtggaaaa cgtggccaag atgcgatgta tgagtatatg     660
gctcaagcct gtgcaggaaa tcgtgtcagg cgatcagtag gtagctcatt gtcatgcatc     720
aacctggatt gggatgttat ccgtgataaa actaaaacta gatcgaatc tctgaaagaa     780 cacggtccga tcaaaaacaa aatgagcgaa agcccgaaca aaactgtatc tgaagaaaaa     840
gctaaacagt acctggaaga attccaccag actgcactgg aacacccgga actgtctgaa     900
cttaagaccg ttactggtac caacccggta ttcgctggtg ctaactacgc tgcttgggca     960
gtaaacgttg ctcaggttat cgatagcgaa actgctgata acctggaaaa aactaccgcg    1020
gctctgtcta tcctgccggg tatcggtagc gtaatgggca tcgcagacgg cgccgttcac    1080
cacaacactg aagaaatcgt tgcacagtct atcgctctga gctctctgat ggttgctcag    1140
gccatcccgc tggtaggtga actggttgat atcggtttcg ctgcatacaa cttcgttgaa    1200
agcatcatca cctgttcca ggttgttcac aactcttaca accgcccggc ttactctccg    1260
ggtcacaaga cgcatgcacc tacttctagc tctaccaaga aaacccagct gcagctcgag    1320
cacctgctgc tggatttgca gatgatcctg aacggtatca caattacaa gaacccgaaa    1380 ctgacgcgta tgctgacctt caagttctac atgccgaaga aggccaccga actgaaacac    1440
ctgcagtgtc tagaagaaga actgaaaccg ctggaggaag ttctgaacct ggctcagtct    1500
aaaaacttcc acctgcggcc gcgtgacctg atctctaaca tcaacgtaat cgttctggaa    1560
ctgaagggct ctgaaaccac cttcatgtgt gaatacgctg atgagaccgc aaccatcgta    1620
```
gaattcctga accgttggat caccttctgt cagtctatca tctctaccct gacctga    1677

<210> SEQ ID NO 42
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

```
Ile Val Ala Gln Ser Ile Ala Leu Ser Ser Leu Met Val Ala Gln Ala
            355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415

Ser Ser Thr Lys Lys Thr Gln Leu Gln Leu Glu His Leu Leu Leu Asp
            420                 425                 430

Leu Gln Met Ile Leu Asn Gly Ile Asn Asn Tyr Lys Asn Pro Lys Leu
        435                 440                 445

Thr Arg Met Leu Thr Phe Lys Phe Tyr Met Pro Lys Lys Ala Thr Glu
450                 455                 460

Leu Lys His Leu Gln Cys Leu Glu Glu Glu Leu Lys Pro Leu Glu Glu
465                 470                 475                 480

Val Leu Asn Leu Ala Gln Ser Lys Asn Phe His Leu Arg Pro Arg Asp
                485                 490                 495

Leu Ile Ser Asn Ile Asn Val Ile Val Leu Glu Leu Lys Gly Ser Glu
            500                 505                 510

Thr Thr Phe Met Cys Glu Tyr Ala Asp Glu Thr Ala Thr Ile Val Glu
        515                 520                 525

Phe Leu Asn Arg Trp Ile Thr Phe Cys Gln Ser Ile Ile Ser Thr Leu
530                 535                 540

Thr His His His His His His
545                 550

<210> SEQ ID NO 43
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Ala Asp Asp Val Ala Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160
```

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
        180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr His His His His His His
        515                 520                 525

<210> SEQ ID NO 44
<211> LENGTH: 1656
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
gtgagcagaa aactgtttgc gtcaatctta atagggcgcg tactggggat aggggcccca      60
ccttcagccc atgcaggcgc tgatgatgtt gctgattctt ctaaatcttt tgtgatggaa     120
aacttttctt cgtaccacgg gactaaacct ggttatgtag attccattca aaaaggtata     180
caaaagccaa atctggtac acaaggaaat tatgacgatg attggaaagg gtttttatagt    240
accgacaata atacgacgc tgcgggatac tctgtagata atgaaaaccc gctctctgga     300
aaagctggag gcgtggtcaa agtgacgtat ccaggactga cgaaggttct cgcactaaaa     360
gtggataatg ccgaaactat taagaaagag ttaggtttaa gtctcactga accgttgatg     420
gagcaagtcg gaacggaaga gtttatcaaa aggttcggtg atggtgcttc gcgtgtagtg     480
ctcagccttc ccttcgctga ggggagttct agcgttgaat atattaataa ctgggaacag     540
gcgaaagcgt taagcgtaga acttgagatt aatttgaaa cccgtggaaa acgtggccaa      600
gatgcgatgt atgagtatat ggctcaagcc tgtgcaggaa atcgtgtcag gcgatcagta     660
ggtagctcat tgtcatgcat caacctggat tgggatgtta ccgtgataa aactaaaact      720
aagatcgaat ctctgaaaga acacggtccg atcaaaaaca aaatgagcga aagcccgaac     780
aaaactgtat ctgaagaaaa agctaaacag tacctggaag aattccacca gactgcactg     840
gaacacccgg aactgtctga acttaagacc gttactggta ccaacccggt attcgctggt     900
gctaactacg ctgcttgggc agtaaacgtt gctcaggtta tcgatagcga aactgctgat     960
aacctggaaa aaactaccgc ggctctgtct atcctgccgg gtatcggtag cgtaatgggc    1020
atcgcagacg gcgccgttca ccacaacact gaagaaatcg ttgcacagtc tatcgctctg    1080
agctctctga tggttgctca ggccatcccg ctggtaggtg aactggttga tatcggtttc    1140
gctgcataca acttcgttga aagcatcatc aacctgttcc aggttgttca caactcttac    1200
aaccgcccgg cttactctcc gggtcacaag acgcatgcac ctacttctag ctctaccaag    1260
aaaacccagc tgcagctcga gcacctgctg ctggatttgc agatgatcct gaacggtatc    1320
aacaattaca gaacccgaa actgacgcgt atgctgacct tcaagttcta catgccgaag    1380
aaggccaccg aactgaaaca cctgcagtgt ctagaagaag aactgaaacc gctggaggaa    1440
gttctgaacc tggctcagtc taaaaacttc cacctgcggc cgcgtgacct gatctctaac    1500
atcaacgtaa tcgttctgga actgaagggc tctgaaacca ccttcatgtg tgaatacgct    1560
gatgagaccg caaccatcgt agaattcctg aaccgttgga tcaccttctg tcagtctatc    1620
atctctaccc tgacccacca tcaccatcat cactga                              1656
```

<210> SEQ ID NO 45
<211> LENGTH: 561
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Ala Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
```

-continued

```
                50                  55                  60
Ser Gly Thr Gln Gly Asn Tyr Asp Asp Asp Trp Lys Gly Phe Tyr Ser
 65                  70                  75                  80

Thr Asp Asn Lys Tyr Asp Ala Ala Gly Tyr Ser Val Asp Asn Glu Asn
                 85                  90                  95

Pro Leu Ser Gly Lys Ala Gly Val Val Lys Val Thr Tyr Pro Gly
                100                 105                 110

Leu Thr Lys Val Leu Ala Leu Lys Val Asp Asn Ala Glu Thr Ile Lys
                115                 120                 125

Lys Glu Leu Gly Leu Ser Leu Thr Glu Pro Leu Met Glu Gln Val Gly
            130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
            195                 200                 205

Gln Ala Cys Ala Gly Asn Arg Val Arg Arg Ser Val Gly Ser Ser Leu
210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
            290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
            355                 360                 365

Ile Pro Leu Val Gly Glu Leu Val Asp Ile Gly Phe Ala Ala Tyr Asn
370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr His Ala Pro Thr Ser
                405                 410                 415

Ser Ser Thr Lys Lys Thr Gln Leu Gln Leu Glu His Leu Leu Leu Asp
                420                 425                 430

Leu Gln Met Ile Leu Asn Gly Ile Asn Asn Tyr Lys Asn Pro Lys Leu
            435                 440                 445

Thr Arg Met Leu Thr Phe Lys Phe Tyr Met Pro Lys Lys Ala Thr Glu
            450                 455                 460

Leu Lys His Leu Gln Cys Leu Glu Glu Glu Leu Lys Pro Leu Glu Glu
465                 470                 475                 480
```

Val Leu Asn Leu Ala Gln Ser Lys Asn Phe His Leu Arg Pro Arg Asp
            485                 490                 495

Leu Ile Ser Asn Ile Asn Val Ile Val Leu Glu Leu Lys Gly Ser Glu
            500                 505                 510

Thr Thr Phe Met Cys Glu Tyr Ala Asp Glu Thr Ala Thr Ile Val Glu
            515                 520                 525

Phe Leu Asn Arg Trp Ile Thr Phe Cys Gln Ser Ile Ile Ser Thr Leu
        530                 535                 540

Thr Glu Asn Leu Tyr Phe Gln Gly His His His His His His His
545                 550                 555                 560

His

<210> SEQ ID NO 46
<211> LENGTH: 536
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Ala Asp Asp Val Ala Asp Ser Ser Lys Ser Phe Val Met Glu Asn
1               5                   10                  15

Phe Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
            195                 200                 205

Ile Arg Asp Lys Thr Lys Thr Lys Ile Glu Ser Leu Lys Glu His Gly
        210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

```
Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr His Ala Pro Thr Ser Ser Ser Thr Lys Lys Thr Gln Leu Gln
385                 390                 395                 400

Leu Glu His Leu Leu Leu Asp Leu Gln Met Ile Leu Asn Gly Ile Asn
                405                 410                 415

Asn Tyr Lys Asn Pro Lys Leu Thr Arg Met Leu Thr Phe Lys Phe Tyr
            420                 425                 430

Met Pro Lys Lys Ala Thr Glu Leu Lys His Leu Gln Cys Leu Glu Glu
        435                 440                 445

Glu Leu Lys Pro Leu Glu Glu Val Leu Asn Leu Ala Gln Ser Lys Asn
    450                 455                 460

Phe His Leu Arg Pro Arg Asp Leu Ile Ser Asn Ile Asn Val Ile Val
465                 470                 475                 480

Leu Glu Leu Lys Gly Ser Glu Thr Thr Phe Met Cys Glu Tyr Ala Asp
                485                 490                 495

Glu Thr Ala Thr Ile Val Glu Phe Leu Asn Arg Trp Ile Thr Phe Cys
            500                 505                 510

Gln Ser Ile Ile Ser Thr Leu Thr Glu Asn Leu Tyr Phe Gln Gly His
        515                 520                 525

His His His His His His
    530                 535

<210> SEQ ID NO 47
<211> LENGTH: 4679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47 ggatccccccg ggctgcagga attcgatatc aagcttatcg ataccgtcga cctcgagggg       60
gggcccggta ccagctttg ttcccttag tgagggttaa tttcgagctt ggcgtaatca         120
tggtcatagc tgtttcctgt gtgaaattgt tatccgctca caattccaca acatacga         180 gccggaagca taaagtgtaa agcctggggt gcctaatgag tgagtccccg atccgtcgag       240
ctcgacctgc aggggggggg gggcgctgag gtctgcctcg tgaagaaggt gttgctgact       300
cataccaggc ctgaatcgcc ccatcatcca gccagaaagt gagggagcca cggttgatga       360
gagctttgtt gtaggtggac cagttggtga ttttgaactt ttgctttgcc acggaacggt       420
ctgcgttgtc gggaagatgc gtgatctgat ccttcaactc agcaaaagtt cgatttattc       480
```

```
aacaaagccg ccgtcccgtc aagtcagcgt aatgctctgc cagtgttaca accaattaac      540
caattctgat tagaaaaact catcgagcat caaatgaaac tgcaatttat tcatatcagg      600
attatcaata ccatatttt gaaaaagccg tttctgtaat gaaggagaaa actcaccgag       660
gcagttccat aggatggcaa gatcctggta tcggtctgcg attccgactc gtccaacatc     720
aatacaacct attaatttcc cctcgtcaaa ataaggtta tcaagtgaga aatcaccatg       780
agtgacgact gaatccggtg agaatggcaa aagcttatgc atttctttcc agacttgttc    840
aacaggccag ccattacgct cgtcatcaaa atcactcgca tcaaccaaac cgttattcat    900
tcgtgattgc gcctgagcga gacgaaatac gcgatcgctg ttaaaaggac aattacaaac   960
aggaatcgaa tgcaaccggc gcaggaacac tgccagcgca tcaacaatat tttcacctga   1020
atcaggatat tcttctaata cctggaatgc tgttttcccg gggatcgcag tggtgagtaa   1080
ccatgcatca tcaggagtac ggataaaatg cttgatggtc ggaagaggca taaattccgt   1140
cagccagttt agtctgacca tctcatctgt aacatcattg caacgctac ctttgccatg    1200 tttcagaaac aactctggcg catcgggctt cccatacaat cgatagattg tcgcacctga   1260
ttgcccgaca ttatcgcgag cccatttata cccatataaa tcagcatcca tgttggaatt   1320
taatcgcggc ctcgagcaag acgtttcccg ttgaatatgg ctcataacac cccttgtatt   1380
actgtttatg taagcagaca gttttattgt tcatgatgat atattttat cttgtgcaat    1440 gtaacatcag agattttgag acacaacgtg gctttccccc ccccccctgc aggtcgagct  1500
cgacggatcg ggctgcagga attcggtgag gttatggcgg agggttgcga ggtctaggag   1560
aacagaggaa gtcatgcttt gaagcatata agctgccctg cccctcaagg ttttcttcaa   1620
gtgaggtttt atctaactgc ctaacggcag gggaaccgta tattgcttac ggtatgagac   1680
cccttaaacg tccggatagt caccgctctt ctttagctcc gcgacatgcc tagcaaccgt   1740
ggcgcgagag actcctacct ctgcccctat ttcagcccac gtgggaactg tccctgtctg    1800
gaaatactga tcgttcacca tttggctaat acgggacttc gtagatcgtc cttgagcctt    1860
tttcttacgg tgcgtctttt caagcttcga cctttgtgct tgcgcatatt tgccctcggg    1920
gtctgttttc cagcgttgtg cggcttttg tccgcctctg cgtcccatcg tggccaaggc    1980
tttccgctcg ctgctggtgg ctttacctgg tgcgttagag ccgctgtagg tctcgctctt    2040
ggattgggcg acatacccgc gcacgcgcct tgccatggtt tggcggtcgc gcatgggtgg    2100
catctcgttg tcgcggcctg caccgccgtg ggtgtgtgcg acgttgtagg cgtgctcata   2160
ggcgtcgatg attgctgcgt ctgtcaggcg ttggccttgc tggcgcaagc ggtggccagt   2220
cttaagcgca tgtctaaagg ctgtttcgtc gcgtgctgcg gttccttgga caatccagag   2280
cacacgcaca ccgtcgataa gttccgggtc atactggtcg agaccaccgg cgatttccgc   2340
gtctacgtcc tgggcgagtg ctttgaatgc ttgggcttct tcacggcggg tcttgaccgc   2400
gttgataagt tcgcggccag agctgaattg ctggcgtggg gtggggttga actggtcgtg   2460
tcctgccata tcccttacct gctttatcaa gtctccaagg cgcatcaccc ggttgtgctg   2520
cctataccaa cgataagcgg taggggcttt gcctgtgtag aacgggttgc ggctaaagcg   2580
gtgggaaaag tgcgggtcat ggtctaaaag ctcacccagc acacgcgtgg ttgctgcaag   2640
aagcttcatc tgcgcagatt taccgttacg gtcagcgtag acagggtcaa taagccatat   2700
gaactgggct tgccgttag ttgggttaat acccacccag gctggcccga cgctatgagt    2760
aatcagtgag cgcaccacgt cgcggacgta cgggtttaag tctgcggggt caccgcctgc   2820
ggtacctact tggtcaacgt ctacgaccag gacggcggcg tactgcttgg tggtgagcat   2880
```

```
ggcgtactcg caccgtccta aagcatcagt ctcgaagcga tacatacgcg gcgagttcgt   2940
gccgtcagcg ttgcgtcgat aggccttttt aaagtctcgt gtgactgaac cgtggagtac   3000
atcgcggcct agatgatcgc gtaaaaggtc gcggtcactg gcagatgctg gggtgttgtc   3060
cagtccacca cggtcgcgct cgacgcgggt aggtgtttta gtgtgcgcat tctgcgcatg   3120
agtctgtaaa ctcatgaccg tgctttctcc caggtgtgtg ctgggtgata agcgaaagtc   3180
atcgggttgc cgcccggtgg ctttcttcgt ttttcattgt ctttccctga ctctaaatga   3240
caccggtgtt atttactagc catgacacgc gaaaaatatg cctttacct gcggttacgt    3300 atggctagac atatggcaag ctatacgtaa ccgcgtttca gctgcacagg gctgtctgcg   3360
cagatttacc atcacgggac ttttcccagt tcaggctgcg catatttacg catacaacga   3420
aagcggttgc gcagatttac cacacactct gcgctgattt accgatacgc agaaaaagcg   3480
tgcgcagatt tacccatacg gtggcgaatt atccagagca ataggtatac agcaatacag   3540
taatacaggt gccataaacc tgtattactg tattgctgta tgcctgtaaa cctttattta   3600
ttgttgtgga cgtattcttc gaggtaggtg ctaacaatct cgcggatggt cacgcctttt   3660
tgggcggcga tgactttaag ttctgcgtga aggtcgcggt cgatttcaat cgtcatcttc   3720
ttgacgtagt cgcggcctgt gggttggtgg aatgcgcttc gcactgtttt cttctcggct   3780
gctggagtta gcttcgtggc tttttcatt gaggttcgcg ggccttgctg cgccctggcg    3840
cgttctttac tggtgctcat ttcatcatct ccatgagttc gtcggcgacg tggtcgtagc   3900
cgtgcatgtc ggggcctggg cagtatccaa acgctaggtg catatcttcg cgtagcggga   3960
tttcggtttt aaagtgcggc atgtgttccg cgtcgagcgc ttctcgtgcc gcgtcaaggg   4020
cgctggtgcc tttcctggcg aacgtcagta agactgcatg aggtgttccg ttgactgcgt   4080
cgcgcagctc ccatactcgg gagaggtcgg cagcagcaga acgggtcgga agaatgatga   4140
agtcgctgac tgcgattgct gcttcgatag cgttctcgtc tcctggcggc acatcgatac   4200
cgactgggcg atggcccact acgtgaacca tcaccctaat caagtttttt ggggtcgagg   4260
tgccgtaaag cactaaatcg gaaccctaaa gggagccccc gatttagagc ttgacgggga   4320
aagccggcga acgtggcgag aaaggaaggg aagaaagcga aaggagcggg cgctagggcg   4380
ctggcaagtg tagcggtcac gctgcgcgta accaccacac ccgccgcgct taatgcgccg   4440
ctacagggcg ctcccattcg ccattcaggc tgcgcaactg ttgggaaggg cgatcggtgc   4500
gggcctcttc gctattacgc cagctggcga aaggggatg tgctgcaagg cgattaagtt    4560
gggtaacgcc agggttttcc cagtcacgac gttgtaaaac gacggccagt gaattgtaat   4620
acgactcact ataggcgaa ttggagctcc accgcggtgg cggccgctct agaactagt    4679
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      9xHis tag

<400> SEQUENCE: 48

His His His His His His His His His
1               5

METHODS OF PRODUCING AGGREGATE-FREE MONOMERIC DIPHTHERIA TOXIN FUSION PROTEINS AND THERAPEUTIC USES

CROSS-REFERENCE TO RELATED APPLICATIONS

This application is a 35 U.S.C. § 371 U.S. national entry of International Application PCT/US2017/021715, having an international filing date of Mar. 10, 2017, which claims the benefit of U.S. Provisional Application No. 62/306,281, filed Mar. 10, 2016, the content of each of the aforementioned applications is herein incorporated by reference in their entirety.

STATEMENT OF GOVERNMENTAL INTEREST

This invention was made with government support under grant nos. AI037856, AI036973, AI097138, UC7AI095321-01, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 2, 2017, is named P13869-02_SL.txt and is 134,966 bytes in size.

BACKGROUND OF THE INVENTION

Ontak® (denileukin diftitox), is a 521 amino acid, recombinant, DNA-derived cytotoxic protein composed of the amino acid sequences for diphtheria toxin fragments A and a portion of fragment B ($Met_1$-$His_{388}$) and the sequences for human interleukin-2 (IL-2; $Ala_1$-$Thr_{133}$). It is currently produced in an *E. coli* expression system and has a molecular weight of 58 kD. Neomycin is used in the fermentation process but is undetectable in the final product. Ontak®, which is supplied in single use vials as a sterile, frozen solution intended for intravenous (IV) administration, was approved by the FDA in 1999 for the treatment of cutaneous T cell lymphoma (CTCL). The FDA placed Ontak® on clinical hold in June 2011 because of concerns regarding the presence of protein aggregates of heterogeneous molecular weight, excess residual DNA, and excess residual detergent in the final formulation. The production of Ontak® was achieved by expressing the recombinant protein in the *E. coli* cytoplasm, and this expression system resulted in the recombinant protein forming large insoluble aggregates or so-called inclusion bodies comprised of the Ontak® polypeptide. In the current process of production, which includes denaturation and refolding of the inclusion body forms, protein aggregates of heterogeneous molecular weight were still present in the final formulation. The presence of these aggregates in the purified form is a consequence of using *E. coli*-derived cytoplasmic inclusion bodies as the source of the polypeptide and because of the intrinsic hydrophobic nature of the toxin's transmembrane domain even in the presence of Tween 20. Ontak® produced using this method will hereafter be referred to as classic-Ontak® or c-Ontak®.

In addition, like all of the bacterial and plant toxins, c-Ontak® carries amino acid motifs that induce vascular leak syndrome (VLS). Approximately 30% of patients treated with c-Ontak® develop VLS symptoms ranging from peripheral edema with rapid weight gain to hypoalbuminemia to pulmonary edema. What is needed are 1) a process enabling the production of Ontak-like proteins at high yields and purity, eliminating aggregates in the final commercial product, and 2) modified Ontak-like proteins with minimal VLS side-effects to provide safer drugs to patients.

SUMMARY OF THE INVENTION

One embodiment of the present invention is a DNA expression vector comprising: a toxP; a mutant toxO that blocks Fe-mediated regulation of gene expression; and a DNA sequence encoding a protein, wherein the toxP and the mutant toxO regulate expression of the DNA segment encoding the protein. It is preferred that DNA expression vectors of the present invention include DNA sequences encoding a signal peptide so that a protein expressed off a DNA expression vector is attached to the signal peptide that is typically cleaved off to form a mature protein. The preferred mutant toxO is SEQ ID NO: 1 and the preferred signal peptide is SEQ ID NO: 5. The DNA expression vectors of the present invention may be used to produce many kinds of proteins such as CRM 197 and CRM 107, or a combination thereof. CRM protein sequences are illustrated in SEQ ID NOs: 18-21. It is preferred that the DNA expression vectors of the present invention encode a diphtheria toxin, or functional part thereof, attached to a receptor binding protein, or a functional part thereof to form a diphtheria toxin receptor fusion protein. The receptor binding protein portion of such fusion proteins may be selected from the group comprising IL-2, IL-3, IL-4, IL-6, IL-7, IL-15, EGF, FGF, substance P, CD4, aMSH, GRP, TT fragment C, GCSF, heregulin β1, a functional part thereof, or a combination thereof. Examples of diphtheria toxin fusion proteins include the proteins illustrated in any one of SEQ ID NOs: 11-15.

Another embodiment of the present invention is a DNA expression vector comprising: a toxP; a mutant toxO that blocks Fe-mediated regulation of gene expression; a DNA sequence encoding a protein comprising a signal sequence; a diphtheria toxin, or a functional part thereof, that is free of a diphtheria receptor binding domain or has a non-functional diphtheria toxin receptor binding domain, and a target receptor binding domain selected from the group comprising IL-2, IL-3, IL-4, IL-6, IL-7, IL-15, EGF, FGF, substance P, CD4, aMSH, GRP, TT fragment C, GCSF, heregulin β1, a functional part thereof, or a combination thereof, wherein the toxP and the mutant toxO regulate expression of the DNA sequence encoding the protein. Typically, a bacteria transformed with a DNA expression vector of the present invention produces a diphtheria toxin receptor binding fusion protein attached to a signal peptide that is directed to a periplasm, a culture medium, or both locations by the signal peptide. If the bacteria is *E. coli* then the signal peptide typically directs the diphtheria toxin receptor binding fusion protein to the periplasm. If the bacteria is *Corynebacterium diphtheria* then signal peptide directs the diphtheria toxin receptor binding fusion protein to the culture medium. It is preferred that a DNA expression vector of the present invention comprises SEQ ID NO: 3 and may comprise a DNA encoding a cleavable protein tag wherein the cleavable protein tag is attached to the diphtheria toxin receptor binding fusion protein. Example of diphtheria toxin receptor binding fusion protein produced from the DNA expression vectors of the present invention include anyone of SEQ ID Nos: 11 to 15.

Another embodiment of the present invention includes a method for producing aggregate-free monomeric diphtheria toxin fusion proteins comprising the following steps: transforming bacteria with a DNA expression vectors of the present invention; forming a transformant; incubating the transformant in a culture medium to allow expression of a protein that is secreted into the culture medium; and purifying the protein from the culture medium. The preferred bacteria used in this method is *Corynebacterium diphtheria*.

Another embodiment of the present invention includes a method for producing aggregate-free monomeric diphtheria toxin fusion proteins comprising the following steps: 1) transforming *Corynebacterium diphtheria* strain with a DNA vector comprising: a toxP; a mutant toxO that blocks Fe-mediated regulation of gene expression; a DNA sequence encoding a protein comprising: signal peptide; a diphtheria toxin, or a functional part thereof, that is free of a diphtheria receptor binding domain or has a non-functional diphtheria toxin receptor binding domain; and a target receptor binding domain selected from the group comprising IL-2, IL-3, IL-4, IL-6, IL-7, IL-15, EGF, FGF, substance P, CD4, αMSH, GRP, TT fragment C, GCSF, heregulin β1, TNFα, TGFβ, a functional part thereof, or a combination thereof, wherein the toxP and the mutant toxO regulate expression of the DNA sequence encoding the protein; 2) forming a transformant; 3) incubating the transformant in a culture medium to allow expression of the protein and that is secreted into the culture medium; and 4) purifying the diphtheria toxin fusion protein from the culture medium. Examples of diphtheria toxin receptor fusion protein produced by methods of the present invention include any one of SEQ ID NOs: 11 to 15. The preferred *Corynebacterium diphtheria* strain used in the methods of the present invention is *Corynebacterium* C7 beta (−), tox (−).

Another embodiment of the present invention includes a method of treating a patient with tuberculosis comprising the following steps: preparing a diphtheria toxin fusion protein as provided in this application; administering the diphtheria toxin fusion protein to a patient with tuberculosis.

Another embodiment of the present invention includes a DNA expression vector comprising a mutant toxO promoter.

Another embodiment of the present invention includes a *Corynebacterium diphtheria* strain containing a DNA expression vector of the present invention.

Another embodiment of the present invention is method of making a protein comprising the following steps: providing a DNA expression vector comprising a toxP, a mutant toxO that blocks Fe-mediated regulation of gene expression, a signal sequence, and a DNA sequence encoding a protein; transforming a bacteria strain with the DNA vector to form a transformant; incubating the transformant in a culture medium for a period of time to allow expression of a protein that is secreted into the culture medium; and purifying the protein from the culture medium.

Another embodiment of the present invention is a fusion protein selected from any one of SEQ ID NOs: 11-15.

Another embodiment of the present invention is a pharmaceutical composition comprising a fusion protein described above.

Another embodiment of the present invention is a pharmaceutical composition comprising a fusion protein describe above, and at least one or more other chemotherapy agents. Examples of chemotherapy agents include isoniazid, rifampin, rifabutin, rifapentine, pyrazinamide, ethambutol, streptomycin, amikacin, kanamycin, ethionamide, protionamide, terizidone, thiacetazone, cycloserine, capreomycin, para-amino salicylic acid (PAS), viomycin, ofloxacin, ciprofloxacin, levofloxacin, moxifloxacin, bedaquiline, or delamanid, linezolid, tedezolid, amoxicillin-clavulanic acid, meropenem, imipenem, clarithromycin or clofazimine.

A pharmaceutical composition of comprising a fusion protein described above, and at least one or more other antimicrobial agents. Examples of antimicrobial agents include isoniazid, rifampin, rifabutin, rifapentine, pyrazinamide, ethambutol, streptomycin, amikacin, kanamycin, ethionamide, protionamide, terizidone, thiacetazone, cycloserine, capreomycin, para-amino salicylic acid (PAS), viomycin, ofloxacin, ciprofloxacin, levofloxacin, moxifloxacin, bedaquiline, or delamanid, linezolid, tedezolid, amoxicillin-clavulanic acid, meropenem, imipenem, clarithromycin, or clofazimine.

Another embodiment of the present invention is a method of treating or preventing cancer in a subject comprising administering to the subject an effective amount of a pharmaceutical composition comprising a fusion protein selected from any one of SEQ ID NOs: 11-15.

Another embodiment of the present invention is a method of treating or preventing tuberculosis in a subject comprising administering to the subject an effective amount of a pharmaceutical composition comprising a fusion protein selected from any one of SEQ ID NOs: 11-15.

Another embodiment of the present invention is a prokaryotic cell line comprising a DNA expression vector of the present invention.

Another embodiment of the present invention is kit comprising the DNA expression vector of the present invention.

Another embodiment of the present invention is a toxP comprising SEQ ID NO: 2.

Another embodiment of the present invention is a protein of any one of SEQ ID NOs: 11 to 15.

BRIEF DESCRIPTION OF THE DRAWINGS

FIG. 1a-1b illustrates: a) a mutant toxO of the present invention (SEQ ID NO: 1), b) a wild type toxO (SEQ ID NO: 25), and c) a DtxR consensus binding sequence.

FIG. 2a-2b illustrates: a) illustrates the classic denileukin diftitox (c-denileukin diftitox) expression vector used to manufacture Ontak® and b) illustrates the secreted denileukin diftitox (s-denileukin diftitox) expression vector including the tox promoter (toxP), and mutant toxO of the present invention. FIG. 2a discloses SEQ ID NO: 26 and FIG. 2b discloses SEQ ID NO: 27.

FIG. 3 illustrates a vascular leak mutant (VLM) called c-denileukin diftitox-VLM has equivalent potency to c-denileukin diftitox in killing IL2-receptor-bearing cells.

FIG. 4 illustrates c-denileukin diftitox-VLM does not cause vascular leak in vitro.

FIG. 5 illustrates that c-denileukin diftitox-VLM has significantly less acute toxicity in vivo than c-Ontak® using a mouse survival model.

FIG. 6 illustrates a diphtheria toxin-based fusion protein toxin platform technology of the present invention.

FIG. 7 illustrates plasmid pKN2.6Z-LC127 with the tox promoter (toxP of SEQ ID NO: 2) and a mutant tox operator (toxO) (DNA SEQ ID NO: 1), a signal peptide (DNA SEQ ID NO: 4) attached to c-denileukin diftitox DNA sequences (DNA SEQ ID NO: 6).

FIG. 8a-8b illustrates: a) the problems of the conventional process of manufacturing Ontak® as cytoplasmic inclusion bodies in *E. coli* and b) illustrates easy and clean manufacturing process of producing a secreted-denileukin diftitox having one less amino acid than the Ontak® protein. FIG. 8a discloses "fMGADD" as SEQ ID NO: 28 and FIG. 8b discloses "GADD" as SEQ ID NO: 29.

FIG. 9 illustrates an immunoblot of s-denileukin diftitox prepared by the process of the present invention where s-denileukin diftitox is expressed within a *Corynebacterium diphtheria* strain C7 beta (−), tox (−) and is secreted into the culture medium.

FIG. 10 illustrates how a denileukin diftitox of the present invention, is expected to deplete IL-2R (CD25+) bearing T cells ($T_{regs}$) within a tuberculous granuloma. $T_{regs}$ are immunosuppressive by their inhibition of $T_{eff}$ cells.

FIG. 11 illustrates diphtheria fusion proteins used in the in vivo treatment of subjects (mice) with *M. tuberculosis*.

FIG. 12 illustrates the results of treating subjects (mice) infected with *M. tuberculosis* with diphtheria toxin-based fusion proteins.

FIG. 13 illustrates a diphtheria toxin-based fusion protein regimen for treating subjects (mice) infected with *M. tuberculosis*.

FIG. 14 illustrates the use of a diphtheria toxin-based fusion protein to treat subjects (humans) with malignant melanoma.

FIG. 15 illustrates the three constructs for rapid production of VLM s-Ontak and related proteins using His (histidine tags) ("$His_6$/6×His" and "$His_9$/9×His" disclosed as SEQ ID NOS 23 and 48, respectively).

FIG. 16 illustrates purified VLM s-Ontak at greater than 97% purity produced using the C-terminal $His_6$ VLM s-Ontak construct ("$His_6$" disclosed as SEQ ID NO: 23).

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "activity" refers to the ability of a gene to perform its function such as Indoleamine 2,3-dioxygenase (an oxidoreductase) catalyzing the degradation of the essential amino acid tryptophan (trp) to N-formyl-kynurenine.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

c—means "classic" when attached to a term such as c-denileukin diftitox means Ontak® or that commercially available protein.

By "disease" is meant any condition or disorder that damages or interferes with the normal function of a cell, tissue, or organ. Examples of diseases include cancer and tuberculosis.

By "effective amount" is meant the amount of a required to ameliorate the symptoms of a disease relative to an untreated patient. The effective amount of active compound (s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "express" refers to the ability of a gene to express the gene product including for example its corresponding mRNA or protein sequence (s).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids is—means "immature secreted" when attached to a term such as is-denileukin diftitox means immature secreted denileukin diftitox that contains a signal peptide.

ms—means "mature secreted" when attached to a term such as ms-denileukin diftitox means mature secreted denileukin diftitox that has been processed and no longer contains a signal peptide.

n—means "new" when attached to a term such as n-denileukin diftitox means new denileukin diftitox.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

By "reduces" is meant a negative alteration of at least 10%, 25%, 50%, 75%, or 100%.

A "reference" refers to a standard or control conditions such as a sample (human cells) or a subject that is a free, or substantially free, of an agent such as one or more compositions of the present invention comprising a nucleic acid or protein sequence such as anyone of SEQ ID NOs: 11-15, or fusion proteins thereof.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or there between.

s—means "secreted" when attached to a term such as s-denileukin diftitox means secreted denileukin diftitox. Secreted denileukin diftitox includes is- and m-forms.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

VLM—means "vascular leakage mutant" when attached to a term such as denileukin diftitox-VLM means denileukin diftitox vascular leakage mutant.

w—means "wild type" when attached to a term such as w-diphtheria toxin means wild type-diphtheria toxin.

DETAILED DESCRIPTION OF THE INVENTION

One embodiment of the present invention is the discovery of a process that produces aggregate-free, monomeric, diphtheria toxin fusion proteins having enhanced purity and quality. This process includes transforming bacteria including preferably, strains of *Corynebacterium diphtheria* with DNA expression vectors of the present invention. DNA expression vectors of the present invention are designed to include specific genetic elements comprising a tox promoter (toxP) and an overlapping novel, mutated tox operator (toxO), preferably a signal sequence, and a DNA sequence encoding a protein. The protein is preferably a fusion protein including a diphtheria toxin, or functional part thereof, and a target receptor binding domain or a functional part thereof. The term "functional part thereof" means a part of a diphtheria toxin protein that acts as a toxin or the part of a target receptor binding domain that binds to its receptor. DNA expression vectors of the present invention are designed so proteins are expressed from a tox promoter (toxP) and a mutant tox operator (toxO).

Mutant toxO toxO, is a 19-bp operator region that is composed of two 9 bp imperfect palindromic arms interrupted by a central cytosine (C) base. The wild type toxO (FIG. 1b) and a mutant toxO (FIG. 1a) operator discovered by inventors are shown in FIG. 1. SEQ ID NO: 1 illustrates one embodiment of the DNA sequence of a mutant toxO this invention. toxP is a promoter having a DNA sequence of SEQ ID NO: 2. SEQ ID NO: 2 illustrates the toxP DNA sequences include the toxO DNA sequences. SEQ ID NO: 3 is a DNA sequence including a toxP, a toxO, a signal peptide, and a DNA sequence encoding a protein. The asterisks in SEQ ID NO: 3 indicate the changes introduced to create the mutant toxO.

(Mutant toxO DNA sequence)

SEQ ID NO: 1

TTAGGATAGCTAAGTCCAT (toxP including the mutant toxO DNA sequence where the mutant toxO sequence is underlined)

SEQ ID NO: 2

TTGATTTCAGAGCACCCTTATAA<u>TTAGGATAGCTAAGTCCAT</u>

The toxO DNA operator sequence is bound by a protein known as the diphtheria toxin repressor, DtxR. DtxR is a global iron-activated regulatory protein that is able to control gene expression. In iron-replete conditions, $Fe^{2+}$ and $Fe^{3+}$ ions bind to apo-DtxR causing a conformational change that allows the formation of homodimers of the DtxR repressor, which bind to the tox operator (toxO) DNA sequence and repress tox gene expression. In low iron environments, $Fe^{2+}$ and $Fe^{3+}$ ions disassociate from DtxR causing it to lose its DNA binding capability and disassociate from the operator; this event thereby allows expression of tox gene products. FIG. 1b illustrates the wild type toxO DNA sequence.

To overcome the inhibitory effect of $Fe^{2+}$ and $Fe^{3+}$ ions on tox expression, a DNA expression vector was created replacing the wild type (WT) toxO with a mutant toxO DNA sequence. This change blocks Fe ion-mediated regulation of tox gene expression. FIG. 1a, SEQ ID NO: 1, and SEQ ID NO: 3 illustrate the mutant toxO DNA sequence of the present invention. Under this invention, bacteria such as E. coli and C. diphtheria harboring a recombinant plasmid encoding a diphtheria toxin fusion protein under the control of toxP and the mutant toxO may be grown in Fe-replete media, allowed to grow to high densities, and will not require a shift to Fe-free media to induce expression. The constitutive expression of tox gene products in iron replete medium represents a significant advance in the field. C. diphtheria, specifically the C7 beta (−), tox (−) strain is the preferred host bacteria for the production of all diphtheria-toxin related recombinant proteins using the DNA expression vectors of the present invention. The DNA expression vectors of the present invention may be used in other bacteria such as E. coli.

DNA Expression Vectors

The DNA expression vectors of the present invention includes a toxP, mutant toxO, a DNA sequence encoding a protein, and preferably a signal sequence. SEQ ID NO: 3 is one example of a DNA sequence containing these genetic elements that may be part of a DNA expression vector of the present invention. As mentioned, the asterisks observed in SEQ ID NO: 3 are placed above the base pair changes between the mutant and wild type toxO. SEQ ID NO: 3 is numbered such that the toxP extends from base 1 to 30, and toxO begins at base 24 and ends at base 42 (prior to the underlined DNA sequence). The underlined DNA sequence represents base 74 to base 148 and is a region of DNA encoding a 25 amino acid signal sequence (also observe in SEQ ID NO:4, SEQ ID NO: 5, and FIG. 2). The DNA expression vectors of the present invention are preferably constructed so one or more proteins are expressed from toxP, mutant toxO, and are translated with an N-terminal signal sequence. The N-terminal signal sequence targets the one or more proteins (expressed from the vector) for secretion, and the N-terminal signal peptide is later cleaved to make mature active proteins. SEQ ID NO: 3 includes DNA sequences encoding proteins such as a novel denileukin diftitox called secreted-denileukin diftitox, or s-denileukin diftitox. The s-denileukin diftitox has two forms called immature secreted-denileukin diftitox (is-denileukin diftitox) and mature secreted-denileukin diftitox (ms-denileukin diftitox). SEQ ID NO: 12 is of is-denileukin diftitox of the present invention and SEQ ID NO: 13 is of ms-denileukin diftitox of the present invention. The is-denileukin diftitox contains a signal sequence that during processing is cleaved off to form ms-denileukin diftitox. In addition, SEQ ID NO:3 includes a DNA sequence beginning at base 149 to 1711 of SEQ ID that encodes a protein, specifically a fusion protein containing the functional parts of a diphtheria toxin and the functional parts of IL 2. A new denileukin diftitox fusion protein sequence is formed called ms-denileukin diftitox that is a 520 amino acid polypeptide and is composed of the amino acid sequences for diphtheria toxin fragments A and a portion of fragment B ($Gly_1$-$His_{387}$) and the sequences for human interleukin-2 (IL-2; $Ala_1$-$Thr_{133}$). As a result of cleavage of the signal sequence, ms-denileukin diftitox of the present invention lacks the first methionine present in classic-denileukin diftitox (c-denileukin diftitox) and is thereby one amino acid shorter than the amino acid sequence of the classic-denileukin diftitox protein known as Ontak®. SEQ ID NO: 13 is the protein sequence of the new diftitox protein sequence ms-denileukin diftitox which may be compared to SEQ ID NO: 10 containing the protein sequence of the classis-denileukin diftitox (c-denileukin diftitox) known as Ontak®.

DNA expression vectors of the present invention include DNA sequences encoding one or more protein(s). A preferred protein of the present invention is a fusion protein comprising a diphtheria toxin (or a functional part thereof) and a target receptor binding protein (or a functional part thereof). An example of a diphtheria toxin that may be produced from a DNA expression is any functional part of a diphtheria toxin or any functional part of a diphtheria toxin vascular leakage mutant. Examples of proteins of target receptor binding domains produced from a DNA expression vector of the present invention include, IL-2, IL-3, IL-4, IL-6, IL-7, IL-15, EGF, FGF, substance P, CD4, aMSH, GRP, TT fragment C, GCSF, heregulin β1, TNFα, TGFβ, or a combination thereof. Other target receptor binding domains may be used depending upon the therapeutic application; however, SEQ. ID NO. 9 is a preferred DNA sequence encoding a functional part of IL2 receptor binding domain. For the purposes of the present invention, some of the DNA plasmids and the genetic elements thereof are illustrated in FIG. 1, FIG. 2, FIG. 6, and FIG. 7. Examples of fusion proteins encoded by DNA expression vectors of the present invention include SEQ ID NOs: 11, 12, 13, 14, 15, 19, and 21.

(DNA sequence encoding secreted-denileukin diftitox or s-denileukin diftitox. Sequence includes toxP, mutant toxO, signal sequence, a functional part of diphtheria toxin and a functional part of IL2. Bold font and asterisks indicate the changes introduces to create the mutant toxO)

SEQ ID NO: 3

```
                                          ****  *  *
  1    TTGATTTCAGAGCACCCTTATAATTAGGATAGCTAAGTCCATTATTTTAT

51    GAGTCCTGGTAAGGGGATACGTTGTGAGCAGAAAACTGTTTGCGTCAATC
```

-continued

```
 101   TTAATAGGGGCGCTACTGGGGATAGGGGCCCCACCTTCAGCCCATGCAGG
 151   CGCTGATGATGTTGTTGATTCTTCTAAATCTTTTGTGATGGAAAACTTTT
 201   CTTCGTACCACGGGACTAAACCTGGTTATGTAGATTCCATTCAAAAAGGT
 251   ATACAAAAGCCAAAATCTGGTACACAAGGAAATTATGACGATGATTGGAA
 301   AGGGTTTTATAGTACCGACAATAAATACGACGCTGCGGGATACTCTGTAG
 351   ATAATGAAAACCCGCTCTCTGGAAAAGCTGGAGGCGTGGTCAAAGTGACG
 401   TATCCAGGACTGACGAAGGTTCTCGCACTAAAAGTGGATAATGCCGAAAC
 451   TATTAAGAAAGAGTTAGGTTTAAGTCTCACTGAACCGTTGATGGAGCAAG
 501   TCGGAACGGAAGAGTTTATCAAAAGGTTCGGTGATGGTGCTTCGCGTGTA
 551   GTGCTCAGCCTTCCCTTCGCTGAGGGGAGTTCTAGCGTTGAATATATTAA
 601   TAACTGGGAACAGGCGAAAGCGTTAAGCGTAGAACTTGAGATTAATTTTG
 651   AAACCCGTGGAAAACGTGGCCAAGATGCGATGTATGAGTATATGGCTCAA
 701   GCCTGTGCAGGAAATCGTGTCAGGCGATCAGTAGGTAGCTCATTGTCATG
 751   CATCAACCTGGATTGGGATGTTATCCGTGATAAAACTAAAACTAAGATCG
 801   AATCTCTGAAAGAACACGGTCCGATCAAAAACAAAATGAGCGAAAGCCCG
 851   AACAAAACTGTATCTGAAGAAAAAGCTAAACAGTACCTGGAAGAATTCCA
 901   CCAGACTGCACTGGAACACCCGGAACTGTCTGAACTTAAGACCGTTACTG
 951   GTACCAACCCGGTATTCGCTGGTGCTAACTACGCTGCTTGGGCAGTAAAC
1001   GTTGCTCAGGTTATCGATAGCGAAACTGCTGATAACCTGGAAAAAACTAC
1051   CGCGGCTCTGTCTATCCTGCCGGGTATCGGTAGCGTAATGGGCATCGCAG
1101   ACGGCGCCGTTCACCACAACACTGAAGAAATCGTTGCACAGTCTATCGCT
1151   CTGAGCTCTCTGATGGTTGCTCAGGCCATCCCGCTGGTAGGTGAACTGGT
1201   TGATATCGGTTTCGCTGCATACAACTTCGTTGAAAGCATCATCAACCTGT
1251   TCCAGGTTGTTCACAACTCTTACAACCGCCCGGCTTACTCTCCGGGTCAC
1301   AAGACGCATGCACCTACTTCTAGCTCTACCAAGAAAACCCAGCTGCAGCT
1351   CGAGCACCTGCTGCTGGATTTGCAGATGATCCTGAACGGTATCAACAATT
1401   ACAAGAACCCGAAACTGACGCGTATGCTGACCTTCAAGTTCTACATGCCG
1451   AAGAAGGCCACCGAACTGAAACACCTGCAGTGTCTAGAAGAAGAACTGAA
1501   ACCGCTGGAGGAAGTTCTGAACCTGGCTCAGTCTAAAAACTTCCACCTGC
1551   GGCCGCGTGACCTGATCTCTAACATCAACGTAATCGTTCTGGAACTGAAG
1601   GGCTCTGAAACCACCTTCATGTGTGAATACGCTGATGAGACCGCAACCAT
1651   CGTAGAATTCCTGAACCGTTGGATCACCTTCTGTCAGTCTATCATCTCTA
1701   CCCTGACCTGA                                        < 1711
```

(Signal DNA Sequence)

SEQ ID NO: 4

```
  74   GTGAGCAGAAAACTGTTTGCGTCAATCTTAATAGGGGCGCTACTGGGGAT
 124   AGGGGCCCCACCTTCAGCCCATGCA                          < 148
```

(Signal Protein Sequence)

SEQ ID NO: 5

```
 -25   MSRKLFASILIGALLGIGAPPSAHA                          < -1
```

(classic-denileukin diftitox DNA sequence)

SEQ ID NO: 6

```
   1   ATG

4   GGCGCTGATGATGTTGTTGATTCTTCTAAATCTTTTGTGATGGAAAACTT
```

-continued

| | |
|---|---|
| 54 | TTCTTCGTACCACGGGACTAAACCTGGTTATGTAGATTCCATTCAAAAAG |
| 104 | GTATACAAAAGCCAAAATCTGGTACACAAGGAAATTATGACGATGATTGG |
| 154 | AAAGGGTTTTATAGTACCGACAATAAATACGACGCTGCGGGATACTCTGT |
| 204 | AGATAATGAAAACCCGCTCTCTGGAAAAGCTGGAGGCGTGGTCAAAGTGA |
| 254 | CGTATCCAGGACTGACGAAGGTTCTCGCACTAAAAGTGGATAATGCCGAA |
| 304 | ACTATTAAGAAAGAGTTAGGTTTAAGTCTCACTGAACCGTTGATGGAGCA |
| 354 | AGTCGGAACGGAAGAGTTTATCAAAAGGTTCGGTGATGGTGCTTCGCGTG |
| 404 | TAGTGCTCAGCCTTCCCTTCGCTGAGGGGAGTTCTAGCGTTGAATATATT |
| 454 | AATAACTGGGAACAGGCGAAAGCGTTAAGCGTAGAACTTGAGATTAATTT |
| 504 | TGAAACCCGTGGAAAACGTGGCCAAGATGCGATGTATGAGTATATGGCTC |
| 554 | AAGCCTGTGCAGGAAATCGTGTCAGGCGATCAGTAGGTAGCTCATTGTCA |
| 604 | TGCATCAACCTGGATTGGGATGTTATCCGTGATAAAACTAAAACTAAGAT |
| 654 | CGAATCTCTGAAAGAACACGGTCCGATCAAAAACAAAATGAGCGAAAGCC |
| 704 | CGAACAAAACTGTATCTGAAGAAAAAGCTAAACAGTACCTGGAAGAATTC |
| 754 | CACCAGACTGCACTGGAACACCCGGAACTGTCTGAACTTAAGACCGTTAC |
| 804 | TGGTACCAACCCGGTATTCGCTGGTGCTAACTACGCTGCTTGGGCAGTAA |
| 854 | ACGTTGCTCAGGTTATCGATAGCGAAACTGCTGATAACCTGGAAAAAACT |
| 904 | ACCGCGGCTCTGTCTATCCTGCCGGGTATCGGTAGCGTAATGGGCATCGC |
| 954 | AGACGGCGCCGTTCACCACAACACTGAAGAAATCGTTGCACAGTCTATCG |
| 1004 | CTCTGAGCTCTCTGATGGTTGCTCAGGCCATCCCGCTGGTAGGTGAACTG |
| 1054 | GTTGATATCGGTTTCGCTGCATACAACTTCGTTGAAAGCATCATCAACCT |
| 1104 | GTTCCAGGTTGTTCACAACTCTTACAACCGCCCGGCTTACTCTCCGGGTC |
| 1154 | ACAAGACGCATGCACCTACTTCTAGCTCTACCAAGAAAACCCAGCTGCAG |
| 1204 | CTCGAGCACCTGCTGCTGGATTTGCAGATGATCCTGAACGGTATCAACAA |
| 1254 | TTACAAGAACCCGAAACTGACGCGTATGCTGACCTTCAAGTTCTACATGC |
| 1304 | CGAAGAAGGCCACCGAACTGAAACACCTGCAGTGTCTAGAAGAAGAACTG |
| 1354 | AAACCGCTGGAGGAAGTTCTGAACCTGGCTCAGTCTAAAAACTTCCACCT |
| 1404 | GCGGCCGCGTGACCTGATCTCTAACATCAACGTAATCGTTCTGGAACTGA |
| 1454 | AGGGCTCTGAAACCACCTTCATGTGTGAATACGCTGATGAGACCGCAACC |
| 1504 | ATCGTAGAATTCCTGAACCGTTGGATCACCTTCTGTCAGTCTATCATCTC |
| 1554 | TACCCTGACCTGA | < 1566 |

Formation of Diphtheria Toxin Fusion Proteins Having Minimal, or No, Vascular Leakage (Denileukin Diftitox-VLMs)

Like all of the bacterial and plant toxins, denileukin diftitox carries amino acid motifs that may induce vascular leak syndrome (VLS). Approximately 30% of patients treated with Ontak® develop VLS ranging from rapid weight gain with peripheral edema to hypoalbuminemia to pulmonary edema. Mutations were made to the DNA sequence of Ontak® as described in U.S. Pat. No. 8,865,866. It was discovered that DNA mutations made to the DNA sequence such that the valine (GTT) at the $7^{th}$ residue of SEQ ID NO: 10 is replaced with an alanine as shown in SEQ ID NO: 16, resulted in the fusion toxin having little, or no, vascular leak syndrome side effects. These mutants are referred to as "vascular leak mutants" (VLM). The vascular leak mutants, or denileukin diftitox-VLMS are shown to have the same potency as c-denileukin diftitox in FIG. 3, not to cause vascular leak in FIG. 4, and to have significantly less acute toxicity in vivo than c-denileukin diftitox in FIG. 5. s-denileukin diftitox-VLM, has an alanine replacing the valine at the $6^{th}$ residue shown in in SEQ ID NOS: 14 and 15. s-denileukin diftitox-VLM protein should have a similar decrease in toxicity as that found with the c-denileukin diftitox-VLM protein.

Also, the sequences $V_{29}D_{30}S_{31}$ and $I_{290}D_{291}S_{292}$ shown in SEQ ID NO: 10 (amino acid sequence of c-denileukin diftitox), when mutated also will reduce VLS. A claim in this discovery is that introduction of substitutions in $V_{29}D_{30}S_{31}$ and/or $I_{290}D_{291}S_{292}$ such as V29A or I290A may be introduced into the corresponding positions of diphtheria toxin fusion proteins and that these substitutions will also have value in further reducing vascular leakage syndrome.

```
(denileukin diftitox-VLM underlined codon encodes for
alanine, here shown as GCT, described in U.S. Pat. No. 8,865,866.)
                                                      SEQ ID NO: 7
   1    ATG

4    GGCGCTGATGATGTTGCTGATTCTTCTAAATCTTTTGTGATGGAAAACTT

54    TTCTTCGTACCACGGGACTAAACCTGGTTATGTAGATTCCATTCAAAAAG

104    GTATACAAAAGCCAAAATCTGGTACACAAGGAAATTATGACGATGATTGG

154    AAAGGGTTTTATAGTACCGACAATAAATACGACGCTGCGGGATACTCTGT

204    AGATAATGAAAACCCGCTCTCTGGAAAAGCTGGAGGCGTGGTCAAAGTGA

254    CGTATCCAGGACTGACGAAGGTTCTCGCACTAAAAGTGGATAATGCCGAA

304    ACTATTAAGAAAGAGTTAGGTTTAAGTCTCACTGAACCGTTGATGGAGCA

354    AGTCGGAACGGAAGAGTTTATCAAAAGGTTCGGTGATGGTGCTTCGCGTG

404    TAGTGCTCAGCCTTCCCTTCGCTGAGGGGAGTTCTAGCGTTGAATATATT

454    AATAACTGGGAACAGGCGAAAGCGTTAAGCGTAGAACTTGAGATTAATTT

504    TGAAACCCGTGGAAAACGTGGCCAAGATGCGATGTATGAGTATATGGCTC

554    AAGCCTGTGCAGGAAATCGTGTCAGGCGATCAGTAGGTAGCTCATTGTCA

604    TGCATCAACCTGGATTGGGATGTTATCCGTGATAAAACTAAAACTAAGAT

654    CGAATCTCTGAAAGAACACGGTCCGATCAAAAACAAAATGAGCGAAAGCC

704    CGAACAAAACTGTATCTGAAGAAAAAGCTAAACAGTACCTGGAAGAATTC

754    CACCAGACTGCACTGGAACACCCGGAACTGTCTGAACTTAAGACCGTTAC

804    TGGTACCAACCCGGTATTCGCTGGTGCTAACTACGCTGCTTGGGCAGTAA

854    ACGTTGCTCAGGTTATCGATAGCGAAACTGCTGATAACCTGGAAAAAACT

904    ACCGCGGCTCTGTCTATCCTGCCGGGTATCGGTAGCGTAATGGGCATCGC

954    AGACGGCGCCGTTCACCACAACACTGAAGAAATCGTTGCACAGTCTATCG

1004    CTCTGAGCTCTCTGATGGTTGCTCAGGCCATCCCGCTGGTAGGTGAACTG

1054    GTTGATATCGGTTTCGCTGCATACAACTTCGTTGAAAGCATCATCAACCT

1104    GTTCCAGGTTGTTCACAACTCTTACAACCGCCCGGCTTACTCTCCGGGTC

1154    ACAAGACGCATGCACCTACTTCTAGCTCTACCAAGAAAACCCAGCTGCAG

1204    CTCGAGCACCTGCTGCTGGATTTGCAGATGATCCTGAACGGTATCAACAA

1254    TTACAAGAACCCGAAACTGACGCGTATGCTGACCTTCAAGTTCTACATGC

1304    CGAAGAAGGCCACCGAACTGAAACACCTGCTGCAGTGTCTAGAAGAAGAA

1354    CTGAAACCGCTGGAGGAAGTTCTGAACCTGGCTCAGTCTAAAAACTTCCA

1404    CCTGCGGCCGCGTGACCTGATCTCTAACATCAACGTAATCGTTCTGGAAC

1454    TGAAGGGCTCTGAAACCACCTTCATGTGTGAATACGCTGATGAGACCGCA

1504    ACCATCGTAGAATTCCTGAACCGTTGGATCACCTTCTGTCAGTCTATCAT

1554    CTCTACCCTGACC                                        < 1566
```

Alignment of DNA sequences comparing SEQ ID NO: 7 [denileukin diftitox-VLM described in U.S. Pat. No. 8,865,866] with SEQ ID NO: 8 [is-denileukin diftitox-VLM of the present invention] demonstrates SEQ ID NO: 8 is missing a codon (three bases) in line 1381-1437.

```
Similarity: 1563/1638 (95.42%)
NO: 7      1    ------------------------------------------------------------      0
                ############################################################
NO: 8      1    GTGAGCAGAAAACTGTTTGCGTCAATCTTAATAGGGGCGCTACTGGGGATAGGGGCCCCA     60

NO: 7      1    ----------ATG--GGCGCTGATGATGTTGCTGATTCTTCTAAATCTTTTGTGATGGAA     48
                ##########|||##|||||||||||||||||||||||||||||||||||||| ||||||
NO: 8     61    CCTTCAGCCCATGCAGGCGCTGATGATGTTGCTGATTCTTCTAAATCTTTTGTGATGGAA    120

NO: 7     49    AACTTTTCTTCGTACCACGGGACTAAACCTGGTTATGTAGATTCCATTCAAAAGGTATA    108
                ||||||||||||||||||||||||||||||||||||||||||||||||||||| ||||||
NO: 8    121    AACTTTTCTTCGTACCACGGGACTAAACCTGGTTATGTAGATTCCATTCAAAAGGTATA    180

NO: 7    109    CAAAAGCCAAAATCTGGTACACAAGGAAATTATGACGATGATTGGAAAGGGTTTTATAGT    168
                ||||||||||||||||||||||||||||||||||||||||||||||||||||| ||||||
NO: 8    181    CAAAAGCCAAAATCTGGTACACAAGGAAATTATGACGATGATTGGAAAGGGTTTTATAGT    240

NO: 7    169    ACCGACAATAAATACGACGCTGCGGGATACTCTGTAGATAATGAAAACCCGCTCTCTGGA    228
                ||||||||||||||||||||||||||||||||||||||||||||||||||||| ||||||
NO: 8    241    ACCGACAATAAATACGACGCTGCGGGATACTCTGTAGATAATGAAAACCCGCTCTCTGGA    300

NO: 7    229    AAAGCTGGAGGCGTGGTCAAAGTGACGTATCCAGGACTGACGAAGGTTCTCGCACTAAAA    288
                ||||||||||||||||||||||||||||||||||||||||||||||||||||| ||||||
NO: 8    301    AAAGCTGGAGGCGTGGTCAAAGTGACGTATCCAGGACTGACGAAGGTTCTCGCACTAAAA    360

NO: 7    289    GTGGATAATGCCGAAACTATTAAGAAAGAGTTAGGTTTAAGTCTCACTGAACCGTTGATG    348
                ||||||||||||||||||||||||||||||||||||||||||||||||||||| ||||||
NO: 8    361    GTGGATAATGCCGAAACTATTAAGAAAGAGTTAGGTTTAAGTCTCACTGAACCGTTGATG    420

NO: 7    349    GAGCAAGTCGGAACGGAAGAGTTTATCAAAAGGTTCGGTGATGGTGCTTCGCGTGTAGTG    408
                ||||||||||||||||||||||||||||||||||||||||||||||||||||| ||||||
NO: 8    421    GAGCAAGTCGGAACGGAAGAGTTTATCAAAAGGTTCGGTGATGGTGCTTCGCGTGTAGTG    480

NO: 7    409    CTCAGCCTTCCCTTCGCTGAGGGGAGTTCTAGCGTTGAATATATTAATAACTGGGAACAG    468
                ||||||||||||||||||||||||||||||||||||||||||||||||||||| ||||||
NO: 8    481    CTCAGCCTTCCCTTCGCTGAGGGGAGTTCTAGCGTTGAATATATTAATAACTGGGAACAG    540

NO: 7    469    GCGAAAGCGTTAAGCGTAGAACTTGAGATTAATTTTGAAACCCGTGGAAAACGTGGCCAA    528
                ||||||||||||||||||||||||||||||||||||||||||||||||||||| ||||||
NO: 8    541    GCGAAAGCGTTAAGCGTAGAACTTGAGATTAATTTTGAAACCCGTGGAAAACGTGGCCAA    600

NO: 7    529    GATGCGATGTATGAGTATATGGCTCAAGCCTGTGCAGGAAATCGTGTCAGGCGATCAGTA    588
                ||||||||||||||||||||||||||||||||||||||||||||||||||||| ||||||
NO: 8    601    GATGCGATGTATGAGTATATGGCTCAAGCCTGTGCAGGAAATCGTGTCAGGCGATCAGTA    660

NO: 7    589    GGTAGCTCATTGTCATGCATCAACCTGGATTGGGATGTTATCCGTGATAAAACTAAAACT    648
                ||||||||||||||||||||||||||||||||||||||||||||||||||||| ||||||
NO: 8    661    GGTAGCTCATTGTCATGCATCAACCTGGATTGGGATGTTATCCGTGATAAAACTAAAACT    720

NO: 7    649    AAGATCGAATCTCTGAAAGAACACGGTCCGATCAAAAACAAAATGAGCGAAAGCCCGAAC    708
                ||||||||||||||||||||||||||||||||||||||||||||||||||||| ||||||
NO: 8    721    AAGATCGAATCTCTGAAAGAACACGGTCCGATCAAAAACAAAATGAGCGAAAGCCCGAAC    780

NO: 7    709    AAAACTGTATCTGAAGAAAAAGCTAAACAGTACCTGGAAGAATTCCACCAGACTGCACTG    768
                ||||||||||||||||||||||||||||||||||||||||||||||||||||| ||||||
NO: 8    781    AAAACTGTATCTGAAGAAAAAGCTAAACAGTACCTGGAAGAATTCCACCAGACTGCACTG    840

NO: 7    769    GAACACCCGGAACTGTCTGAACTTAAGACCGTTACTGGTACCAACCCGGTATTCGCTGGT    828
                ||||||||||||||||||||||||||||||||||||||||||||||||||||| ||||||
NO: 8    841    GAACACCCGGAACTGTCTGAACTTAAGACCGTTACTGGTACCAACCCGGTATTCGCTGGT    900

NO: 7    829    GCTAACTACGCTGCTTGGGCAGTAAACGTTGCTCAGGTTATCGATAGCGAAACTGCTGAT    888
                ||||||||||||||||||||||||||||||||||||||||||||||||||||| ||||||
NO: 8    901    GCTAACTACGCTGCTTGGGCAGTAAACGTTGCTCAGGTTATCGATAGCGAAACTGCTGAT    960

NO: 7    889    AACCTGGAAAAAACTACCGCGGCTCTGTCTATCCTGCCGGGTATCGGTAGCGTAATGGGC    948
                ||||||||||||||||||||||||||||||||||||||||||||||||||||| ||||||
NO: 8    961    AACCTGGAAAAAACTACCGCGGCTCTGTCTATCCTGCCGGGTATCGGTAGCGTAATGGGC   1020
```

```
                                                 -continued
NO: 7    949   ATCGCAGACGGCGCCGTTCACCACAACACTGAAGAAATCGTTGCACAGTCTATCGCTCTG   1008
               ||||||||||||||||||||||||||||||||||||||||||||||||||||||| ||||||
NO: 8   1021   ATCGCAGACGGCGCCGTTCACCACAACACTGAAGAAATCGTTGCACAGTCTATCGCTCTG   1080

NO: 7   1009   AGCTCTCTGATGGTTGCTCAGGCCATCCCGCTGGTAGGTGAACTGGTTGATATCGGTTTC   1068
               ||||||||||||||||||||||||||||||||||||||||||||||||||||||| ||||||
NO: 8   1081   AGCTCTCTGATGGTTGCTCAGGCCATCCCGCTGGTAGGTGAACTGGTTGATATCGGTTTC   1140

NO: 7   1069   GCTGCATACAACTTCGTTGAAAGCATCATCAACCTGTTCCAGGTTGTTCACAACTCTTAC   1128
               ||||||||||||||||||||||||||||||||||||||||||||||||||||||| ||||||
NO: 8   1141   GCTGCATACAACTTCGTTGAAAGCATCATCAACCTGTTCCAGGTTGTTCACAACTCTTAC   1200

NO: 7   1129   AACCGCCCGGCTTACTCTCCGGGTCACAAGACGCATGCACCTACTTCTAGCTCTACCAAG   1188
               ||||||||||||||||||||||||||||||||||||||||||||||||||||||| ||||||
NO: 8   1201   AACCGCCCGGCTTACTCTCCGGGTCACAAGACGCATGCACCTACTTCTAGCTCTACCAAG   1260

NO: 7   1189   AAAACCCAGCTGCAGCTCGAGCACCTGCTGCTGGATTTGCAGATGATCCTGAACGGTATC   1248
               ||||||||||||||||||||||||||||||||||||||||||||||||||||||| ||||||
NO: 8   1261   AAAACCCAGCTGCAGCTCGAGCACCTGCTGCTGGATTTGCAGATGATCCTGAACGGTATC   1320

NO: 7   1249   AACAATTACAAGAACCCGAAACTGACGCGTATGCTGACCTTCAAGTTCTACATGCCGAAG   1308
               ||||||||||||||||||||||||||||||||||||||||||||||||||||||| ||||||
NO: 8   1321   AACAATTACAAGAACCCGAAACTGACGCGTATGCTGACCTTCAAGTTCTACATGCCGAAG   1380

NO: 7   1309   AAGGCCACCGAACTGAAACACCTGCTGCAGTGTCTAGAAGAAGAACTGAAACCGCTGGAG   1368
               |||||||||||||||||||||||||###|||||||||||||||||||||||||| ||||||
NO: 8   1381   AAGGCCACCGAACTGAAACACCTGC---AGTGTCTAGAAGAAGAACTGAAACCGCTGGAG   1437

NO: 7   1369   GAAGTTCTGAACCTGGCTCAGTCTAAAAACTTCCACCTGCGGCCGCGTGACCTGATCTCT   1428
               ||||||||||||||||||||||||||||||||||||||||||||||||||||||| ||||||
NO: 8   1438   GAAGTTCTGAACCTGGCTCAGTCTAAAAACTTCCACCTGCGGCCGCGTGACCTGATCTCT   1497

NO: 7   1429   AACATCAACGTAATCGTTCTGGAACTGAAGGGCTCTGAAACCACCTTCATGTGTGAATAC   1488
               ||||||||||||||||||||||||||||||||||||||||||||||||||||||| ||||||
NO: 8   1498   AACATCAACGTAATCGTTCTGGAACTGAAGGGCTCTGAAACCACCTTCATGTGTGAATAC   1557

NO: 7   1489   GCTGATGAGACCGCAACCATCGTAGAATTCCTGAACCGTTGGATCACCTTCTGTCAGTCT   1548
               ||||||||||||||||||||||||||||||||||||||||||||||||||||||| ||||||
NO: 8   1558   GCTGATGAGACCGCAACCATCGTAGAATTCCTGAACCGTTGGATCACCTTCTGTCAGTCT   1617

NO: 7   1549   ATCATCTCTACCCTGACC---                                         1566
               |||||||||||||||||||###
NO: 8   1618   ATCATCTCTACCCTGACCTGA                                         1638

(DNA sequence IL-2 portion of denileukin diftitox)
                                                                          SEQ ID NO: 9
    1          GCACCTACTTCTAGCTCTACCAAGAAAACCCAGCTGCAGCTCGAGCACCT

51          GCTGCTGGATTTGCAGATGATCCTGAACGGTATCAACAATTACAAGAACC

101          CGAAACTGACGCGTATGCTGACCTTCAAGTTCTACATGCCGAAGAAGGCC

151          ACCGAACTGAAACACCTGCAGTGTCTAGAAGAAGAACTGAAACCGCTGGA

201          GGAAGTTCTGAACCTGGCTCAGTCTAAAAACTTCCACCTGCGGCCGCGTG

251          ACCTGATCTCTAACATCAACGTAATCGTTCTGGAACTGAAGGGCTCTGAA

301          ACCACCTTCATGTGTGAATACGCTGATGAGACCGCAACCATCGTAGAATT

351          CCTGAACCGTTGGATCACCTTCTGTCAGTCTATCATCTCTACCCTGACCT

401          GA                                                           < 402
```

Proteins Produced Using DNA Expression Vectors of the Present Invention

The first amino acid of a mature active diphtheria toxin related fusion protein of the present invention is a glycine as shown in bold (amino acid 1) in SEQ ID NO: 13 and 15. The signal sequence within SEQ ID NO: 4 is labeled with negative numbers, counting back from the first glycine of the mature fusion protein and has the following amino acid sequence MSRKLFASILIGALLGIGAPPSAHA (SEQ ID NO: 22). The signal sequence is shown in SEQ ID NOs: 11 and 12 and is underlined. The mature secreted diphtheria toxin fusion protein includes a diphtheria toxin portion, such as $Gly_1$-$His_{387}$, and a target receptor binding domain, such as an IL-2 protein from $Ala_{388}$-$Thr_{520}$ in SEQ ID NO: 3. Other target receptor binding domains used in the present invention that may be fused to a diphtheria toxin protein (or functional part thereof) include IL-3, IL-4, IL-6, IL-7, IL-15, EGF, FGF, substance P, CD4, αMSH, GRP, TT fragment C, GCSF, heregulin β1, TNFα, TGFβ, among others, or a combination thereof. SEQ ID NO: 10 describes c-denileukin diftitox that is not secreted and is requires purification from inclusion bodies in E. coli. SEQ ID NO: 12 describes immature secreted is-denileukin diftitox with a signal sequence. SEQ ID NO: 13 describes MS-denileukin diftitox wherein the signal sequence has been cleaved off during the process of secretion to the extracellular space.

(Protein Sequence of c-denileukin diftitox known as Ontak ®)
SEQ ID NO: 10

1 MGADDVVDSSKSFVMENFSSYHGTKP

27 GYVDSIQKGIQKPKSGTQGNYDDDWKGFYSTDNKYDAAGYSVDNENPLSG

77 KAGGVVKVTYPGLTKVLALKVDNAETIKKELGLSLTEPLMEQVGTEEFIK

127 RFGDGASRVVLSLPFAEGSSSVEYINNWEQAKALSVELEINFETRGKRGQ

177 DAMYEYMAQACAGNRVRRSVGSSLSCINLDWDVIRDKTKTKIESLKEHGP

227 IKNKMSESPNKTVSEEKAKQYLEEFHQTALEHPELSELKTVTGTNPVFAG

277 ANYAAWAVNVAQVIDSETADNLEKTTAALSILPGIGSVMGIADGAVHHNT

327 EEIVAQSIALSSLMVAQAIPLVGELVDIGFAAYNFVESIINLFQVVHNSY

377 NRPAYSPGHKTHAPTSSSTKKTQLQLEHLLLDLQMILNGINNYKNPKLTR

427 MLTFKFYMPKKATELKHLQCLEEELKPLEEVLNLAQSKNFHLRPRDLISN

477 INVIVLELKGSETTFMCEYADETATIVEFLNRWITFCQSIISTLT <521

(w-diphtheria toxin)

SEQ ID NO: 11

1 MSRKLFASILIGALLGIGAPPSAHAGADDVVDSSKSFVMENFSSYHGTKP

51 GYVDSIQKGIQKPKSGTQGNYDDDWKGFYSTDNKYDAAGYSVDNENPLSG

101 KAGGVVKVTYPGLTKVLALKVDNAETIKKELGLSLTEPLMEQVGTEEFIK

151 RFGDGASRVVLSLPFAEGSSSVEYINNWEQAKALSVELEINFETRGKRGQ

201 DAMYEYMAQACAGNRVRRSVGSSLSCINLDWDVIRDKTKTKIESLKEHGP

251 IKNKMSESPNKTVSEEKAKQYLEEFHQTALEHPELSELKTVTGTNPVFAG

301 ANYAAWAVNVAQVIDSETADNLEKTTAALSILPGIGSVMGIADGAVHHNT

351 EEIVAQSIALSSLMVAQAIPLVGELVDIGFAAYNFVESIINLFQVVHNSY

401 NRPAYSPGHKTQPFLHDGYAVSWNTVEDSIIRTGFQGESGHDIKITAENT

451 PLPIAGVLLPTIPGKLDVNKSKTHISVNGRKIRMRCRAIDGDVTFCRPKS

501 PVYVGNGVHANLHVAFHRSSSEKIHSNEISSDSIGVLGYQKTVDHTKVNS

551 KLSLFFEIKS <560

(is-denileukin diftitox)

SEQ ID NO: 12

-25 MSRKLFASILIGALLGIGAPPSAHAGADDVVDSSKSFVMENFSSYHGTKP

26 GYVDSIQKGIQKPKSGTQGNYDDDWKGFYSTDNKYDAAGYSVDNENPLSG

76 KAGGVVKVTYPGLTKVLALKVDNAETIKKELGLSLTEPLMEQVGTEEFIK

126 RFGDGASRVVLSLPFAEGSSSVEYINNWEQAKALSVELEINFETRGKRGQ

176 DAMYEYMAQACAGNRVRRSVGSSLSCINLDWDVIRDKTKTKIESLKEHGP

226 IKNKMSESPNKTVSEEKAKQYLEEFHQTALEHPELSELKTVTGINPVFAG

276 ANYAAWAVNVAQVIDSETADNLEKTTAALSILPGIGSVMGIADGAVHHNT

326 EEIVAQSIALSSLMVAQAIPLVGELVDIGFAAYNFVESIINLFQVVHNSY

376 NRPAYSPGHKTHAPTSSSTKKTQLQLEHLLLDLQMILNGINNYKNPKLTR

426 MLTFKFYMPKKATELKHLQCLEEELKPLEEVLNLAQSKNFHLRPRDLISN

476 INVIVLELKGSETTFMCEYADETATIVEFLNRWITFCQSIISILT <520

(ms-denileukin diftitox)

SEQ ID NO: 13

1 GADDVVDSSKSFVMENFSSYHGTKP

26 GYVDSIQKGIQKPKSGTQGNYDDDWKGFYSTDNKYDAAGYSVDNENPLSG

76 KAGGVVKVTYPGLTKVLALKVDNAETIKKELGLSLTEPLMEQVGTEEFIK

| | |
|---|---|
| 126 | RFGDGASRVVLSLPFAEGSSSVEYINNWEQAKALSVELEINFETRGKRGQ |
| 176 | DAMYEYMAQACAGNRVRRSVGSSLSCINLDWDVIRDKTKTKIESLKEHGP |
| 226 | IKNKMSESPNKTVSEEKAKQYLEEFHQTALEHPELSELKTVTGINPVFAG |
| 276 | ANYAAWAVNVAQVIDSETADNLEKTTAALSILPGIGSVMGIADGAVHHNT |
| 326 | EEIVAQSIALSSLMVAQAIPLVGELVDIGFAAYNFVESIINLFQVVHNSY |
| 376 | NRPAYSPGHKTHAPTSSSTKKTQLQLEHLLLDLQMILNGINNYKNPKLTR |
| 426 | MLTFKFYMPKKATELKHLQCLEEELKPLEEVLNLAQSKNFHLRPRDLISN |
| 476 | INVIVLELKGSETTFMCEYADETATIVEFLNRWITFCQSIISILT <520 |

(Protein sequence of is-denileukin diftitox-VLM)

SEQ ID NO: 14

| | |
|---|---|
| -25 | <u>MSRKLFASILIGALLGIGAPPSAHA</u>GADDVADSSKSFVMENFSSYHGTKP |
| 26 | GYVDSIQKGIQKPKSGTQGNYDDDWKGFYSTDNKYDAAGYSVDNENPLSG |
| 76 | KAGGVVKVTYPGLTKVLALKVDNAETIKKELGLSLTEPLMEQVGTEEFIK |
| 126 | RFGDGASRVVLSLPFAEGSSSVEYINNWEQAKALSVELEINFETRGKRGQ |
| 176 | DAMYEYMAQACAGNRVRRSVGSSLSCINLDWDVIRDKTKTKIESLKEHGP |
| 226 | IKNKMSESPNKTVSEEKAKQYLEEFHQTALEHPELSELKTVTGINPVFAG |
| 276 | ANYAAWAVNVAQVIDSETADNLEKTTAALSILPGIGSVMGIADGAVHHNT |
| 326 | EEIVAQSIALSSLMVAQAIPLVGELVDIGFAAYNFVESIINLFQVVHNSY |
| 376 | NRPAYSPGHKTHAPTSSSTKKTQLQLEHLLLDLQMILNGINNYKNPKLTR |
| 426 | MLTFKFYMPKKATELKHLQCLEEELKPLEEVLNLAQSKNFHLRPRDLISN |
| 476 | INVIVLELKGSETTFMCEYADETATIVEFLNRWITFCQSIISILT <520 |

(Protein sequence of ms-denileukin diftitox-VLM)

SEQ ID NO: 15

| | |
|---|---|
| 1 | GADDVADSSKSFVMENFSSYHGTKP |
| 26 | GYVDSIQKGIQKPKSGTQGNYDDDWKGFYSTDNKYDAAGYSVDNENPLSG |
| 76 | KAGGVVKVTYPGLTKVLALKVDNAETIKKELGLSLTEPLMEQVGTEEFIK |
| 126 | RFGDGASRVVLSLPFAEGSSSVEYINNWEQAKALSVELEINFETRGKRGQ |
| 176 | DAMYEYMAQACAGNRVRRSVGSSLSCINLDWDVIRDKTKTKIESLKEHGP |
| 226 | IKNKMSESPNKTVSEEKAKQYLEEFHQTALEHPELSELKTVTGINPVFAG |
| 276 | ANYAAWAVNVAQVIDSETADNLEKTTAALSILPGIGSVMGIADGAVHHNT |
| 326 | EEIVAQSIALSSLMVAQAIPLVGELVDIGFAAYNFVESIINLFQVVHNSY |
| 376 | NRPAYSPGHKTHAPTSSSTKKTQLQLEHLLLDLQMILNGINNYKNPKLTR |
| 426 | MLTFKFYMPKKATELKHLQCLEEELKPLEEVLNLAQSKNFHLRPRDLISN |
| 476 | INVIVLELKGSETTFMCEYADETATIVEFLNRWITFCQSIISILT <520 |

(Protein sequence of denileukin diftitox-VLM described in U.S. Pat. No. 8,865,866)

SEQ ID NO: 16

| | |
|---|---|
| 1 | MGADDVADSSKSFVMENFSSYHGTKP |
| 27 | GYVDSIQKGIQKPKSGTQGNYDDDWKGFYSTDNKYDAAGYSVDNENPLSG |
| 77 | KAGGVVKVTYPGLTKVLALKVDNAETIKKELGLSLTEPLMEQVGTEEFIK |
| 127 | RFGDGASRVVLSLPFAEGSSSVEYINNWEQAKALSVELEINFETRGKRGQ |
| 177 | DAMYEYMAQACAGNRVRRSVGSSLSCINLDWDVIRDKTKTKIESLKEHGP |
| 227 | IKNKMSESPNKTVSEEKAKQYLEEFHQTALEHPELSELKTVTGTNPVFAG |
| 277 | ANYAAWAVNVAQVIDSETADNLEKTTAALSILPGIGSVMGIADGAVHHNT |

```
327    EEIVAQSIALSSLMVAQAIPLVGELVDIGFAAYNFVESIINLFQVVHNSY

377    NRPAYSPGHKTHAPTSSSTKKTQLQLEHLLLDLQMILNGINNYKNPKLTR

427    MLTFKFYMPKKATELKHLLQCLEEELKPLEEVLNLAQSKNFHLRPRDLIS

477    NINVIVLELKGSETTFMCEYADETATIVEFLNRWITFCQSISILT           <522
```

Protein Alignment of SEQ ID NO: 16 is denileukin diftitox-VLM described in U.S. Pat. No. 8,865,866 that has an extra amino acid (L) at position 445 when compared with SEQ ID NO: 14 is-denileukin diftitox-VLM of the present invention.

```
Similarity: 521/522 (99.81%)
NO: 16    1    M----------------------GADDVADSSKSFVMENFSSYHGTKPGYVDSIQKGI    36
               |####################|||||||||||||||||||||||||| ||||||
NO: 14    1    MSRKLFASILIGALLGIGAPPSAHAGADDVADSSKSFVMENFSSYHGTKPGYVDSIQKGI  60

NO: 16   37    QKPKSGTQGNYDDDWKGFYSTDNKYDAAGYSVDNENPLSGKAGGVVKVTYPGLTKVLALK   96
               |||||||||||||||||||||||||||||||||||||||||||||||||||| ||||||
NO: 14   61    QKPKSGTQGNYDDDWKGFYSTDNKYDAAGYSVDNENPLSGKAGGVVKVTYPGLTKVLALK  120

NO: 16   97    VDNAETIKKELGLSLTEPLMEQVGTEEFIKRFGDGASRVVLSLPFAEGSSSVEYINNWEQ  156
               |||||||||||||||||||||||||||||||||||||||||||||||||||| ||||||
NO: 14  121    VDNAETIKKELGLSLTEPLMEQVGTEEFIKRFGDGASRVVLSLPFAEGSSSVEYINNWEQ  180

NO: 16  157    AKALSVELEINFETRGKRGQDAMYEYMAQACAGNRVRRSVGSSLSCINLDWDVIRDKTKT  216
               |||||||||||||||||||||||||||||||||||||||||||||||||||| ||||||
NO: 14  181    AKALSVELEINFETRGKRGQDAMYEYMAQACAGNRVRRSVGSSLSCINLDWDVIRDKTKT  240

NO: 16  217    KIESLKEHGPIKNKMSESPNKTVSEEKAKQYLEEFHQTALEHPELSELKTVTGTNPVFAG  276
               |||||||||||||||||||||||||||||||||||||||||||||||||||| ||||||
NO: 14  241    KIESLKEHGPIKNKMSESPNKTVSEEKAKQYLEEFHQTALEHPELSELKTVTGTNPVFAG  300

NO: 16  277    ANYAAWAVNVAQVIDSETADNLEKTTAALSILPGIGSVMGIADGAVHHNTEEIVAQSIAL  336
               |||||||||||||||||||||||||||||||||||||||||||||||||||| ||||||
NO: 14  301    ANYAAWAVNVAQVIDSETADNLEKTTAALSILPGIGSVMGIADGAVHHNTEEIVAQSIAL  360

NO: 16  337    SSLMVAQAIPLVGELVDIGFAAYNFVESIINLFQVVHNSYNRPAYSPGHKTHAPTSSSTK  396
               |||||||||||||||||||||||||||||||||||||||||||||||||||| ||||||
NO: 14  361    SSLMVAQAIPLVGELVDIGFAAYNFVESIINLFQVVHNSYNRPAYSPGHKTHAPTSSSTK  420

NO: 16  397    KTQLQLEHLLLDLQMILNGINNYKNPKLTRMLTFKFYMPKKATELKHLLQCLEEELKPLE  456
               |||||||||||||||||||||||||||||||||||||||||||||#|||| ||||||
NO: 14  421    KTQLQLEHLLLDLQMILNGINNYKNPKLTRMLTFKFYMPKKATELKHL-QCLEEELKPLE  479

NO: 16  457    EVLNLAQSKNFHLRPRDLISNINVIVLELKGSETTFMCEYADETATIVEFLNRWITFCQS  516
               |||||||||||||||||||||||||||||||||||||||||||||||||||| ||||||
NO: 14  480    EVLNLAQSKNFHLRPRDLISNINVIVLELKGSETTFMCEYADETATIVEFLNRWITFCQS  539

NO: 16  517    IISTLT                                                        522
               ||||||
NO: 14  540    IISTLT                                                        545
```

Use of DNA Expression Vectors to Manufacture Proteins.

The method using Fe-independent, secreted expression of proteins related to diphtheria toxin described above has several commercial applications in addition to the use of the method to express s-denileukin diftitox. The method can be used to improve (enhance) expression (yield) of:

WT Diphtheria Toxin:

The wild type Diphtheria toxin (SEQ ID NO: 11) used to make diphtheria toxOid, a vaccine for diphtheria which is present in DTP, TDaP, and other combination vaccines may be made using the DNA expression vector of the present invention. The DNA segment encoding SEQ ID NO: 11 may be placed in the DNA expression vector of the present invention and located downstream of the ToxP/mutant ToxO.

Cross-Reacting Material-197 (CRM197) and Cross-Reacting Material-107 (CRM107):

CRM197 and CR107 are mutant proteins of full-length diphtheria toxin which are highly immunogenic but are completely devoid of toxin activity. They are used as carriers for several polysaccharide conjugate vaccines. For example, Wyeth and Pfizer took advantage of this immunogenicity in the 1990s when it conjugated seven polysaccharides from *Streptococcus pneumoniae* to CRM197 to create the original Prevnar vaccine which was FDA approved in February 2000. A 13-polysaccharides Prevnar was FDA-approved in 2010. The meningococcal vaccine Menveo, from Novartis, is four *Neisseria meningitidis* polysaccharides plus CRM197. This vaccine gained FDA approval in 2010. The cancer immunotherapy company Imugene (ASX: IMU) reported dramatic improvements in antibody titers from its B cell peptide cancer immunotherapy targeting HER2 when it used CRM197 as a carrier protein. CRM197 is also being evaluated as a potential drug delivery protein. The Swiss-based Turing Pharmaceuticals is working on CRM197 fusion constructs with therapeutic proteins of up to 1,000 amino acids in length. The DNA expression vectors of the present invention maybe used to produce CRM 197 and CRM 107. One or more of the DNA segment(s) encoding SEQ ID NOs: 18-21 may be placed in the DNA expression vector of the present invention and located downstream of the ToxP/mutant ToxO.

Diphtheria Toxin Based Fusion Proteins with Cleavable Peptide or Protein Tags Used to Enhance Purification.

Cleavable peptide tags (such as His$_6$ (SEQ ID NO: 23) or FLAG [DYKDDDDK] (SEQ ID NO: 24)) or protein tags (such as GST [glutathione 5-transferase] or SUMO [Small Ubiquitin-like Modifier protein]) may be fused with specific protease cleavage sites to diphtheria toxin based fusion proteins. Affinity chromatography methods using antibodies or ligands which bind to the tag may be used for rapid purification of the tagged protein. Following purification, the specific cleavage site enables separation of the tag from the desired diphtheria toxin related proteins. Such fusions may enhance purification of diphtheria toxin based fusion proteins of the present invention.

```
(Protein sequence of ms-CRM197)
                                                                SEQ ID NO: 17
    1    GADDVVDSSKSFVMENFSSYHGTKPGYVDSIQKGIQKPKSGTQGNYDDDW
   51    KEFYSTDNKYDAAGYSVDNENPLSGKAGGVVKVTYPGLTKVLALKVDNAE
  101    TIKKELGLSLTEPLMEQVGTEEFIKRFGDGASRVVLSLPFAEGSSSVEYI
  151    NNWEQAKALSVELEINFETRGKRGQDAMYEYMAQACAGNRVRRSVGSSLS
  201    CINLDWDVIRDKIKTKIESLKEHGPIKNKMSESPNKTVSEEKAKQYLEEF
  251    HQTALEHPELSELKTVIGINPVFAGANYAAWAVNVAQVIDSETADNLEKT
  301    TAALSILPGIGSVMGIADGAVHHNTEEIVAQSIALSSLMVAQAIPLVGEL
  351    VDIGFAAYNFVESIINLFQVVHNSYNRPAYSPGHKTQPFLHDGYAVSWNT
  401    VEDSIIRTGFQGESGHDIKITAENTPLPIAGVLLPTIPGKLDVNKSKTHI
  451    SVNGRKIRMRCRAIDGDVTFCRPKSPVYVGNGVHANLHVAFHRSSSEKIH
  501    SNEISSDSIGVLGYQKTVDHTKVNSKLSLFFEIKS              <535

(Protein sequence of is-CRM197)
                                                                SEQ ID NO: 18
    1    MSRKLFASILIGALLGIGAPPSAHAGADDVVDSSKSFVMENFSSYHGTKP
   51    GYVDSIQKGIQKPKSGTQGNYDDDWKEFYSIDNKYDAAGYSVDNENPLSG
  101    KAGGVVKVTYPGLIKVLALKVDNAETIKKELGLSLTEPLMEQVGTEEFIK
  151    RFGDGASRVVLSLPFAEGSSSVEYINNWEQAKALSVELEINFETRGKRGQ
  201    DAMYEYMAQACAGNRVRRSVGSSLSCINLDWDVIRDKIKTKIESLKEHGP
  251    IKNKMSESPNKTVSEEKAKQYLEEFHQTALEHPELSELKTVIGINPVFAG
  301    ANYAAWAVNVAQVIDSETADNLEKTTAALSILPGIGSVMGIADGAVHHNT
  351    EEIVAQSIALSSLMVAQAIPLVGELVDIGFAAYNFVESIINLFQVVHNSY
  401    NRPAYSPGHKTQPFLHDGYAVSWNIVEDSIIRTGFQGESGHDIKITAENT
  451    PLPIAGVLLPTIPGKLDVNKSKTHISVNGRKIRMRCRAIDGDVTFCRPKS
  501    PVYVGNGVHANLHVAFHRSSSEKIHSNEISSDSIGVLGYQKTVDHTKVNS
  551    KLSLFFEIKS                                      <560

(Protein sequence of ms-CRM107)
                                                                SEQ ID NO: 19
         GADDVVDSSKSFVMENFSSYHGTKP
   51    GYVDSIQKGIQKPKSGTQGNYDDDWKGFYSIDNKYDAAGYSVDNENPLSG
  101    KAGGVVKVTYPGLIKVLALKVDNAETIKKELGLSLTEPLMEQVGTEEFIK
  151    RFGDGASRVVLSLPFAEGSSSVEYINNWEQAKALSVELEINFETRGKRGQ
  201    DAMYEYMAQACAGNRVRRSVGSSLSCINLDWDVIRDKIKTKIESLKEHGP
  251    IKNKMSESPNKTVSEEKAKQYLEEFHQTALEHPELSELKTVIGINPVFAG
  301    ANYAAWAVNVAQVIDSETADNLEKTTAALSILPGIGSVMGIADGAVHHNT
  351    EEIVAQSIALSSLMVAQAIPLVGELVDIGFAAYNFVESIINLFQVVHNSY
  401    NRPAYSPGHKTQPFFHDGYAVSWNIVEDSIIRTGFQGESGHDIKITAENT
  451    PLPIAGVLLPTIPGKLDVNKSKTHISVNGRKIRMRCRAIDGDVTFCRPKS
```

```
501  PVYVGNGVHANLHVAFHRSSSEKIHSNEISSDSIGVLGYQKTVDHTKVNF

551  KLSLFFEIKS                                              <560
```

(Protein sequence of is-CRM107)

SEQ ID NO: 20

```
  1  MSRKLFASILIGALLGIGAPPSAHAGADDVVDSSKSFVMENFSSYHGTKP

51  GYVDSIQKGIQKPKSGTQGNYDDDWKGFYSIDNKYDAAGYSVDNENPLSG

101  KAGGVVKVTYPGLIKVLALKVDNAETIKKELGLSLTEPLMEQVGTEEFIK

151  RFGDGASRVVLSLPFAEGSSSVEYINNWEQAKALSVELEINFETRGKRGQ

201  DAMYEYMAQACAGNRVRRSVGSSLSCINLDWDVIRDKIKTKIESLKEHGP

251  IKNKMSESPNKTVSEEKAKQYLEEFHQTALEHPELSELKTVIGINPVFAG

301  ANYAAWAVNVAQVIDSETADNLEKTTAALSILPGIGSVMGIADGAVHHNT

351  EEIVAQSIALSSLMVAQAIPLVGELVDIGFAAYNFVESIINLFQVVHNSY

401  NRPAYSPGHKTQPFFHDGYAVSWNIVEDSIIRTGFQGESGHDIKITAENT

451  PLPIAGVLLPTIPGKLDVNKSKTHISVNGRKIRMRCRAIDGDVTFCRPKS

501  PVYVGNGVHANLHVAFHRSSSEKIHSNEISSDSIGVLGYQKTVDHTKVNF

551  KLSLFFEIKS                                              <560
```

TABLE 1

| SEQUENCE NUMBER | DESCRIPTION |
| --- | --- |
| SEQ ID NO: 38 | Protein sequence of N terminal His tag to VLM s-Ontak |
| SEQ ID NO: 39 | Protein sequence of N terminal His tag to VLM s-Ontak after signal sequence is cleaved |
| SEQ ID NO: 40 | Protein sequence of N terminal His tag to VLM s-Ontak after signal sequence is cleaved and TEV site is cleaved |
| SEQ ID NO: 41 | DNA sequence of N terminal His tag to VLM s-Ontak |
| SEQ ID NO: 42 | Protein sequence of C terminal His tag to VLM s-Ontak |
| SEQ ID NO: 43 | Protein sequence of C terminal His tag to VLM s-Ontak after signal sequence is cleaved) |
| SEQ ID NO: 44 | DNA sequence of C terminal His tag to VLM s-Ontak |
| SEQ ID NO: 45 | Protein sequence of C terminal TEV His9 tag to VLM s-Ontak ("His9" disclosed as SEQ ID NO: 48) |
| SEQ ID NO: 46 | Protein sequence of C terminal TEV His9 tag to VLM s-Ontak after signal sequence is cleaved ("His9" disclosed as SEQ ID NO: 48) |
| SEQ ID NO: 30 | Protein sequence of C terminal TEV His9 tag to VLM s-Ontak after signal sequence and Tev protease site are cleaved ("His9" disclosed as SEQ ID NO: 48) |
| SEQ ID NO: 31 | DNA sequence of C terminal His tag to VLM s-Ontak |
| SEQ ID NO: 32 | Secreted *C. diphtheriae* protease 1 amino acid sequence |
| SEQ ID NO: 33 | Secreted *C. diphtheriae* protease 1 DNA sequence |
| SEQ ID NO: 34 | DNA sequence of allelic exchange substrate [AES] for knocking out Secreted *C. diphtheriae* protease 1 |
| SEQ ID NO: 35 | Secreted *C. diphtheriae* protease 2 amino acid sequence |
| SEQ ID NO: 36 | Secreted *C. diphtheriae* protease 2 DNA sequence) Protease 2 DNA sequence |
| SEQ ID NO: 37 | DNA sequence of allelic exchange substrate [AES] for knocking out Secreted *C. diphtheriae* protease 2 |

Purification of VLM s-Ontak Using His-Tagged Versions of the Polypeptide

In some preparations of VLM s-Ontak produced in *Corynebacterium diphtheriae* C7 slow proteolytic cleavage of the mature 520 amino acid polypeptide occurs. This is probably due to secreted proteases made by *Corynebacterium diphtheriae* C7. This proteolytic cleavage occurs at approximately amino acid 390 of the mature 520 amino acid VLM s-Ontak.

Histidine-tagged (His-tagged) versions of VLM s-Ontak have been constructed for the purpose of accelerating the purification of the desired protein away from the secreted proteases present in the culture supernatant. Tobacco Etch Virus (TEV) nuclear-inclusion-a endopeptidase (EC 3.4.22.44) recognition sites have also been engineered into these His-tagged versions of VLM s-Ontak. The purpose of the TEV cleavage sites is to enable the removal of the poly-His sequences in the final preparation of VLM s-Ontak. TEV is a highly specific endopeptidase which recognizes the amino acid sequence ENLYFQ\X where '\' denotes the cleaved peptide bond, and X represents any small hydrophobic or polar amino acid such as glycine (G).

N-Terminal His-Tagged VLM s-Ontak with TEV Cleavage Site.

As shown in SEQ ID: 38 (Protein sequence of N terminal His tag to VLM s-Ontak) it is possible to add the amino acid sequence HHHHHHENLYFQ to the immature protein sequence of VLM s-Ontak near its N-terminus. In this version, the sequence HHHHHHENLYFQ appears immediately after the 26 amino acid signal sequence and immediately before the mature sequence of VLM s-Ontak (GAD-DVA . . . ). The first glycine of VLM s-Ontak comprises the final recognition residue for the TEV protease which recognizes ENLYFQ\X with X being any small amino acid. The mature, secreted protein sequence of this N-terminal His-tagged VLM s-Ontak is shown in SEQ ID: 39 (Protein sequence of N terminal His tag to VLM s-Ontak after signal sequence is cleaved) which is a good candidate for Nickel-column affinity purification with its $His_6$ tag. The affinity purified VLM s-Ontak may then be exposed to small amounts of pure TEV protease, leading to enzymatic proteolysis that removes the 13 N-terminal residues MHHHHHHENLYFQ and releases mature, untagged VLM s-Ontak as is shown in SEQ ID: 40 (Protein sequence of N terminal His tag to VLM s-Ontak after signal sequence is cleaved and TEV site is cleaved).

Because the secreted protease(s) of *Corynebacterium diphtheriae* C7 cleave at approximately amino acid 390, N-terminal His-tagging can lead to two species: full length desired VLM s-Ontak (520 amino acids) and a 390-amino acid N-terminal breakdown fragment. These two polypeptides, being relatively close in size (as well as molecular composition) are difficult to separate by size exclusion chromatography. Hence we have also developed C-terminal His-tagged version of VLM s-Ontak.

C-Terminal His-Tagged VLM s-Ontak without TEV Cleavage Site.

As shown in SEQ ID: 42 (Protein sequence of C terminal His tag to VLM s-Ontak) it is possible to add the amino acid sequence HHHHHH to the immature protein sequence of VLM s-Ontak at its C-terminus. In this version, the sequence HHHHHH appears immediately after the C-terminal threonine of VLM s-Ontak ( . . . IISTLT). The mature, secreted protein sequence of this C-terminal His-tagged VLM s-Ontak is shown in SEQ ID: 43 (Protein sequence of C terminal His tag to VLM s-Ontak after signal sequence is cleaved) which is a good candidate for Nickel-column affinity purification with its $His_6$ tag.

C-Terminal His-Tagged VLM s-Ontak with TEV Cleavage Site.

In order to avoid having the $His_6$ sequence in the final polypeptide sequence of the above version of VLM s-Ontak made by C-terminal His-tagging (SEQ ID: 43), it is possible to insert a TEV recognition sequence at the C-terminus to enable removal of the His-tag sequence. In this version, the sequence ENLYFQGHHHHHHHHH appears immediately after the C-terminal threonine of VLM s-Ontak ( . . . IISTLT). Since nickel affinity binding is enhance by poly-His sequences even longer than six amino acids, it is possible to include nine His residues. The amino acid sequence of this C-terminal His-tagged VLM s-Ontak with TEV cleavage site is shown in SEQ ID: 45 (Protein sequence of C terminal TEV His9 tag to VLM s-Ontak). The mature, secreted protein sequence of this C-terminal His-tagged VLM s-Ontak with TEV cleavage site is shown in SEQ ID: 46 (Protein sequence of C terminal TEV His9 tag to VLM s-Ontak after signal sequence is cleaved) and is a good candidate for Nickel-column affinity purification with its $His_9$ tag. The affinity purified VLM s-Ontak may then be exposed to small amounts of pure TEV protease, leading to enzymatic proteolysis that removes the 10 C-terminal residues GHHHHHHHHH, and releases mature, untagged VLM s-Ontak as is shown in SEQ ID: 30. Of note, this version of purified VLM s-Ontak (SEQ ID: 30) is 526 amino acids in length rather than 520 amino acids (SEQ ID 15) because it contains six additional amino acids of the TEV protease recognition sequence (ENLYFQ fused to the usual C-terminus threonine of VLM s-Ontak ( . . . IISTLT). The end result of this version of C-terminal His-tagged VLM s-Ontak with TEV cleavage site (SEQ ID: 30) is a C-terminal sequence . . . IISTLTENLYFQ.

Manufacturing Method for VLM s-Ontak which Include His-Tags and TEV Protease Sites.

The above three His-tag versions of VLM s-Ontak (N-terminal $His_6$ tag with TEV protease site, C-terminal $His_6$ tag without TEV protease site, and C-terminal $His_9$ tag with TEV protease site) are examples of methods to use His-tag/Nickel column affinity chromatography in the manufacturing method of VLM s-Ontak. Because of secreted proteases from *Corynebacterium diphtheriae* C7 that are present in the culture supernatant, it is important to purify VLM s-Ontak away from other proteins in the culture supernatant rapidly in order to avoid significant loss of the desired product. The inclusion of His-tags and TEV protease sites represents a significant improvement and may enable a rapid, streamlined manufacturing process for VLM s-Ontak Generation of *Corynebacterium diphtheriae* C7 Lacking Key Secreted Proteases for Improved Manufacturing of VLM s-Ontak.

The genome sequence of *Corynebacterium diphtheriae* C7 reveals two secreted proteases: Protease 1 is NCBI Reference Sequence WP_014318592.1 (SEQ ID: 32, 33) and Protease 2 is NCBI Reference Sequence WP_014318898.1 (SEQ ID: 35, 36). These proteases may be genetically deleted using the method of Ton-That and Scheewind (Ton-That H, Schneewind O. Assembly of pili on the surface of *Corynebacterium diphtheriae*. Mol Microbiol. 2003 November; 50(4):1429-38. PubMed PMID: 14622427) and also Allen and Schmitt (Allen C E, Schmitt M P. HtaA is an iron-regulated hemin binding protein involved in the utilization of heme iron in *Corynebacterium diphtheriae*. J Bacteriol. 2009 April; 191(8):2638-48. PubMed PMID: 19201805). The allelic exchange substrates to knock out protease 1 and protease 2 are shown in SEQ ID: 34 and SEQ ID: 37, respectively. These sequences when inserted into pk18mobsacB, a conjugative, mating plasmid with sacB counterselection (Schafer A, Tauch A, Jager W, Kalinowski J, Thierbach G, Pühler A (1994) Small mobilizable multi-purpose cloning vectors derived from the *Escherichia coli* plasmids pK18 and pK19: selection of defined deletions in the chromosome of *Corynebacterium glutumicum*. Gene 145:69-73. PMID: 8045426), lead to constructs which will knockout each protease. A recombinant *Corynebacterium diphtheriae* strain lacking both protease 1 and protease 2 will be a valuable production strain for future manufacturing methods to generate VLM s-Ontak.

Protein Manufacturing Process of Diphtheria Toxin-Based Fusion Proteins

Using the DNA plasmids and expression vectors of the present invention, a novel process was discovered eliminating the problems associated with the conventional method of manufacturing Ontak®. Ontak® is currently expressed using a DNA vector in an *E. coli* expression system. c-denileukin diftitox or Ontak® is 521 amino acids in length and has a molecular weight of 58 kD. The conventional Ontak® manufacturing process results in the formation of Ontak® aggregates of heterogeneous molecular weight, residual DNA, and excessive residual detergent in the final formulation resulting in the FDA placing classic-Ontak® on clinical hold in June 2011. As observed in FIG. 8a, Ontak® is expressed from a plasmid in *E. coli* and results in insoluble, cytosolic Ontak® (protein) accumulations known as inclusion body forms. Using the process of the present invention, FIG. 8b illustrates the expression of s-denileukin diftitox as an extracellular mature secreted protein in a cell free supernatant that can be easily purified and results in higher protein yields as illustrated in FIG. 9. FIG. 9 shows both a Coomassie Blue stain for total protein and an anti-IL2 immunoblot of s-denileukin diftitox generated using the process of the present invention probed with anti-IL-2.

The novel process of the present invention comprises: 1) transforming bacteria, preferably a *Corynebacterium diphtheria* strain, with a DNA expression vector of the present invention, 2) forming a transformant; 3) incubating the transformant in a culture medium for a period of time to allow growth and expression of a protein (such as a diphtheria toxin-based fusion protein and CRM typically containing a signal peptide), 4) secretion of the protein into the culture medium (due to a signal peptide attached to the protein); and (8) purifying the diphtheria toxin-based fusion protein from the culture medium. The DNA expression vectors include a ToxP and mutant ToxO that regulate the expression of at least one protein, such as a diphtheria toxin fusion protein, CRM protein, or other protein that may be attached to a signal peptide of the present invention.

Therapeutic Applications of Diphtheria Toxin-Based Fusion Proteins of the Present Invention Clinical efficacy of Ontak® has been demonstrated in cutaneous T cell lymphoma, peripheral T cell lymphoma, steroid-refractory graft versus host disease, methotrexate-refractory psoriasis, and methotrexate-refractory rheumatoid arthritis. Clinical efficacy has also been demonstrated in malignant melanoma and ovarian carcinoma as shown in FIG. 14. The diphtheria toxin-based fusion proteins of the present invention (including s-denileukin diftitox, ms-denileuken diftitox, is-denileukin diftitox-VLM, ms-denileukin diftitox-VLM) produced by the methods of the present invention will perform similarly, or better, than Ontak® that is commercially available with regard to clinical efficacies of treating or preventing disease.

Treatment for Tuberculosis.

As illustrated in FIG. 10, inventors of the present invention believe diphtheria toxin fusion proteins of the present invention will be active against tuberculosis. Denileukin diftitox is known to deplete IL-2-receptor (CD25+)-bearing cells including T regulatory ($T_{regs}$) cells. $T_{regs}$ cells express CD25 as well as FoxP3 and are immunosuppressive by their inhibition of Teffector ($T_{eff}$) cells. $T_{eff}$ cells such as CD4+ Thelper ($T_h$) cells and CD8+ cytotoxic T lymphocytes (CTLs) are needed within a tuberculous granuloma to contain the *M. tuberculosis* bacterial infection. During tuberculous infection, cellular lesions called granulomas form to contain the infection but are unable to fully eradicate the bacilli. Regulatory T cells (Tregs) are recruited to granulomas, leading to suppression of effector T cell function, potentially contributing to a permissive environment for *M. tuberculosis* persistence and growth. The diphtheria toxin fusion proteins of the present invention are used to deplete Tregs, which express IL-2 receptor, in order to ameliorate immune suppression by these cells during TB infection. FIG. 11 illustrates diphtheria fusion proteins used in the in vivo treatment of subjects (mice) with *M. tuberculosis*. Mice were infected with *M. tb.* strain H37Rv by aerosol infection giving an initial implantation of ~2.8 $\log_{10}$ CFU counts in lungs on day 0. The groups of mice were treated with 750 ng of c-Ontak® intraperitoneally (IP) or intravenously (IV) as one treatment cycle (1×, dosed at week 2 post-infection) or two treatment cycles (2×, dosed at ~day 3 pre-infection and week 2 post-infection). A treatment cycle of denileukin diftitox is defined as 35 mg/kg (750 ng for a typical mouse) given two times, two days apart. RHZ daily treatment by oral gavage was started at week 2. R is rifampin and was given to mice at 10 mg/kg. H is isoniazid and was given to mice at 10 mg/kg. Z is pyrazinamide and was given to mice at 150 mg/kg. The outcome of this study is illustrated in FIGS. 12 and 13.

Treatment for Cancer

Tregs have also been shown to inhibit anti-tumor immunity, and the cellular expansion of Tregs in tumors generally correlates with poor prognosis in patients. Denileukin diftitox treatment in melanoma patients resulted in transient depletion of Tregs and increased 1 year median overall survival. s-denileukin diftitox and s-denileukin diftitox-VLM of the present invention will be used to deplete Tregs in patients with tumors heavily infiltrated with Tregs as a cancer immunotherapy.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the described elements of the invention in all possible variations thereof is encompassed by the invention unless otherwise indicated herein or otherwise clearly contradicted by context.

Embodiments of the disclosure concern methods and/or compositions for treating and/or preventing disorders such as cancer and tuberculosis in which a subject is administered a composition of the present invention comprising a nucleic acid or protein sequence such as anyone of SEQ ID NOs: 11-15, or fusion proteins thereof.

An individual known to having disease such as cancer and/or tuberculosis, suspected of having such a disease, or at risk for having such a disease may be provided an effective amount of a composition of the present invention comprising a nucleic acid or protein sequence such as anyone of SEQ ID NOs: 11-15, or fusion proteins thereof. Those at risk for cancer or tuberculosis may be those individuals having one or more genetic factors, may be of advancing age, and/or may have a family history, for example.

In particular embodiments of the disclosure, an individual is given an agent for cancer and/or tuberculosis therapy in addition to a composition of the present invention comprising a nucleic acid or protein sequence such as anyone of SEQ ID NOs: 11-15, or fusion proteins thereof. Such additional therapy may include chemotherapy or antimicrobial agents, for example. When combination therapy is employed with a composition of the present invention comprising a nucleic acid or protein sequence such as anyone of SEQ ID NOs: 11-15, or fusion proteins thereof, the additional therapy may be given prior to, at the same time as, and/or subsequent to a composition of the present invention comprising a nucleic acid or protein sequence such as anyone of SEQ ID NOs: 11-15, or fusion proteins thereof.

Pharmaceutical Preparations

Pharmaceutical compositions of the present invention comprise an effective amount of one or more composition of the present invention comprising a nucleic acid or protein sequence such as anyone of SEQ ID NOs: 11-15, or fusion proteins thereof, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one composition of the present invention comprising a nucleic acid or protein sequence such as anyone of SEQ ID NOs: 11-15, or fusion proteins thereof, or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The one or more compositions of the present invention comprising a nucleic acid or protein sequence such as anyone of SEQ ID NOs: 11-15, or fusion proteins thereof, may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The one or more compositions of the present invention comprising a nucleic acid or protein sequence such as anyone of SEQ ID NOs: 11-15, or fusion proteins thereof, may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include one or more composition of the present invention comprising a nucleic acid or protein sequence such as anyone of SEQ ID NOs: 11-15, or fusion proteins thereof, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the one or more compositions of the present invention comprising a nucleic acid or protein sequence such as anyone of SEQ ID NOs: 11-15, or fusion proteins thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the one or more compositions of the present invention comprising a nucleic acid or protein sequence such as anyone of SEQ ID NOs: 11-15, or fusion proteins thereof, are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, one or more composition of the present invention comprising a nucleic acid or protein sequence such as anyone of SEQ ID NOs: 11-15, or fusion proteins thereof, may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the one or more compositions of the present invention comprising a nucleic acid or protein sequence such as anyone of SEQ ID NOs: 11-15, or fusion proteins thereof, may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, one or more composition of the present invention comprising a nucleic acid or protein sequence such as anyone of SEQ ID NOs: 11-15, or fusion proteins thereof, may be comprised in a kit.

The kits may comprise a suitably aliquoted of one or more compositions of the present invention comprising a nucleic acid or protein sequence such as anyone of SEQ ID NOs: 11-15, or fusion proteins thereof, and in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more compositions of the present invention comprising a nucleic acid or protein sequence such as anyone of SEQ ID NOs: 11-15, or fusion proteins thereof, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more compositions of the present invention comprising a nucleic acid or protein sequence such as anyone of SEQ ID NOs: 11-15, or fusion proteins thereof, may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The invention claimed is:

1. A fusion protein having an amino acid sequence selected from the group consisting of SEQ ID NOs: 12, 14, 15, and 43.

2. A pharmaceutical composition comprising a fusion protein of claim 1.

3. The pharmaceutical composition of claim 2, and at least one or more chemotherapy agents.

4. A protein having the amino acid sequence of any one of SEQ ID NOs: 12, 14, 15, and 43.

5. The pharmaceutical composition comprising a fusion protein of claim 1, and at least one or more chemotherapy agents.

6. The pharmaceutical composition of claim 3, wherein the other chemotherapy agent is selected from the group consisting from isoniazid, rifampin, rifabutin, rifapentine, pyrazinamide, ethambutol, streptomycin, amikacin, kanamycin, ethionamide, protionamide, terizidone, thiacetazone, cycloserine, caperomycin, para-amino salicylic acid (PAS), viomycin, linezolid, tedezolid, amoxicillin-clavulanic acid, meropenem, imipenem, clarithromycin, or clofazimine.

7. The pharmaceutical composition of claim 2 comprising one or more antimicrobial agents.

* * * * *